US011383440B2

(12) United States Patent
Patel et al.

(10) Patent No.: US 11,383,440 B2
(45) Date of Patent: Jul. 12, 2022

(54) THREE-DIMENSIONAL PRINTING SYSTEM AND EQUIPMENT ASSEMBLY

(71) Applicant: APRECIA PHARMACEUTICALS LLC, Blue Ash, OH (US)

(72) Inventors: Mahendra R. Patel, Milltown, NJ (US); Amit S. Patel, Ahmedabad (IN); Thomas J. Bradbury, Yardley, PA (US); Thomas G. West, Lawrenceville, NJ (US)

(73) Assignee: APRECIA PHARMACEUTICALS LLC, Blue Ash, OH (US)

( * ) Notice: Subject to any disclaimer, the term of this patent is extended or adjusted under 35 U.S.C. 154(b) by 481 days.

(21) Appl. No.: 15/872,573

(22) Filed: Jan. 16, 2018

(65) Prior Publication Data

US 2018/0141275 A1    May 24, 2018

Related U.S. Application Data

(63) Continuation of application No. PCT/US2016/047709, filed on Aug. 19, 2016.
(Continued)

(51) Int. Cl.
*B29C 64/241* (2017.01)
*B29C 64/165* (2017.01)
(Continued)

(52) U.S. Cl.
CPC ............. *B29C 64/241* (2017.08); *A61K 9/14* (2013.01); *B28B 11/06* (2013.01); *B29C 64/165* (2017.08);
(Continued)

(58) Field of Classification Search
CPC .............................. B29C 64/241; B33Y 10/00
See application file for complete search history.

(56) References Cited

U.S. PATENT DOCUMENTS 4,295,810 A   10/1981   Dennert et al.
4,592,916 A    6/1986   Akesson
(Continued)

FOREIGN PATENT DOCUMENTS

AU    2015 203 562 A1    7/2015
CN        1671503 A       9/2005
(Continued)

OTHER PUBLICATIONS

First Office Action dated Jun. 2, 2021 in related Australia Application No. 2016310470 filed Feb. 2, 2018 (4 pages).
(Continued)

*Primary Examiner* — Nicholas R Krasnow
(74) *Attorney, Agent, or Firm* — Daniel F. Nesbitt; Nesbitt IP LLC

(57) ABSTRACT

A three-dimensional printing system and equipment assembly for the manufacture of three-dimensionally printed articles is provided. The equipment assembly includes a three-dimensional printing build system, an optional liquid removal system and an optional harvester system. The build system includes a conveyor, plural build modules and at least one build station having a powder-layering system and a printing system. The equipment assembly can be used to manufacture pharmaceutical, medical, and non-pharmaceutical/non-medical objects. It can be used to prepare single or multiple articles.

16 Claims, 35 Drawing Sheets

Related U.S. Application Data

(60) Provisional application No. 62/208,022, filed on Aug. 21, 2015, provisional application No. 62/208,261, filed on Aug. 21, 2015.

(51) Int. Cl.
  *B30B 11/08* (2006.01)
  *B29C 64/176* (2017.01)
  *B33Y 10/00* (2015.01)
  *B28B 11/06* (2006.01)
  *B33Y 30/00* (2015.01)
  *B29C 64/379* (2017.01)
  *B33Y 40/00* (2020.01)
  *B29C 64/188* (2017.01)
  *B29C 64/30* (2017.01)
  *A61K 9/14* (2006.01)
  *B29K 105/00* (2006.01)

(52) U.S. Cl.
  CPC .......... *B29C 64/176* (2017.08); *B29C 64/188* (2017.08); *B29C 64/30* (2017.08); *B29C 64/379* (2017.08); *B30B 11/08* (2013.01); *B33Y 10/00* (2014.12); *B33Y 30/00* (2014.12); *B33Y 40/00* (2014.12); *B29K 2105/0035* (2013.01); *B29K 2105/251* (2013.01); *B29K 2995/0064* (2013.01)

(56) References Cited

U.S. PATENT DOCUMENTS

| | | |
|---|---|---|
| 5,121,329 A | 6/1992 | Crump |
| 5,127,037 A | 6/1992 | Bynum |
| 5,204,055 A | 4/1993 | Sachs |
| 5,252,264 A | 10/1993 | Forderhase |
| 5,340,656 A | 8/1994 | Sachs |
| 5,490,962 A | 2/1996 | Cima et al. |
| 5,518,680 A | 5/1996 | Cima |
| 5,637,175 A | 6/1997 | Feygin |
| 5,717,599 A | 2/1998 | Menhennett |
| 5,851,465 A | 12/1998 | Bredt |
| 5,869,170 A | 2/1999 | Cima et al. |
| 5,874,279 A | 2/1999 | Cochran |
| 5,879,489 A | 3/1999 | Burns |
| 5,902,441 A | 5/1999 | Bredt |
| 5,934,343 A | 8/1999 | Gaylo |
| 5,940,674 A | 8/1999 | Sachs |
| 6,007,318 A | 12/1999 | Russell |
| 6,064,759 A | 5/2000 | Buckley |
| 6,146,567 A | 11/2000 | Sachs |
| 6,165,406 A | 12/2000 | Jang |
| 6,193,923 B1 | 2/2001 | Leyden |
| 6,200,508 B1 | 3/2001 | Jacobson |
| 6,213,168 B1 | 4/2001 | Gaylo |
| 6,280,771 B1 | 8/2001 | Monkhouse et al. |
| 6,336,480 B2 | 1/2002 | Gaylo |
| 6,363,606 B1 | 4/2002 | Johnson |
| 6,375,874 B1 | 4/2002 | Russell |
| 6,403,002 B1 | 6/2002 | Van Der Geest |
| 6,416,850 B1 | 7/2002 | Bredt |
| 6,508,971 B2 | 1/2003 | Leyden |
| 6,514,518 B2 | 2/2003 | Monkhouse |
| 6,530,958 B1 | 3/2003 | Cima et al. |
| 6,531,086 B1 | 3/2003 | Larsson |
| 6,547,994 B1 | 4/2003 | Monkhouse |
| 6,596,224 B1 | 7/2003 | Sachs |
| 6,610,429 B2 | 8/2003 | Bredt |
| 6,702,100 B2 | 3/2004 | Studer |
| 6,772,026 B2 | 8/2004 | Bradbury |
| 6,776,099 B1 | 8/2004 | Landa |
| 6,796,788 B2 | 9/2004 | Gallagher |
| 6,838,035 B1 | 1/2005 | Ederer |
| 6,850,334 B1 | 2/2005 | Gothait |
| 6,890,957 B2 | 5/2005 | Chandran |
| 6,905,645 B2 | 6/2005 | Iskra |
| 6,945,638 B2 | 9/2005 | Teung |
| 6,989,115 B2 | 1/2006 | Russell |
| 7,004,222 B2 | 2/2006 | Ederer et al. |
| 7,220,380 B2 | 5/2007 | Farr |
| 7,291,002 B2 | 11/2007 | Russell |
| 7,296,990 B2 | 11/2007 | Devos |
| 7,365,129 B2 | 4/2008 | Kramer |
| 7,435,368 B2 | 10/2008 | Davidson |
| 7,455,804 B2 | 11/2008 | Patel |
| 7,828,022 B2 | 11/2010 | Davidson |
| 8,017,055 B2 | 9/2011 | Davidson |
| 8,888,480 B2 | 11/2014 | Yoo |
| 9,517,591 B2 | 12/2016 | Yoo |
| 9,517,592 B2 | 12/2016 | Yoo |
| 9,610,735 B2 | 4/2017 | Yoo |
| 9,833,955 B2 | 12/2017 | Muller et al. |
| 9,908,293 B2 | 3/2018 | Yoo |
| 2001/0017085 A1 | 8/2001 | Kubo |
| 2001/0028471 A1 | 10/2001 | Hirokazu |
| 2001/0045678 A1 | 11/2001 | Kubo et al. |
| 2002/0015728 A1 | 2/2002 | Payumo |
| 2002/0033548 A1 | 3/2002 | Brodkin |
| 2002/0064745 A1 | 5/2002 | Schulman |
| 2002/0079601 A1 | 6/2002 | Russell |
| 2002/0114652 A1 | 8/2002 | Morozumi |
| 2002/0125592 A1 | 9/2002 | Schulman |
| 2003/0089078 A1 | 5/2003 | Cristina |
| 2003/0143268 A1* | 7/2003 | Pryce Lewis ........ A61K 9/2095 424/464 |
| 2003/0198677 A1 | 10/2003 | Pryce Lewis |
| 2003/0207959 A1 | 11/2003 | Napadensky |
| 2003/0228368 A1 | 12/2003 | Wynn et al. |
| 2004/0003738 A1 | 1/2004 | Imiolek |
| 2004/0003741 A1 | 1/2004 | Iskra |
| 2004/0004303 A1 | 1/2004 | Iskra |
| 2004/0004653 A1 | 1/2004 | Pryor |
| 2004/0005182 A1 | 1/2004 | Gaylo |
| 2004/0005360 A1 | 1/2004 | Wang |
| 2004/0012112 A1 | 1/2004 | Davidson |
| 2004/0018107 A1* | 1/2004 | Khoshnevis ........... B33Y 40/00 419/6 |
| 2004/0056378 A1 | 3/2004 | Bredt |
| 2004/0112523 A1 | 6/2004 | Crom |
| 2004/0118309 A1 | 6/2004 | Fedor |
| 2004/0141024 A1 | 7/2004 | Silverbrook |
| 2004/0141025 A1 | 7/2004 | Silverbrook |
| 2004/0141030 A1 | 7/2004 | Silverbrook |
| 2004/0141043 A1 | 7/2004 | Silverbrook |
| 2004/0145628 A1 | 7/2004 | Silverbrook |
| 2004/0145781 A1 | 7/2004 | Silverbrook |
| 2004/0173946 A1 | 9/2004 | Pfeifer |
| 2004/0177775 A1 | 9/2004 | Tweedy |
| 2004/0182510 A1 | 9/2004 | Pfeifer |
| 2004/0183796 A1 | 9/2004 | Velde |
| 2004/0187714 A1 | 9/2004 | Napadensky |
| 2004/0225398 A1 | 11/2004 | Silverbrook |
| 2004/0243133 A1 | 12/2004 | Materna |
| 2004/0252174 A1 | 12/2004 | Baxter |
| 2004/0262797 A1 | 12/2004 | Schulman |
| 2004/0265413 A1 | 12/2004 | Russell |
| 2005/0059757 A1 | 3/2005 | Bredt |
| 2005/0061241 A1 | 3/2005 | West |
| 2005/0066826 A1 | 3/2005 | Dubuit |
| 2005/0069784 A1 | 3/2005 | Gothait |
| 2005/0104241 A1 | 5/2005 | Kritchman |
| 2005/0152976 A1 | 7/2005 | Chenevier |
| 2005/0179721 A1 | 8/2005 | Jones |
| 2005/0197431 A1 | 9/2005 | Bredt |
| 2005/0204939 A1 | 9/2005 | Krejci |
| 2005/0208168 A1 | 9/2005 | Hickerson |
| 2005/0247216 A1 | 11/2005 | Reichwein |
| 2005/0275129 A1 | 12/2005 | Sambu |
| 2006/0030964 A1 | 2/2006 | Silverbrook |
| 2006/0035034 A1 | 2/2006 | Matsumoto |
| 2006/0077241 A1 | 4/2006 | Silverbrook |
| 2006/0099287 A1 | 5/2006 | Kim |
| 2006/0110443 A1 | 5/2006 | Payumo |
| 2006/0111807 A1 | 5/2006 | Gothait |

(56) References Cited

U.S. PATENT DOCUMENTS

| | | |
|---|---|---|
| 2006/0127153 A1 | 6/2006 | Menchik |
| 2006/0141145 A1 | 6/2006 | Davidson |
| 2006/0230970 A1 | 10/2006 | Pimia |
| 2006/0268044 A1 | 11/2006 | Silverbrook |
| 2006/0268057 A1 | 11/2006 | Silverbrook |
| 2007/0023977 A1* | 2/2007 | Braun ............... B29C 64/153 264/497 |
| 2007/0030326 A1 | 2/2007 | Silverbrook |
| 2007/0057412 A1 | 3/2007 | Weiskopf |
| 2007/0087071 A1 | 4/2007 | Devos |
| 2007/0126157 A1 | 6/2007 | Bredt |
| 2007/0146734 A1 | 6/2007 | Taniuchi |
| 2007/0150088 A1 | 6/2007 | Silverbrook |
| 2007/0168815 A1 | 7/2007 | Napadensky |
| 2007/0176312 A1 | 8/2007 | Clark |
| 2007/0182782 A1 | 8/2007 | Silverbrook |
| 2007/0182799 A1 | 8/2007 | Silverbrook |
| 2007/0187508 A1 | 8/2007 | Takayama |
| 2007/0188549 A1 | 8/2007 | Silverbrook |
| 2007/0195150 A1 | 8/2007 | Silverbrook |
| 2007/0252871 A1 | 11/2007 | Silverbrook |
| 2007/0259010 A1 | 11/2007 | Yoo |
| 2007/0289705 A1 | 12/2007 | Johnson |
| 2008/0042321 A1 | 2/2008 | Russell |
| 2008/0062214 A1 | 3/2008 | Silverbrook |
| 2008/0068416 A1 | 3/2008 | Silverbrook |
| 2008/0105144 A1 | 5/2008 | Tetsuka |
| 2008/0110395 A1 | 5/2008 | Kritchman |
| 2008/0118655 A1 | 5/2008 | Kritchman |
| 2008/0121130 A1 | 5/2008 | Kritchman |
| 2008/0121172 A1 | 5/2008 | Kritchman |
| 2008/0124464 A1 | 5/2008 | Kritchman |
| 2008/0138515 A1 | 6/2008 | Williams |
| 2008/0179786 A1 | 7/2008 | Sperry |
| 2008/0180509 A1 | 7/2008 | Maki |
| 2008/0187711 A1 | 8/2008 | Alam |
| 2008/0192074 A1 | 8/2008 | Dubois |
| 2008/0211132 A1 | 9/2008 | Feenstra |
| 2008/0229961 A1 | 9/2008 | Schneider |
| 2008/0231645 A1 | 9/2008 | Silverbrook |
| 2008/0241404 A1 | 10/2008 | Allaman |
| 2008/0259434 A1 | 10/2008 | Nagayama |
| 2008/0269939 A1 | 10/2008 | Kritchman |
| 2008/0269940 A1 | 10/2008 | Silverbrook |
| 2008/0275181 A1 | 11/2008 | Win |
| 2008/0277823 A1 | 11/2008 | Hayashi |
| 2008/0281019 A1 | 11/2008 | Giller |
| 2009/0011066 A1 | 1/2009 | Davidson |
| 2009/0025638 A1 | 1/2009 | Inoue |
| 2009/0060983 A1 | 3/2009 | Bunick et al. |
| 2009/0266804 A1 | 10/2009 | Costin |
| 2009/0020919 A1 | 11/2009 | Marsac |
| 2009/0314201 A1 | 12/2009 | Baccini |
| 2010/0002041 A1 | 1/2010 | Silverbrook |
| 2010/0006640 A1 | 1/2010 | Culp |
| 2010/0007696 A1 | 1/2010 | Silverbrook |
| 2010/0016348 A1 | 1/2010 | Bunick et al. |
| 2010/0075234 A1 | 3/2010 | Cousins |
| 2010/0098319 A1 | 4/2010 | Gombert |
| 2010/0151136 A1 | 6/2010 | Davidson |
| 2010/0174399 A1 | 7/2010 | Silverbrook |
| 2012/0052145 A1 | 3/2012 | Chen |
| 2012/0059504 A1 | 3/2012 | Pax |
| 2012/0092724 A1 | 4/2012 | Pettis |
| 2012/0105903 A1 | 5/2012 | Pettis |
| 2012/0113457 A1 | 5/2012 | Pettis |
| 2012/0113473 A1 | 5/2012 | Pettis |
| 2012/0286453 A1 | 11/2012 | Pettis |
| 2012/0294967 A1 | 11/2012 | Lin |
| 2013/0073073 A1 | 3/2013 | Pettis |
| 2013/0078013 A1 | 3/2013 | Chillscyzn |
| 2013/0108726 A1 | 5/2013 | Ucklemann |
| 2013/0186514 A1* | 7/2013 | Zhuang ............... B29C 64/205 141/11 |
| 2013/0186558 A1 | 7/2013 | Comb |
| 2014/0065194 A1* | 3/2014 | Yoo ............... B29C 64/165 424/400 |
| 2014/0170012 A1* | 6/2014 | Delisle ............... B22F 3/1055 419/6 |
| 2014/0178588 A1 | 6/2014 | Swanson et al. |
| 2014/0271862 A1 | 9/2014 | Jacob et al. |
| 2014/0374958 A1 | 12/2014 | Taniuchi et al. |
| 2015/0102531 A1 | 4/2015 | El-Siblani et al. |
| 2015/0123320 A1 | 5/2015 | Joyce |
| 2015/0183166 A1 | 7/2015 | Yoo |
| 2015/0224718 A1 | 8/2015 | Ederer |
| 2015/0246485 A1* | 9/2015 | Guenster ............... B29C 64/25 264/511 |
| 2015/0251351 A1 | 9/2015 | Feygin |
| 2015/0266236 A1 | 9/2015 | Farah |
| 2015/0314389 A1 | 11/2015 | Yamada |
| 2015/0336330 A1 | 11/2015 | Herzog |
| 2016/0214327 A1 | 7/2016 | Uckelmann |
| 2016/0339639 A1 | 11/2016 | Chivel |
| 2016/0339646 A1 | 11/2016 | Baecker |
| 2017/0160694 A1 | 6/2017 | Nowak et al. |
| 2017/0291362 A1 | 10/2017 | Tombs et al. |
| 2018/0141275 A1 | 5/2018 | Patel et al. |
| 2020/0338813 A1* | 10/2020 | Counts ............... B29C 64/153 |

FOREIGN PATENT DOCUMENTS

| | | |
|---|---|---|
| CN | 104760767 A | 7/2015 |
| DE | 20 2011 003 443 U1 | 2/2012 |
| EP | 0734842 A1 | 3/1996 |
| EP | 1631440 B1 | 6/2004 |
| EP | 1 775 103 A2 | 4/2007 |
| EP | 2 480 201 A2 | 8/2012 |
| JP | H07-508676 | 9/1995 |
| JP | 2005-507723 A | 3/2005 |
| WO | 9534468 A1 | 12/1995 |
| WO | 9828124 A3 | 7/1998 |
| WO | 03/028990 A1 | 4/2003 |
| WO | 2009/112886 A1 | 9/2009 |
| WO | 2012076205 A1 | 6/2012 |
| WO | 2013/092757 A1 | 6/2013 |
| WO | 2014/039378 A1 | 3/2014 |
| WO | 2015/163765 A1 | 10/2015 |
| WO | 2015/167335 A1 | 11/2015 |
| WO | 2017/034951 A1 | 3/2017 |

OTHER PUBLICATIONS

International Search Report for PCT/US2013/057466 (WO 2014/039378).

U.S. Appl. No. 15/871,445, filed Jan. 15, 2018, Yoo, et al.

U.S. Appl. No. 15/981,365, filed May 16, 2018, Yoo, et al.

Notice of Reason(s) for Rejection dated Jun. 30, 2020, in related Japanese Application No. 2018-528210 filed Aug. 19, 2016 (6 pages).

Extended European Search Report dated Apr. 30, 2021 in related European Application No. 21158435.4 filed Feb. 22, 2021 (11 pages).

Second Office Action dated May 4, 2021 in corresponding European Patent Office Application No. 16 839 868.3 filed Mar. 15, 2018 (8 pages).

First Office Action dated Aug. 18, 2020 in corresponding European Patent Office Application No. 16 839 868.3 filed Mar. 15, 2018 (7 pages).

Extended European Search Report dated Sep. 27, 2019 for corresponding European Application No. 16 839 868.3 filed Aug. 19, 2016 (12 pages).

Second Office Action dated Jul. 16, 2021 in related Chinese Application No. 201680048193.5 filed Aug. 19, 2016 (10 pages) with Google machine translation (10 pages).

First Office Action dated Sep. 3, 2020 in related Chinese Application No. 201680048193.5 filed Feb. 13, 2018 (11 pages) (with English translation, 13 pages).

First Office Action dated Sep. 18, 2020 in related Indian Application No. 201817003002 filed Jan. 25, 2018 (8 pages).

(56) References Cited

OTHER PUBLICATIONS

International Search Report with Written Opinion dated Jan. 23, 2020 by the International Searching Authority for related International Application No. PCT/US2019/056323, filed Oct. 15, 2019 (13 pages).
Jamroz Witold et al., "3D Printing in Pharmaceutical and Medical Applications—Recent Achievements and Challenges", Pharmaceutical Research, Springer New York LLC, vol. 35, No. 9, Jul. 11, 2018, pp. 1-22.
Supplemental International Search Report and Written Opinion by the USPTO, publicly available Apr. 23, 2020, for related International Application No. PCT/US2019/056323, filed Oct. 15, 2019 (7 pages).
Supplemental International Search Report and Written Opinion by the KIPO, publicly available Apr. 23, 2020, for related International Application No. PCT/US2019/056323, filed Oct. 15, 2019 (20 pages).
Supplemental International Search Report and Written Opinion by the CNIPA, publicly available Apr. 23, 2020, for related International Application No. PCT/US2019/056323, filed Oct. 15, 2019 (10 pages).
Supplemental International Search Report and Written Opinion by the JPO, publicly available Apr. 23, 2020, for related International Application No. PCT/US2019/056323, filed Oct. 15, 2019 (8 pages).
First Office Action dated Apr. 4, 2022 in copending Mexican Application No. MX/a/2018/001940 filed Feb. 15, 2018 (5 pages) with Google machine translation (3 pages).

\* cited by examiner

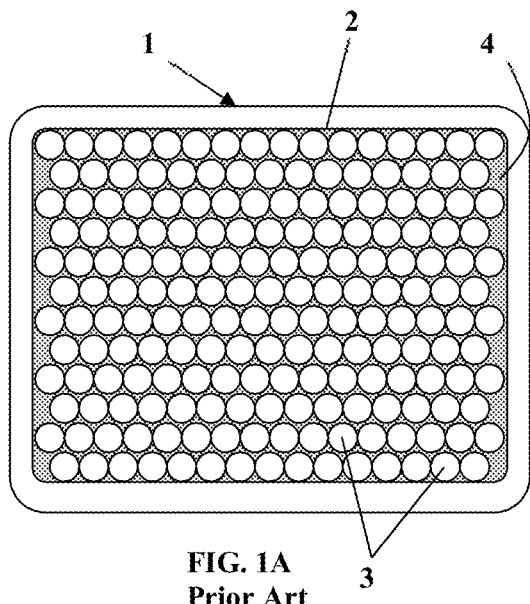
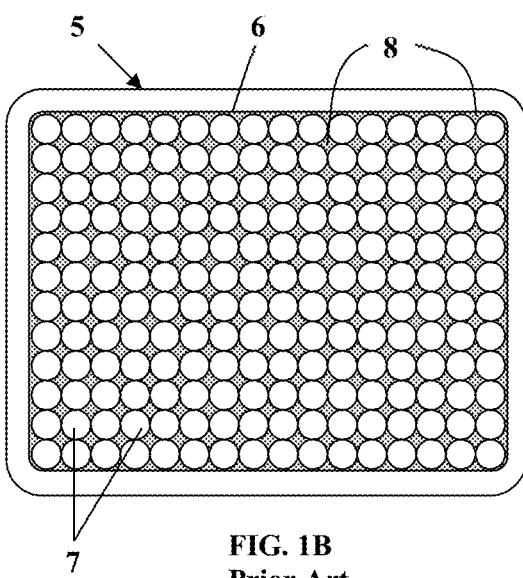
FIG. 1A
Prior Art
FIG. 1B
Prior Art
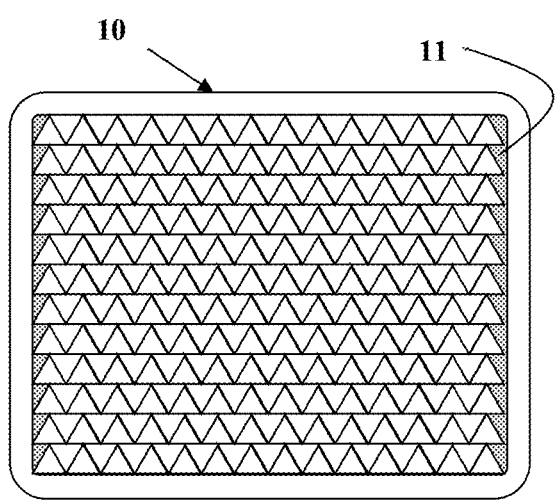
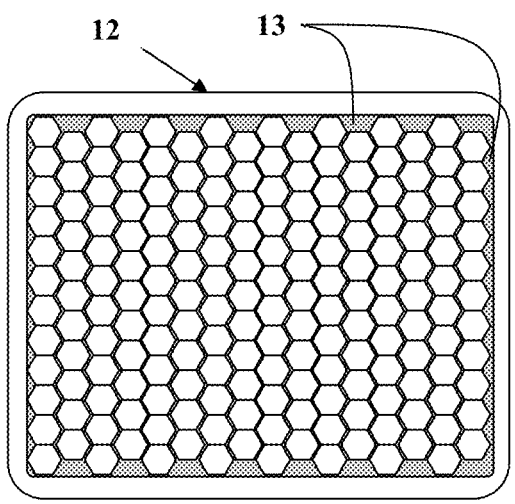
FIG. 1C
Prior Art
FIG. 1D
Prior Art

I

II

IV

III

V

VI

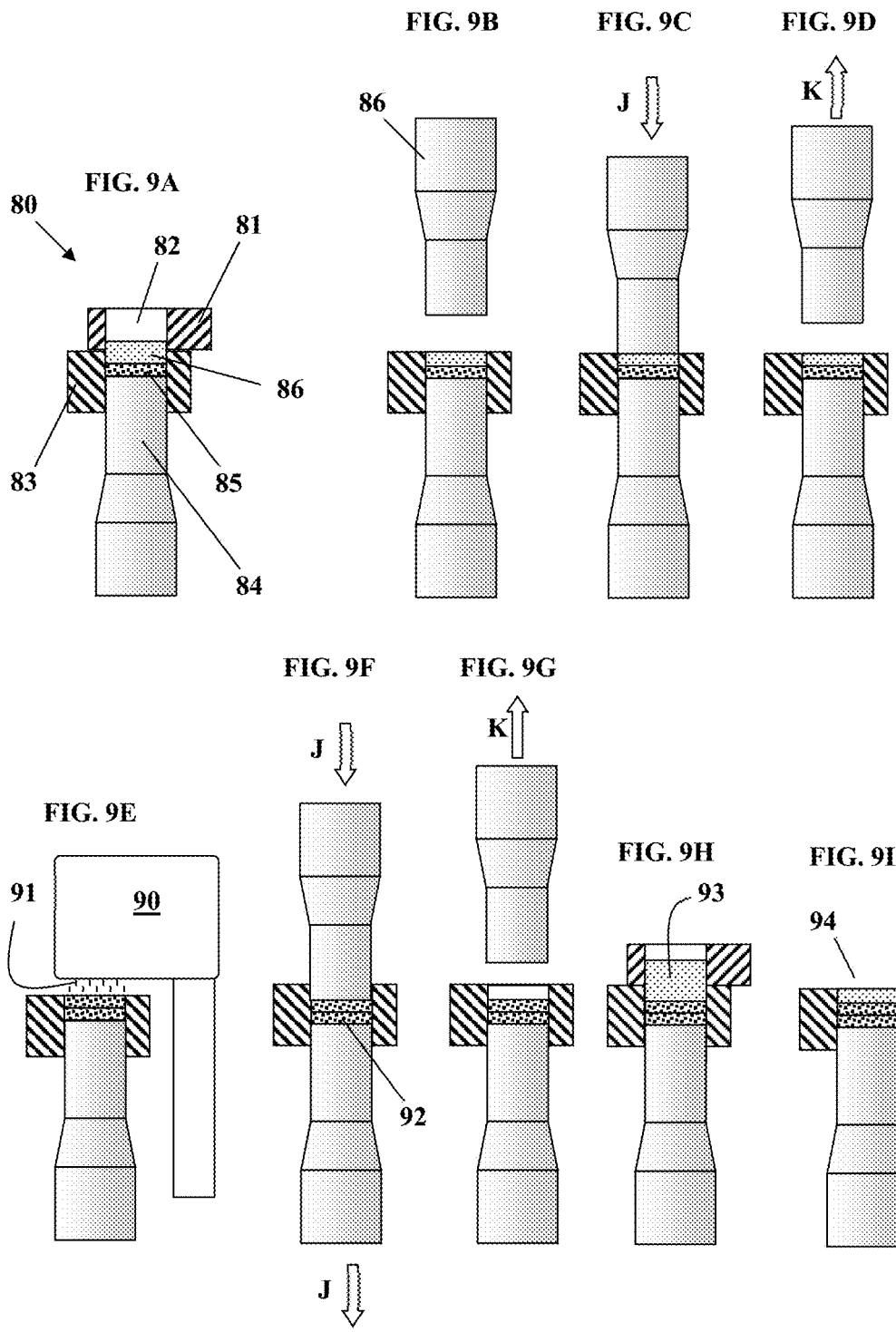

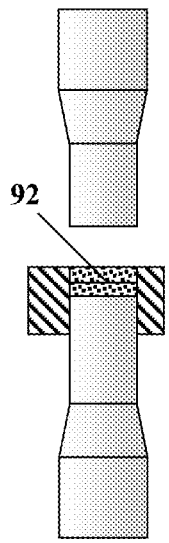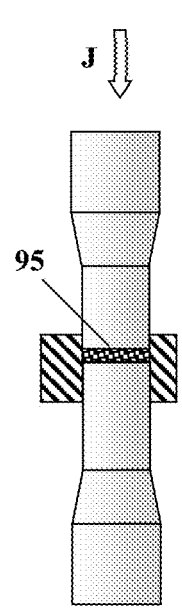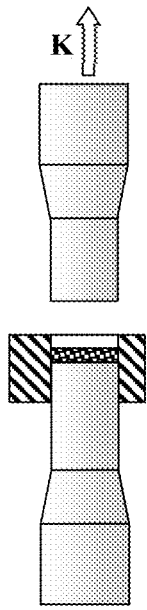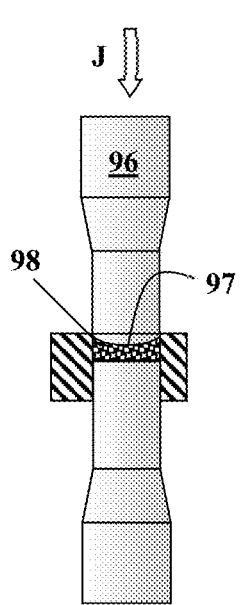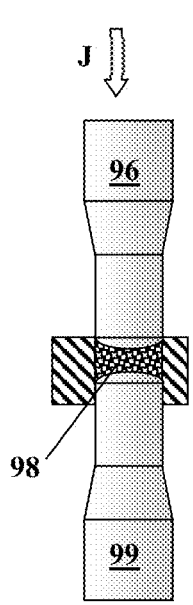
FIG. 10A  FIG. 10B  FIG. 10C  FIG. 11A  FIG. 11B
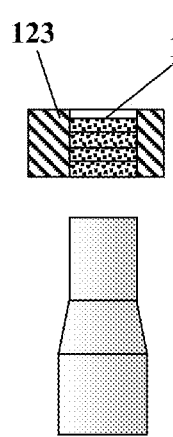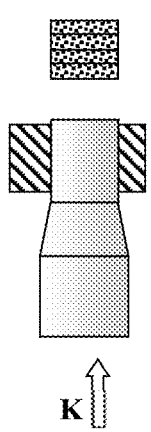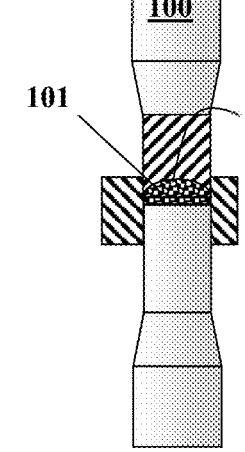
FIG. 12A  FIG. 12B  FIG. 11C  FIG. 11D  FIG. 11E

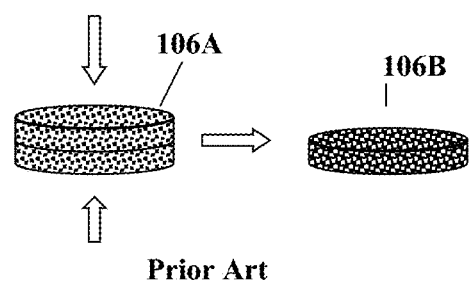
FIG. 13
Prior Art
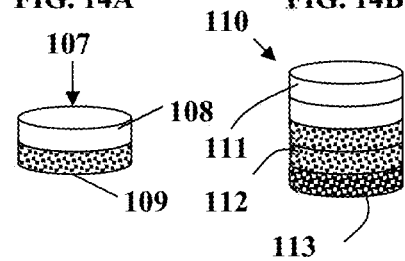
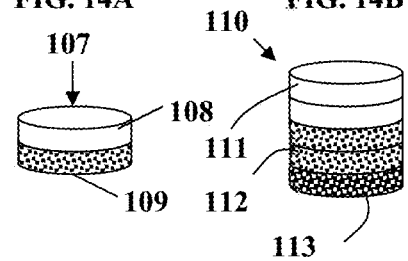
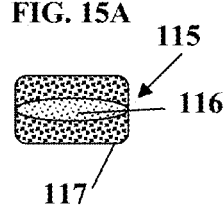
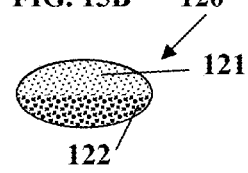
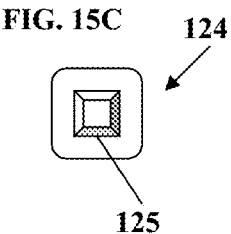
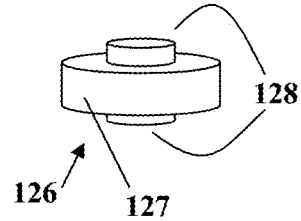
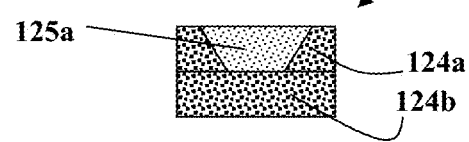
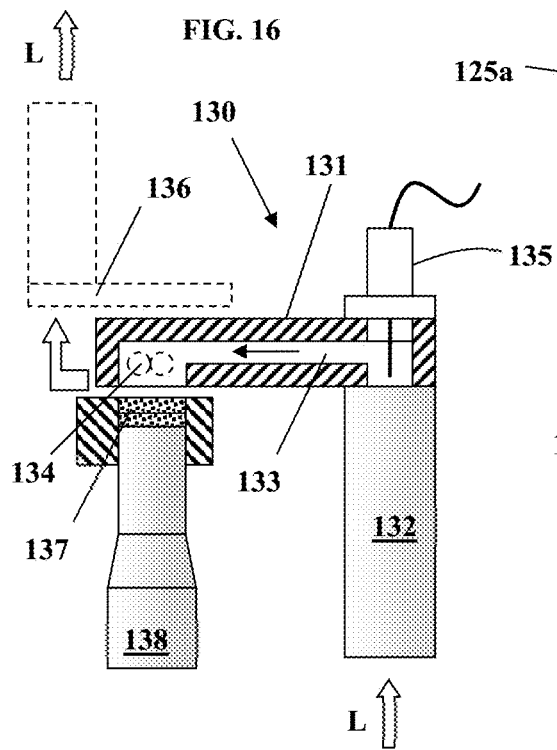
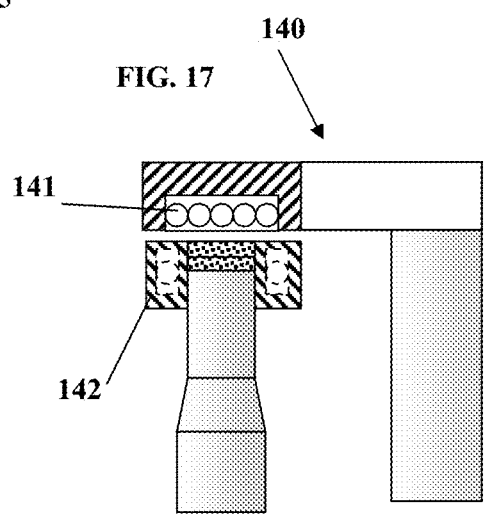

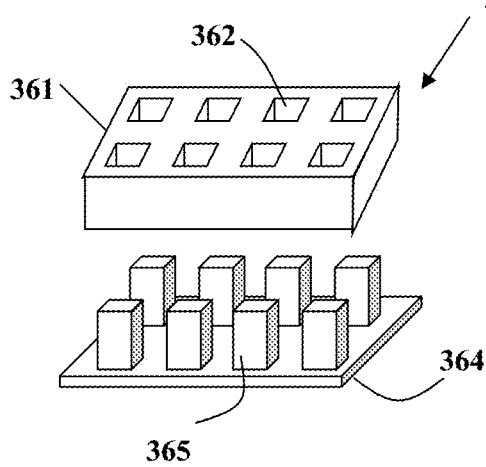
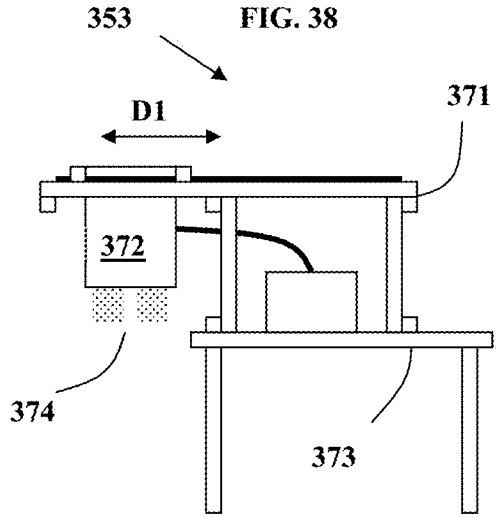
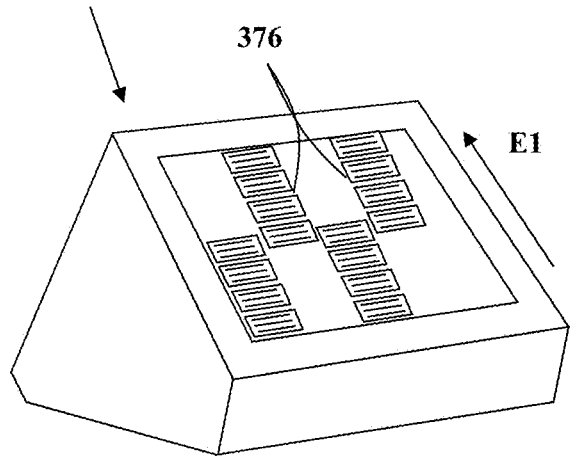
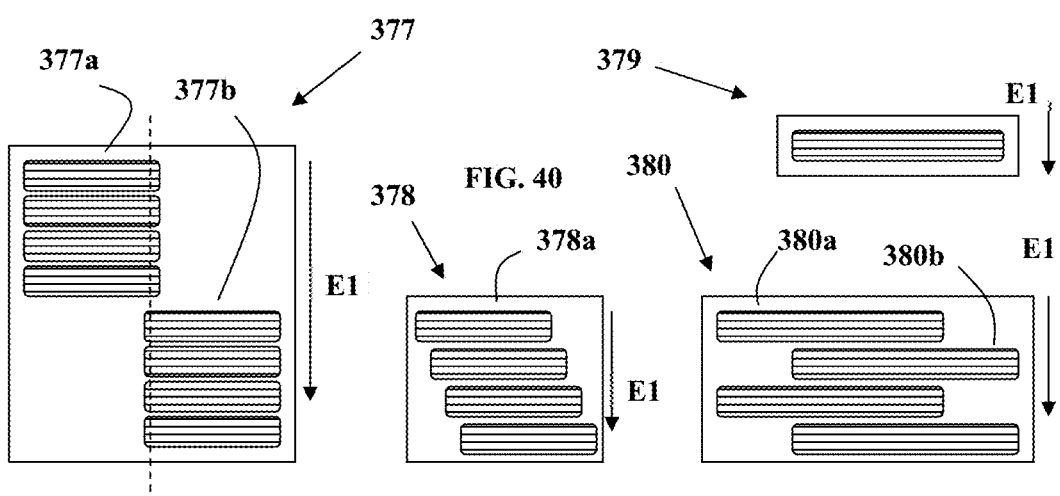

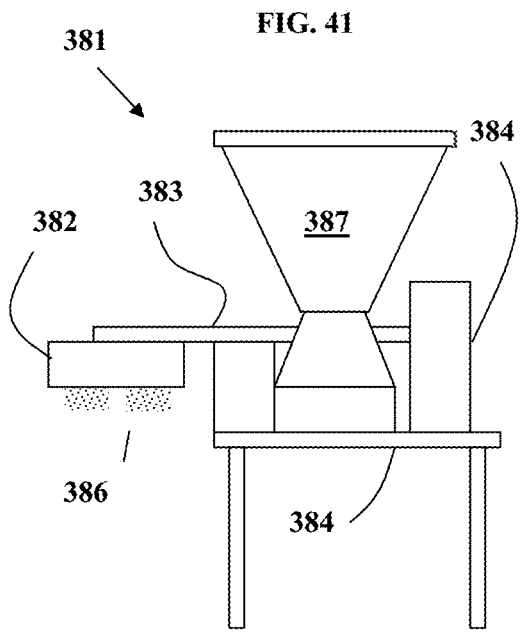
FIG. 41
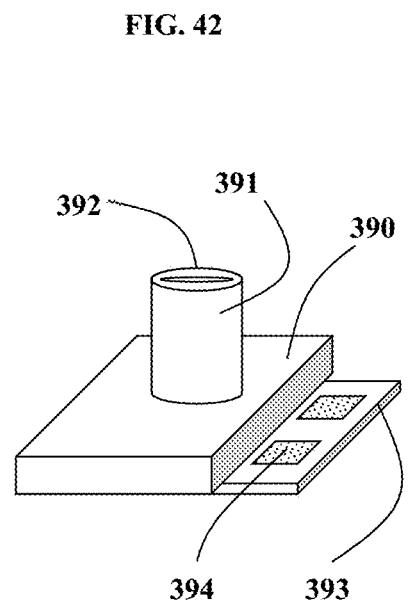
FIG. 42
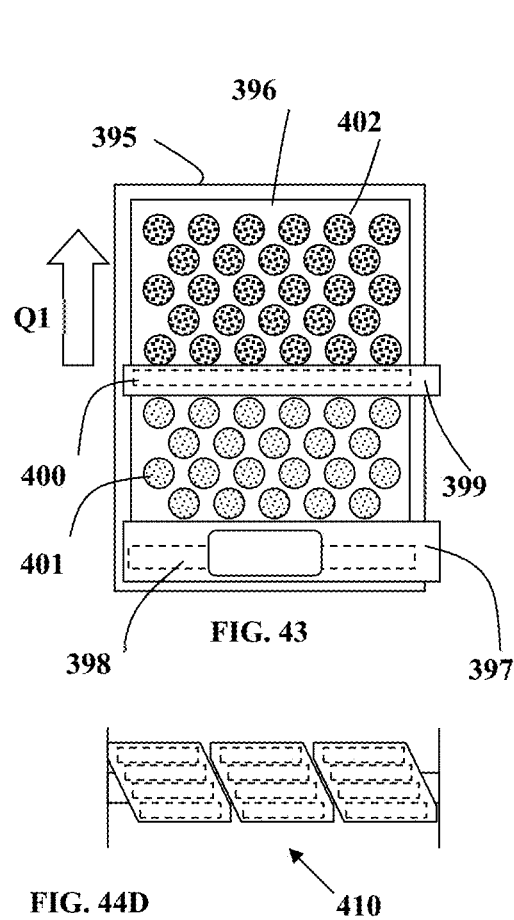
FIG. 43
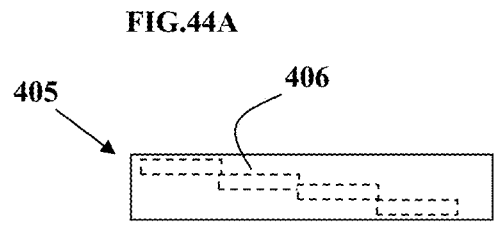
FIG. 44A
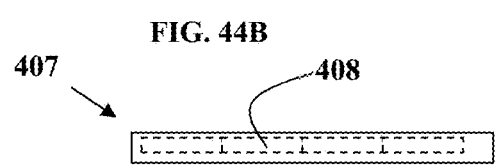
FIG. 44B
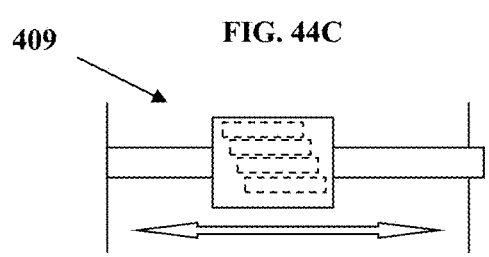
FIG. 44C
FIG. 44D

THREE-DIMENSIONAL PRINTING SYSTEM AND EQUIPMENT ASSEMBLY

CROSS-REFERENCE TO EARLIER FILED APPLICATIONS

The present application claims the benefit of and is a continuation of PCT/US2016/047709 filed Aug. 19, 2016, which claims the benefit of provisional applications 62/208,261 filed Aug. 21, 2015 and 62/208,022 filed Aug. 21, 2015, the entire disclosures of which are hereby incorporated by reference.

FIELD OF THE INVENTION

The present invention concerns a manufacturing system and equipment assembly and use thereof for the preparation of articles by cavity three-dimensional printing and for the preparation of articles with variable layer density.

BACKGROUND OF THE INVENTION

Rapid prototyping describes various techniques for fabricating a three-dimensional prototype of an object from a computer model of the object. One technique is three-dimensional printing, whereby a printer is used to fabricate the 3-D prototype from a plurality of two-dimensional layers. In particular, a digital representation of a 3-D object is stored in a computer memory. Computer software sections the representation of the object into a plurality of distinct 2-D layers. Alternatively, a stream (sequential series) of instructions for each incremental layer may be entered directly, e.g. a series of images. A 3-D printer then fabricates a thin layer of bound material for each 2-D image layer sectioned by the software. Together, the layers are printed one on top of the other and adhere to each other to form the desired prototype.

Three-dimensional powder-liquid printing technology has been used to prepare articles such as pharmaceutical dosage forms, mechanical prototypes and concept models, molds for casting mechanical parts, bone growth promoting implants, electronic circuit boards, scaffolds for tissue engineering, responsive biomedical composites, tissue growth promoting implants, dental restorations, jewelry, fluid filters and other such articles.

Three-dimensional printing is a solid freeform fabrication technique/rapid-prototyping technique in which thin layers of powder are spread onto a surface and selected regions of the powder are bound together by the controlled deposition ("printing") of a fluid. This basic operation is repeated layer-by-layer, with each new layer formed on top of and adhered to the previously printed layer, to eventually make three-dimensional objects within a bed of unbound powder. When the printed objects have sufficient cohesion, they may be separated from the unbound powder.

Systems and equipment assemblies for three-dimensional printing of articles are commercially available or in use by others: Massachusetts Institute of Technology Three-Dimensional Printing Laboratory (Cambridge, Mass.), Z Corporation's 3DP and HD3DP™ systems (Burlington, Mass.), The Ex One Company, L.L.C. (Irwin, Pa.), Soligen (Northridge, Calif.), Specific Surface Corporation (Franklin, Mass.), TDK Corporation (Chiba-ken, Japan), Therics L.L.C. (Akron, Ohio, now a part of Integra Lifesciences), Phoenix Analysis & Design Technologies (Tempe, Ariz.), Stratasys, Inc.'s Dimension™ system (Eden Prairie, Minn.), Objet Geometries (Billerica, Mass. or Rehovot, Israel), Xpress3D (Minneapolis, Minn.), and 3D Systems' Invision™ system (Valencia, Calif.).

Some systems have been described in the patent literature: U.S. Publications No. 20080281019, No. 20080277823, No. 20080275181, No. 20080269940, No. 20080269939, No. 20080259434, No. 20080241404, No. 20080231645, No. 20080229961, No. 20080211132, No. 20080192074, No. 20080187711, No. 20080180509, No. 20080138515, No. 20080124464, No. 20080121172, No. 20080121130, No. 20080118655, No. 20080110395, No. 20080105144, No. 20080068416, No. 20080062214, No. 20080042321, No. 20070289705, No. 20070259010, No. 20070252871, No. 20070195150, No. 20070188549, No. 20070187508, No. 20070182799, No. 20070182782, No. 20070168815, No. 20070146734, No. 20060268057, No. 20060268044, No. 20060230970, No. 20060141145, No. 20060127153, No. 20060111807, No. 20060110443, No. 20060099287, No. 20060077241, No. 20050054039, No. 20060035034, No. 20060030964, No. 20050247216, No. 20050204939, No. 20050197431, No. 20050179721, No. 20050104241, No. 20050069784, No. 20050061241, No. 20050059757, No. 20040265413, No. 20040262797, No. 20040252174, No. 20040243133, No. 20040225398, No. 20040187714, No. 20040183796, No. 20040145781, No. 20040145628, No. 20040145267, No. 20040143359, No. 20040141043, No. 20040141030, No. 20040141025, No. 20040141024, No. 20040118309, No. 20040112523, No. 20040056378, No. 20040012112, No. 20040005360, No. 20040005182, No. 20040004653, No. 20040004303, No. 20040003741, No. 20040003738, No. 20030207959, No. 20030198677, No. 20030143268, No. 20020125592, No. 20020114652, No. 20020079601, No. 20020064745, No. 20020033548, No. 20020015728, No. 20010028471, and No. 20010017085; U.S. Pat. Nos. 5,490,962, 5,204,055, 5,121,329, 5,127,037, 5,252,264, 5,340,656, 5,387,380, 5,490,882, 5,518,680, 5,717,599, 5,851,465, 5,869,170, 5,874,279, 5,879,489, 5,902,441, 5,934,343, 5,940,674, 6,007,318, 6,146,567, 6,165,406, 6,193,923, 6,200,508, 6,213,168, 6,336,480, 6,363,606, 6,375,874, 6,416,850,6,508,971, 6,530,958, 6,547,994, 6,596,224, 6,772,026, 6,838,035, 6,850,334, 6,905,645, 6,945,638, 6,989,115, 7,220,380, 7,291,002 7,365,129, 7,435,368, 7,455,804, 7,686,955, 7,828,022, 8,017,055, and 8,888,480; PCT International Publications No. WO 00/26026, No. WO 98/043762, No. WO 95/034468, No. WO 95/011007, No. WO 2014/039378; and European Patent No. 1,631,440, which employs a cylindrical (radial or polar) coordinate-based system due to its construction.

Three-dimensional printing systems employing powder and binding fluid typically form articles by placing layers of powder within a receptacle and depositing binding fluid on the individual layers of powder. The binding fluid is applied in patterns to regions of the powder in each layer such that unbound powdered material remains on the outer periphery of the patterns. The printed articles, which comprise bound powder, are then separated from substantial amounts of unbound powder. Such processes undesirably require wasting or recycling the unbound powder. It would be a substantial improvement in the field to provide an equipment assembly, system and method for substantially reducing or eliminating the need to waste or recycle unbound powder.

Three-dimensional printing systems have most often been directed to the manufacturing of custom or "one-off" parts, or in some cases toward mass customization. This may include fabrication of many different parts exhibiting different sizes and shapes from one another, either in a series of separate build cycles or in some cases within different processing regions of the same build cycle. The goal of flexibility and customization without tooling has led many of these systems to use large open beds, which further contribute to potential issues of waste or recycling of unbound powder when dealing with powder-liquid three-dimensional printing. These systems are not as well suited to the manufacturing of large numbers of identical parts, and it would be a substantial improvement in the field to provide an equipment assembly, system and method that is amenable to manufacturing of large numbers of identical parts while reducing or eliminating the need to waste or recycle unbound powder.

To date, there has been no disclosure of a system employing any type of compression during formation (during the print cycle of the process) of a three-dimensionally printed article. The only types of compression for 3DP articles have been cold isostatic pressing or uniaxial compression, in each case after formation of the article, meaning after the print cycle and drying cycle have been completed. Uniaxially compressed three-dimensionally printed dosage forms are known (U.S. Pat. Nos. 7,931,914, 8,758,658 and WO 2003/037607, which overcome certain disadvantages cited for cold isostatic pressing). They are made by first completing the three-dimensional printing part of the process, drying the dosage form and then uniaxially compressing the dosage form. If cold isostatic compression is used, a temporary elastomeric bag or mold is required for each article to be immersed in a confined liquid used to apply the pressure uniformly to all surfaces, after which the bag or mold is removed. In either case, such a system and process does not allow for the formation of three-dimensionally printed articles having controlled and varying void fraction among the individual layers of the printed articles, because compression is performed on the entire printed article. Such a system and process cannot form a three-dimensionally printed article comprising a more tightly compressed lower region (a higher density portion) and a more loosely compressed or even uncompressed upper region (a lower density portion). It would be a substantial improvement in the field to provide an equipment assembly, system and method for the preparation of three-dimensionally printed articles comprising upper and lower portions differing in density (or void fraction).

SUMMARY OF THE INVENTION

The present invention provides a manufacturing system and equipment assembly useful for the preparation of articles by three-dimensional printing. The system and assembly can be used for high through-put continuous, semi-continuous, or batch manufacture with minimal product loss, high efficiency, and high product reproducibility in the context of flexible article design.

The invention can provide a substantial reduction in or elimination of waste unbound powder as compared to other three-dimensional printing (3DP) processes. Cavity 3DP provides for most, substantially all or all of the solid material entering each cavity to be incorporated into a corresponding single 3DP article. The term cavity refers to the receptacle which receives the solid material. The receptacle can be part of a build module. In some embodiments, powdered solid material and liquid material are combined to form the article in the cavity.

In some aspects, the invention provides a three-dimensional printing equipment assembly (or apparatus) comprising:

a) a three-dimensional printing build system comprising:
at least one powder layering region (or system);
at least one binding fluid application region (or system); and
at least one powder receptacle movable between the regions, wherein the inner periphery of a top plan view of the powder receptacle approximates the outer periphery of a plan view of an article to be prepared with the build system.

Embodiments of the invention include those wherein: a) the equipment assembly comprises plural powder receptacles; b) the powder receptacles are arranged sequentially with respect to their direction of approach to the powder layering system; c) the powder receptacle is part of a build module; and/or d) a height adjustable platform is disposed within the receptacle.

In some aspects, the invention provides a three-dimensional printing equipment assembly (or apparatus) comprising:

a) a three-dimensional printing build system comprising:
at least one build module comprising at least one receptacle (cavity) that receives and temporarily retains powder from a powder layering system, wherein the receptacle has a top plan view periphery that approximates the periphery of a plan view of an article to be prepared with the equipment assembly; and
at least one build station comprising: 1) at least one powder layering system that deposits powder within the receptacle; and 2) at least one printing system that applies binding fluid at least to the periphery of powder layer(s) within proximity of the periphery of the receptacle.

In some embodiments, the equipment assembly (or apparatus) further comprises: a) a liquid removal system; b) a 3DP article dedusting system; c) a packaging system; e) a punch system; f) a punch system comprising at least one upper punch and at least one lower punch; g) a punch system comprising an upper punch having a bottom plan view with a periphery approximating the periphery of the receptacle; h) a lower punch having a top plan view with a periphery approximating the periphery of the receptacle; i) the punch further comprises a seal between the punch and the inner surface of the receptacle; j) a height adjustable platform in the receptacle and an upper punch; k) a height adjustable platform in the receptacle; l) a height adjustable platform in the receptacle, wherein the periphery of a top plan view of the platform approximates the inner periphery of the receptacle; m) an air relief means to release displaced air or equalize air pressure when an upper punch enters a cavity; n) a servo motor control on the upper punch, lower punch, or both; o) a positioning system on the upper punch, lower punch, or b both, in each case comprising a ball screw characterized by a lead accuracy V300p value that is less than or equal to about 50 microns, or less than or equal to about 20 microns, or less than or equal to about 10 microns, or less than or equal to about 5 microns.

In some embodiments, the periphery of the receptacle approximates the periphery of a plan view of a single article to be prepared. The periphery of the receptacle, the upper punch and the height adjustable platform approximates the periphery of a plan view of a single article to be prepared.

The invention also includes embodiments wherein: a) the receptacle has a top-plan view surface area approximating (within 20%, within 15%, within 10%, within 5%, within 1% or within 0.5% of) or the same as the plan view surface area of the article to be prepared; b) the receptacle has a top-plan view approximating or the same as a plan view of the article to be prepared; and/or c) the receptacle has a top-plan view periphery approximating or the same as a plan view periphery of the article to be prepared.

In some embodiments, the weight percentage of powder entering each cavity that is incorporated into a corresponding single final article is >80%, >90%, >95%, >98%, >99% or 100%. In some embodiments, the process is a zero-waste process in that solid material is neither recycled nor disposed of following completion of a build cycle.

During a 3DP build cycle using a cavity 3DP apparatus or equipment assembly, a layer of powder is placed within the cavity (receptacle), droplets of binding fluid are applied at or near the periphery of the powder to form an incremental layer having a top-plan view approximating the periphery of the cavity. A drying step is optionally conducted following the application step prior to placing another layer of powder in the cavity. Steps of the process are repeated to form plural incremental layers within the cavity. Following completion of the build cycle, the 3DP article is discharged from the cavity. The 3DP article is optionally dried, optionally dedusted, and/or optionally packaged.

In some aspects, the invention provides a method of preparing a three-dimensionally printed article, the method comprising:

forming a layer of powder within a receptacle, wherein the inner periphery of a top plan view of the receptacle approximates the outer periphery of a plan view of the article;

depositing binding fluid at or near the periphery of the powder layer within the receptacle to form an incremental layer defined by a print pattern, the outer periphery of which has a top-plan view approximating the inner periphery of the cavity.

Embodiments of the invention include those wherein: a) the process further comprises providing a receptacle, the top plan view of which is defined by an inner periphery that approximates the outer periphery of a plan view of the article; b) the process further comprises depositing binding fluid to the powder within the region defined by the print pattern; c) the powder has an average particle size, and the outer periphery of the print pattern in an incremental layer is spaced away from the inner periphery of the receptacle a distance that is 0.1, 0.5, 1, 2, 5, or 10-fold of the average particle size, or is selected from the ranges of 0.1- to 1-fold, 0.5 to 2-fold, 1- to 5-fold, or 5- to 10-fold of the average particle size; d) after the step of depositing, the incremental layer comprises a band of powder (unprinted powder, loose powder, unbound powder) that is 0.1, 0.5, 1, 2, 5, or 10-fold of the average particle size, or is selected from the ranges of 0.1- to 1-fold, 0.5 to 2-fold, 1- to 5-fold, or 5- to 10-fold of the average particle size, with the band situated between the inner periphery of the receptacle and the outer periphery of the print pattern; e) the forming and depositing steps are repeated to form the 3DP article; f) the outer periphery of print pattern in an incremental layer encloses an area comprising printed powder, unprinted powder or a combination thereof; f) the plan view of the article is a side plan view, top plan view, bottom plan view or a silhouette of a perspective view of the article; g) the outer periphery of the print pattern of an incremental layer is adjacent the inner periphery of the receptacle; h) a combination of any of the above.

In some embodiments: a) the periphery of the receptacle (cavity) is not shaped as a square, or rectangle, or star (e.g., 5-pointed star), or other shape with a plurality of sharp, thin edges, corners, or protrusions that extend away from the center of receptacle (cavity); b) the periphery of the receptacle comprises a geometric shape, non-geometric shape or combination thereof; c) a single article is formed within each receptacle; d) the print pattern is for an incremental layer of a single article; e) no unprinted (unbound) powder remains in the receptacle; f) unprinted powder remains within the area of an incremental layer defined by the outer periphery of the print pattern; g) one or more incremental layers are formed by depositing binding fluid more than once to a layer of powder; h) the rate of application or deposition (mL/cm$^2$ or mL/min or mL/sec) of binding fluid is the same across all incremental layers; i) the rate of application or deposition of binding fluid is different between at least two incremental layers of a 3DP article; j) each incremental layer is formed by depositing binding fluid only once to its respective layer of powder; k) one or more cavities can be characterized as have a longest linear dimension, and the longest linear dimension of a cavity, or of each cavity, is less than or equal to 12 inches, 6 inches, 3 inches, 2 inches, or 1 inch in length; l) the cavities are housed within, or defined by, or housed within and defined by openings within a turret member; m) the process is characterized by continuous motion of one or more cavities during the spreading and printing steps; n) the process is characterized by stopping of one or more cavities to allow for optional translating, compressing, marking or shaping the one or more incremental printed layers using the upper punch.

In some aspects, the invention provides a method of preparing a three-dimensionally printed article, the method comprising:

a) forming one or more layers of powder within a receptacle comprising a lower height adjustable platform (or punch), wherein the inner periphery of a top plan view of the receptacle and the outer periphery of a top plan view of the platform (or punch) approximates the outer periphery of a plan view of the article;

b) depositing binding fluid at or near the periphery of the one or more powder layers within the receptacle to form one or more incremental printed layers defined by a print pattern, the outer periphery of which has a top-plan view approximating the inner periphery of the receptacle;

c) before completion of the 3DP article, translating, compressing, marking or shaping the one or more incremental printed layers in the receptacle with a punch system; and d) repeating steps a) and b), and optionally step c), to complete formation of the 3DP article.

In some aspects, the invention provides a method of preparing a three-dimensionally printed article, the method comprising:

a) forming one or more layers of powder within a receptacle comprising a lower height adjustable platform (or punch);

b) according to a print pattern, depositing binding fluid onto the one or more powder layers to form a printed bed comprising loose unprinted powder and one or more incremental printed layers corresponding to one or more 3DP articles;

c) before completion of the one or more 3DP articles, translating, compressing, marking or shaping the one or more incremental printed layers in the receptacle with a punch system; and d) repeating steps a) and b), and optionally step c), to complete formation of the one or more 3DP articles.

Some embodiments of the invention include those wherein: 1) an additional step c) is performed between steps a) and b); 2) step c) is performed before step b); 3) the process further comprises a drying step after step b), such that the amount of binding fluid in the one or more incremental printed layers is reduced prior to conducting step c); 4) steps a) and b) are repeated and step c) is conducted at least once during preparation of a 3DP article; 5) steps a), b)

and c) are each repeated at least once during preparation of a 3DP article; 6) the minimal sequence of steps in the process is: i) step a), step b), drying, step c) and step d); ii) step a), step c), step b), drying, step c), and step d); and/or 7) step c) is performed while the receptacle is stationary.

The punch system can comprise an upper punch disposed above the height adjustable platform (or above a lower punch) such that the incremental printed layer(s) is(are) between the two. The translating step can be conducted by lowering the platform the same (or approximately or about the same) vertical distance as the upper punch. The compressing step can be conducted by: a) lowering the platform a first vertical distance and lowering the upper punch a second vertical distance, which is greater than the first vertical distance; b) first, lowering the upper punch and second lowering the platform; c) maintaining the upper punch at a position and raising the platform; d) lowering the upper punch and raising the platform; or e) first, raising the platform and second raising the upper punch.

The invention also provides three-dimensionally printed (3DP) articles having regions (comprising one or more incremental printed layers) that differ in void fraction (density), wherein at least one region has been compressed and another region has not been compressed. The 3DP article comprises plural incremental printed layers, wherein at least one incremental printed layer is compressed. In some embodiments, the 3DP article comprises plural incremental printed layers, wherein at least one incremental printed layer is a compressed layer and at least one incremental printed layer is an uncompressed (non-compressed) layer. The compressed layer can have a lower void fraction and higher density than the uncompressed layer. In some embodiments, the 3DP article comprises plural compressed incremental printed layers and at least one uncompressed incremental printed layer. In some embodiments, the 3DP article comprises plural compressed incremental printed layers and plural uncompressed incremental printed layers.

In some embodiments, the compressed layer is uniformly compressed, and in some embodiments the layer is non-uniformly compressed. The invention provides a 3DP article comprising at least one uniformly compressed incremental layer and at least one non-uniformly compressed incremental layer. In some embodiments, the invention excludes a 3DP article that has been compressed solely by uniaxial compression following completion of a build cycle (formation of all incremental layers) or following drying of the article. The at least one compressed incremental printed layer is formed during a build lap before completion of a build cycle.

The invention provides a process, equipment assembly/apparatus for preparing a 3DP article comprising at least one compressed, marked or shaped incremental printed layer. The process comprises compressing, marking and/or shaping one or more incremental printed layers during formation (during the build cycle) of the 3DP article. A 3DP article comprising at least one compressed, marked and/or shaped region can be made by a process comprising: a) forming an incremental printed layer; and b) compressing, marking and/or shaping the incremental printed layer with a punch system prior to completion of formation (printing) of the 3DP article. The process can further comprise: forming another incremental printed layer before step a) or after step b). In some embodiments, the compressing, marking and/or shaping step is conducted on each incremental printed layer of a 3DP article or on at least one but less than all of the incremental printed layers of a 3DP article.

The invention also includes a three-dimensionally printed (3DP) article comprising at least two incremental printed layers, wherein: at least one printed incremental layer comprises a first region and a horizontally adjacent second region; the first region is prepared from a first bulk powder and first binding fluid; the second region is prepared from a second bulk powder and second binding fluid; and the first bulk powder is different from the second bulk powder. The first binding fluid and the second binding fluid can be the same or different. The first binding fluid and the second binding fluid can have different compositions. The first bulk powder and the second bulk powder can have the same or different compositions.

In some embodiments, the process comprises: forming a powder layer in a cavity; depositing or printing liquid onto the powder layer in the cavity to form an incremental printed layer; and translating, compressing, marking and/or shaping the powder layer and/or incremental printed layer. In some embodiments, the process comprises: forming a powder layer in a cavity; depositing or printing liquid onto the powder layer in the cavity to form a incremental printed layer; forming another powder layer in the cavity; and simultaneously translating, compressing, marking and/or shaping the powder layer and incremental printed layer. The process can further comprise drying the incremental printed layer before or after translating, compressing, marking and/or shaping. The steps are repeated as needed to form a 3DP article comprising a full complement of incremental printed layers required to complete its structure.

In some embodiments, the invention excludes a process wherein a three-dimensionally printed article has been compressed solely by uniaxial compression following completion of a build cycle, following completion of formation (printing) of the article or following drying of the article.

The invention also provides a 3DP equipment assembly (or apparatus) and process for translating, compressing, marking and/or shaping one or more incremental layers after formation thereof but before completion of a build cycle, which forms one or more 3DP articles. In some aspects, the 3DP equipment assembly (or apparatus) comprises:
at least one powder layering region (or system);
at least one binding fluid application region (or system);
at least one punch region (or system); and
at least one powder receptacle movable between the regions.

The equipment assembly (or apparatus) can further comprise a drying region (or system) and a discharge (article transfer) region (or system).

The powder receptacle receives a powder when in the powder layering region to form a powder layer in the receptacle. Binding fluid is applied to the powder layer when the receptacle is in the binding fluid application region to form an incremental printed layer in the receptacle. Material (either powder layer or incremental printed layer) in the receptacle is punched in the punch region, wherein the punching may result in translating, compressing, marking and/or shaping of the powder layer or incremental printed layer depending upon how the punch is conducted. In some embodiments, one or more incremental printed layers are translated, compressed, marked and/or shaped in the punch region. In some embodiments, one or more incremental printed layers are not compressed in the punch region. In some embodiments, one or more incremental printed layers are translated, compressed, marked and/or shaped in the punch region, and one or more incremental layers are not translated, compressed, marked and/or shaped in the punch region.

The receptacle is movable between the regions (systems) in any order. In some embodiments, the receptacle moves: a) from the powder layering region to the binding fluid application region and then to the punch region; b) from the powder layering region to the punch region and then to the binding fluid application region; c) from the powder layering region to the binding fluid application region then back to the powder layering region and then to the punch region; or d) from the powder layering region to the binding fluid application region to the drying region and then to the punch region. The discharge region can be placed after the powder layering region, the binding fluid application region, the drying region or the punch region.

In some aspects, the invention provides a three-dimensional printing equipment assembly/apparatus comprising:
a) a three-dimensional printing build system comprising:
at least one build module comprising a powder receptacle and a height adjustable platform (or punch) disposed within the receptacle;
at least one power layering system for forming a powder layer by depositing powder within the receptacle;
at least one binding fluid deposition system for depositing binding fluid to the powder layer to form an incremental printed layer; and
at least one punch system for translating, compressing, marking or shaping a powder layer or incremental printed layer within the receptacle.

The build system can further comprise a layer drying system for in-process drying of an incremental printed layer after formation thereof. The equipment assembly/apparatus can further comprise an article drying system for drying of 3DP articles after completion of formation thereof.

The punch system is used to translate, compress, mark and/or shape at least one in-process incremental printed layer. The punch system can be used to create a vertical space in the receptacle for receipt of the next powder layer. In some embodiments, the punch system affects a non-compressive vertical translational of the contents of the receptacle. In some embodiments, the punch system affects a compression of the contents of the receptacle. In other words, punching may or may not cause compression of powder layer(s) and/or incremental layer(s) in the receptacle. In some embodiments, punching causes little compression or no compression of the material present in the receptacle (cavity) at the time of tamping, meaning that punching does not compress an incremental layer or a powder layer in the receptacle. In some embodiments, the punching step is affected by first dropping the bottom of (the surface of a height adjustable platform within) the receptacle and then lowering a punch into the receptacle. Here, the material in the receptacle may or may not be compressed. If the distance by which the upper punch is lowered into the receptacle is greater than the distance by which the bottom of the receptacle is lowered, then the material would be compressed. If the distance by which the upper punch is lowered into the receptacle is greater than the total of the distance by which the bottom of the receptacle is lowered and the thickness of a powder layer added to (or of the incremental layer within) the receptacle, then the material would be compressed. If the distance by which the upper punch is lowered into the receptacle is less than the total of the distance by which the bottom of the receptacle is lowered and the thickness of a powder layer added to (or of the incremental layer within) the receptacle, then the material would not be compressed.

In some embodiments, the platform (or lower punch) is lowered at the same time as the upper punch. In some embodiments, the platform (or lower punch) is lowered after a lag time relative to when the upper punch is lowered. In some embodiments, the upper punch is lowered after a lag time relative to when the platform (or lower punch) is lowered. In other embodiments, punch step is affected by first lowering the upper punch into the receptacle and then dropping platform in the receptacle, thereby compressing the powder layer or incremental layer in the receptacle. In some embodiments, the lag time may be less than 1.0 seconds, or 0.5 seconds, or 0.25 seconds, or 0.1 seconds, or 0.05 seconds.

Embodiments of the invention include those wherein: a) the equipment assembly (or apparatus) further comprises a conveyor system adapted to conduct plural build modules; b) the conveyor system repeatedly transports the build modules between the at least one powder layering system and the at least one printing system to form at least one article within a build module; c) the equipment assembly further comprises at least one liquid removal system (article drying system) that receives one or more 3DP articles and removes liquid there from; d) the build system further comprises at least one liquid removal system (layer drying system) that removes liquid from one or more incremental layers prior to completion of a build cycle, i.e. between formation of incremental layers; e) the conveyor system repeatedly transports the build modules between the at least one powder layering system, the at least one printing system and the at least one punch system to form at least one article within a build module; f) the conveyor system repeatedly transports the build modules between the at least one powder layering system, the at least one printing system, the at least one layer drying system and the at least one punch system to form at least one article within a build module.

In some embodiments, a build module comprises at least one receptacle (cavity) and an incrementally height adjustable platform (lower punch) disposed therein. The receptacle and platform receive and temporarily retain at least one incremental powder layer or plural stacked incremental powder layers. In some embodiments, the build module comprises plural receptacles and plural respective incrementally height adjustable platforms (lower punches). In some embodiments, a build module comprises a body comprising an upper surface with a cavity, a height adjustable build platform disposed within the cavity, height adjuster engaged with the body and the platform, and engagement means. In some embodiments, the platform is adapted to lower (recess) and/or raise by one or more increments before or after formation of an incremental printed layer thereon. The platform displacement can occur prior to or after placement of a subsequent incremental layer of powder thereon, thereby press-rolling or removing a portion of powder from a powder layer that has already been laid down. In some embodiments, the size of an increment is predetermined.

In some embodiments, engagement means removably engage a build module with the conveyor system. In some embodiments, plural build modules are removably engaged with a conveyor system. In some embodiments, the build module comprises one or more sidewalls surrounding the cavity and being adapted to retain powder on the height adjustable platform.

The system comprises a conveyor that transports one or more build modules along a path through the regions of a 3DP build system. In some embodiments, the path is a circuitous path, a horizontal circuitous path, a vertical circuitous path, or a combination thereof. In some embodiments, the path is circular, ellipsoidal, oval, rectangular, semicircular, square, triangular, pentagonal, hexagonal, octagon, oval, polygonal, parallelogram, quadrilateral, geometric, symmetrical, asymmetrical, or equivalents thereof with rounded corners and/or edges. The conveyor can be a staged conveyor, turret, belt conveyor, wheel conveyor, roller conveyor, chain conveyor, wire mesh conveyor, plate conveyor, slat conveyor, magnetic conveyor, bucket conveyor, cart-on-track conveyor, or other means for conducting solid articles along a process stream. The conveyor can be passive or powered. The conveyor can be troughed, cleated or flat.

In some embodiments, the conveyor system is a modular conveyor system comprising plural conveyor modules. The conveyor system can comprise at least one drive motor, at least one positioning controller, and a path along which plural build modules are conducted. In some embodiments, a conveyor module comprises a body, one or more build module engagement means, and conveyor module engagement means by way of which plural conveyor modules are adapted to engage to form a modular conveyor. In some embodiments, the conveyor system comprises plural attachments adapted to removably retain the plural build modules. In some embodiments, the attachment comprises plural one or more metal links with cam followers or comprises wheels, plates and/or bearings attached to a build module and mounted on a rail system upon which the build module is conducted. In some embodiments, the conveyor system further comprises one or more positioning-controllers. In some embodiments, the conveyor system is a continuous or discontinuous loop system. In some embodiments, the conveyor and plural build modules are present as a combination.

In some embodiments, the at least one build station is incrementally height adjustable with respect to the build modules, whereby the vertical space between the build module and the build station can be adjusted by one or more increments. In some embodiments, an incrementally height adjustable build station is adapted to raise by one or more increments after placement of a layer of powder on a build module and prior to placement of a subsequent layer of powder the build module. In some embodiments, a change in height is achieved by changing vertical position with respect to a prior position of the platform or with respect to an absolute position of the platform relative to the build module. In some embodiments, the build station is vertically fixed with respect to the build modules and a build platform within a build module is vertically height adjustable with respect to the build module so that the vertical distance between the build station and the build module remains the same during a print lap or print cycle.

In some embodiments, the size of the increment is the same for each incremental layer of a build cycle, is different for one or more incremental layers of a build cycle or a combination thereof. A build cycle comprises one or more build laps or plural build laps and is defined as the sum total of build laps required to form a 3DP article. A build lap is defined as the process of forming a printed incremental layer, i.e. placing an incremental layer of powdered build material and depositing (printing) liquid upon it. Accordingly, a build cycle results in the formation of plural stacked printed incremental layers that adhere to one another to together form a three-dimensionally printed article.

In some embodiments, the at least one powder layering system comprises at least one powder fill head. In some the embodiments, the powder fill head does not move either longitudinally or transversely with respect to the plane of the upper surface of a build module when applying an incremental layer of powder onto the build module. In some embodiments, a powder fill head comprises at least one powder fill head body, at least one powder spreader, and optionally at least one powder-height controller. In some embodiments, a powder layering system comprises a powder fill head, at least one powder reservoir and a powder feeder tube adapted to transfer powder from the powder reservoir to the powder fill head. In some embodiments, the powder spreader is a cylindrical roller, bar, rod, plate, paddle wheel, slotted wheel, spoked wheel disc, or straight smooth edge. In some embodiments, the powder fill head comprises a hopper or chute. In some embodiments, the powder spreader is a cylindrical roller the axis of which has or defines a radial direction of motion opposite the linear direction of motion of a build module through the powder layering system.

In some embodiments, the at least one printing system applies (deposits) liquid to the powder according to a Cartesian coordinate algorithm and/or a polar (radial) coordinate algorithm (cylindrical coordinate system, circular coordinate system, or spherical coordinate system). In some embodiments, the printing system comprises at least one print head and at least one liquid feed system. A print head can comprise one or more print modules or plural print modules.

In some embodiments, the invention excludes an equipment assembly or a method wherein the powder fill head moves laterally or transversely or is not stationary, with respect to a build module, while depositing an incremental powder layer. In some embodiments, the invention excludes an equipment assembly or a method wherein the print head moves laterally or transversely or is not stationary, with respect to a build module, while applying liquid to an incremental powder layer. In some embodiments, both the print head and the powder fill head are stationary during formation of a printed incremental layer or are stationary as otherwise described herein.

In some embodiments, the at least one printing system applies (deposits) liquid as a three-dimensional pattern of droplets or as plural two-dimensional patterns of droplets defining one or more articles. In some embodiments, the pattern comprises droplets placed at equal spacing within one or more articles. In some embodiments, this pattern comprises droplets placed at unequal spacing within one or more articles. In some embodiments, this pattern comprises droplets with different spacing within different regions of an article. In some embodiments, this pattern comprises droplets with tighter spacing (i.e., higher print density) in a region defining the exterior of an article. In some embodiments, this pattern comprises droplets with looser spacing (i.e., lower print density) in a region interior to an article. In some embodiments, more than one pattern is used.

In some embodiments, more than one powder (bulk powder) is used. In some embodiments, more than one liquid (binding fluid) is used. In some embodiments, the liquid comprises a pure solvent, blend of solvents, solution, suspension, colloid, emulsion, melt or a combination thereof. The binding fluid can further comprise one or more binders and/or other excipient(s).

In some embodiments, the equipment assembly further comprises an article transfer system that transfers 3DP articles, one or more at a time, away from the three-dimensional printing build system. In some embodiments, the article transfer system transfers 3DP articles to one or more liquid removal systems and/or one or more harvesting systems. In some embodiments, the article transfer system is integrated with the conveyor system, the liquid removal system or both.

In some embodiments, the liquid removal system comprises at least one dryer. In some embodiments, the liquid removal system processes one, two or more 3DP articles at a time. In some embodiments, the liquid removal system processes one, two or more build modules at a time.

In some embodiments, the equipment assembly comprises one or more harvesting systems that separates bulk loose powder from one or more 3DP articles. In some embodiments, the harvesting system processes articles already processed by the liquid removal system. In some embodiments, the harvesting system comprises loose powder collector and three-dimensionally printed article collector. In some embodiments, the harvesting system comprises a vibrating or orbiting surface adapted to receive the three-dimensionally printed article(s). In some embodiments, the harvesting system comprises a vacuum conveyor with a screen to separate articles from loose powder. The vibrating surface can be perforated, non-perforated, corrugated, smooth or non-smooth to permit separation of loose powder from the printed articles. Some embodiments of the invention exclude a harvesting system.

In some embodiments, the equipment assembly further comprises a dedusting system that removes loose particles from printed articles. A dedusting system can comprise a housing defining a dedusting region, one or more air jets, e.g. one or more air knives, that direct pressurized air into the dedusting region, one or more surfaces or retainers in the dedusting region for temporarily retaining one or more printed articles being dedusted, and one or more outlets through which air and removed particles exit the housing or dedusting region.

In some embodiments, the equipment assembly further comprises one or more powder recovery systems that collect powder from the one or more systems of the equipment assembly and return it to a powder reservoir. The recovery system can comprise one or more loose powder collectors and one or more conduits for conducting loose powder from the one or more collectors to a powder reservoir. The recovery system can further comprise: a) one or more powder mixers for mixing recovered loose powder with virgin loose powder; b) one or more pressurized air powder handling systems that facilitate transfer of loose powder from one location to another; c) one or more vacuum powder handling systems that facilitate transfer of loose powder from one location to another; d) one or more mechanical powder handling systems that transfer loose powder from one location to another; e) one or more manual powder handling systems that transfer loose powder from one location to another; or f) a combination thereof.

In some embodiments, the 3DP equipment assembly excludes a powder recovery system that collects powder from the one or more systems of the equipment assembly and returns it to a powder reservoir. In some embodiments, the 3DP equipment assembly excludes a powder recovery system that collects powder from a printed bed comprising plural 3DP articles and loose (unbound, unprinted) powder.

In some embodiments, the equipment assembly further comprises a control system comprising one or more computerized controllers, one or more computers, and one or more user interfaces for one or more computers. In some embodiments, one or more components of the equipment assembly are computer controlled. In some embodiments, one or more components of the 3DP build system are computer controlled. In some embodiments, the conveyor system, the height adjustable platforms of the build modules, the at least one powder layering system, the at least one punch system, the at least one drying system and/or the at least one printing system are computer controlled.

In some embodiments, the equipment assembly spreads layers of powder and deposits (print) droplets of liquid in a predetermined pattern on to the layers according to instructions provided by a computerized controller. In some embodiments, the predetermined pattern is based on one or more two-dimensional image files comprising pixels. In some embodiments, the two-dimensional image files are structured such that certain pixels indicate dispensing of droplets, and other pixels represent no dispensing of droplets. In some embodiments, the two-dimensional image files include different colors of pixels to indicate dispensing of different liquids, or no dispensing of liquid. In some embodiments, the predetermined pattern for applying the liquid is the same in each incremental layer, is the same in two or more incremental layers, is different in one or more incremental layers, is different in all incremental layers, or is the same for a first group of incremental layer and the same for a second group of incremental layers but the pattern for the first group is different than the pattern for the second group.

In some embodiments, the equipment assembly further comprises one or more working surfaces, frames, supports, tables, gantries, enclosures, turrets and/or platforms.

The invention also provides a three-dimensional printing equipment assembly comprising:
a) a three-dimensional printing build system comprising:
a conveyor system that conducts plural build modules and comprises positioning-controller and plural build module engagements;
plural build modules engaged with the conveyor system, wherein the build modules receive and temporarily retain powder from a powder layering system, and wherein a build module comprises: 1) one or more sidewalls defining a cavity; and 2) an incrementally height adjustable platform (punch) disposed within the cavity;
at least one build station comprising: 1) at least one powder layering system that forms incremental powder layers within the cavity and comprises at least one powder fill head, at least one powder spreader and at least one powder reservoir; and 2) at least one printing system that applies a liquid according to at least one predetermined pattern to the incremental powder layers and comprises at least one liquid feed system and at least one print head that deposits liquid according to the at least one predetermined pattern;
at least one punch system comprising at least one upper punch;
wherein the conveyor system repeatedly transports the plural build modules from the at least one powder layering system to the at least one printing system,
whereby the three-dimensional printing build system: 1) forms at least one incremental printed layer per build lap in a build module; 2) forms a single 3DP article per build cycle in a build module; 3) forms plural 3DP articles per build cycle in a build module; or 4) forms a 3DP bed comprising one or more three-dimensionally printed articles and, optionally, loose (unbound or only partially bound) powder that has not been printed upon per build cycle in a build module;
b) optionally, at least one harvesting system that separates loose powder from: 1) one or more incremental printed layers; 2) one or more 3DP articles; or 3) one or more 3DP beds; and
c) optionally, at least one liquid removal system that removes liquid from: 1) one or more incremental printed layers of an in-process incompletely formed 3DP article; 2) one or more 3DP articles after printing thereof; or 3) one or more 3DP beds.

Some embodiments of the invention include those wherein: 1) at least one liquid removal system is present; 2) the equipment assembly further comprises at least one packaging system that packages one or more three-dimensionally printed articles; 3) the conveyor system repeatedly transports plural build modules from the at least one powder layering system to the at least one printing system in a linear manner thereby facilitating Cartesian coordinate printing or in a radial manner thereby facilitating polar coordinate printing; 4) the equipment assembly further comprises a powder recovery system for recovering, and optionally recycling, unprinted powder; 5) the equipment assembly further comprises a liquid detector; 6) a liquid detector detects the presence of liquid in one or more printed incremental layers and/or in one or more printed articles; 7) the equipment assembly further comprises an inspection system; 8) an inspection system is a printed powder inspection system that determines the integrity of printing in one or more incremental printed layers and/or one or more printed articles and/or determines whether or not powder was properly applied in one or more incremental layers; 9) determining the integrity of printing comprises at least one of determining whether or not liquid has been correctly applied to one or more incremental layers according to one or more predetermined patterns and/or determining whether or not liquid has been correctly applied to one or more incremental layers according to a predetermined amount; 10) the inspection system is a printed article inspection system that determines whether or not one or more printed articles have the correct size, shape, weight, appearance, density, content and/or color; 11) the inspection system is a liquid application inspection system that monitors droplets of liquid applied by the print head to powder; 12) the inspection system comprises one or more cameras; 13) a camera is independently selected at each occurrence from the group consisting of a visible wavelength camera, an UV wavelength camera, a near infrared wavelength camera, an x-ray camera and an infrared wavelength camera; and/or 14) the equipment assembly excludes a powder recovery system for recovering and recycling unprinted powder.

The invention includes all combinations of the embodiments, subembodiments and aspects disclosed herein. Accordingly, the invention includes the embodiments and aspects specifically disclosed, broadly disclosed, or narrowly disclosed herein, as well as combinations thereof and subcombinations of the individual elements of said embodiments and aspects. The invention can be a combination of two or more elements described herein or specified in the claims. The invention is substantially as described herein. In some embodiments, the invention is substantially as described in one or more drawings.

Other features, advantages and embodiments of the invention will become apparent to those skilled in the art by the following description, accompanying examples.

BRIEF DESCRIPTION OF THE FIGURES

The following figures form part of the present description and describe exemplary embodiments of the claimed invention. These drawings are not necessarily drawn to scale, and are instead intended to illustrate the general principles of the invention as further described herein. Although specific embodiments are described below with specific reference to the drawings provided, other embodiments are possible without deviating from the spirit and scope of the present invention. The skilled artisan will, in light of these figures and the description herein, be able to practice the invention without undue experimentation.

FIGS. 1A-1D depict top plan views of prior art open-bed build modules of a three-dimensional printing equipment assembly of U.S. Pat. No. 8,888,480, wherein plural articles are printed in a single bed of loose powder.

FIGS. 9A-9I depict partial sectional side elevation views of an exemplary punch system, exemplary powder layering system and exemplary liquid deposition (printing) system during in-process use for the preparation of an uncompressed 3DP article in a cavity.

FIGS. 10A-10C depict partial sectional side elevation views of an exemplary punch system during in-process use for the preparation of a compressed 3DP article in a cavity.

FIGS. 11A-11E depict partial sectional side elevation views of four different exemplary punch systems during in-process use for the preparation of compressed 3DP articles in respective cavities.

FIGS. 12A and 12B depict partial sectional side elevation views of an exemplary punch system during in-process use for discharging a 3DP article from a cavity.

FIG. 13 depicts a perspective view of a prior art uniaxially compressed 3DP dosage form according to U.S. Pat. Nos. 7,931,914 and 8,758,658.

FIGS. 14A and 14B depict perspective views of exemplary 3DP articles of the invention comprising regions or incremental layers differing in porosity (density).

FIGS. 15A-15B depict cross-sectional side elevation views of exemplary 3DP articles of the invention.

FIG. 15C depicts a top plan view of an exemplary 3DP article of the invention.

FIG. 15D depicts a perspective view of an exemplary 3DP article of the invention.

FIG. 15E depicts a cross-sectional side view of an exemplary 3DP article of the invention.

FIG. 16 depicts a partial sectional side elevation view of an exemplary liquid removal system, lower punch and build module of the invention.

FIG. 17 depicts a partial sectional side elevation view of an exemplary liquid removal system, lower punch and build module of the invention.

FIG. 37 depicts a perspective view of an exemplary multi-cavity build module.

FIG. 38 depicts a side elevation view of an exemplary printing system.

FIG. 39 depicts a bottom perspective view of an exemplary layout of print modules in the print head of a printing system.

FIG. 40 depicts bottom plan views of alternate exemplary layouts for the print modules in different print heads.

FIG. 41 depicts a side elevation view of an exemplary powder layering system.

FIG. 42 depicts a perspective view of a powder layering system and multi-cavity build module during in-process use.

FIG. 43 depicts a partial top plan view of an exemplary multi-cavity build module and a build station comprising a powder layering system and a printing system.

FIGS. 44A-44D depict top plan views of various different embodiments of a print head and arrangements thereof.

FIG. 47 continues to FIG. 48, which continues to FIG. 49, which refers back to FIG. 47.

DETAILED DESCRIPTION OF THE INVENTION

Figure 2A:
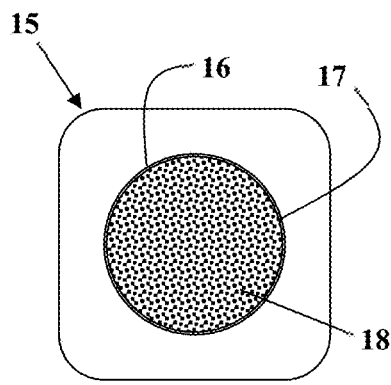
FIGS. 2A-2G depict top plan views of build modules of the invention.
Figure 2B:
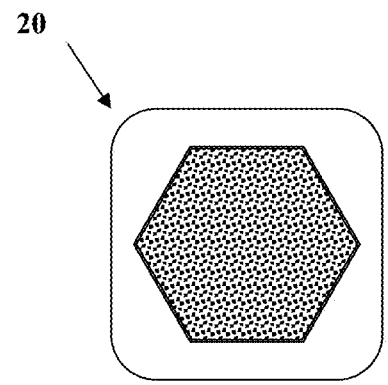
Figure 2C:
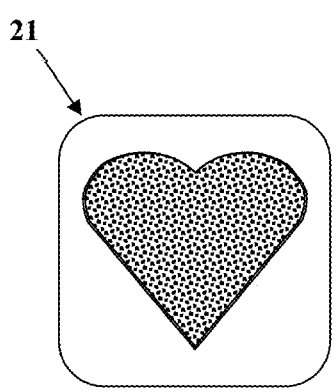

The invention provides an equipment assembly and system useful for the manufacture of articles via a three-dimensional printing process. The assembly and system are suitable for small scale/volume, medium scale/volume and large scale/volume preparation of articles. The three-dimensional printing (3DP) process comprises forming an incremental layer of powder on a surface and subsequently printing/applying a liquid onto the layer, then repeating the steps of forming and printing a sufficient number of times to form a 3DP article on the surface or form a printed powder bed comprising one or more 3DP articles and loose powder. Any excess/undesired liquid remaining in the article(s) is removed and the loose powder, if any, is separated from the article(s), which is(are) then collected.

As used herein, 3DP means three-dimensional printing, three-dimensionally printed or other such conjugation thereof. As used herein, "cavity three-dimensional printing" or "cavity 3DP" or "c3DP", means three-dimensional printing in which the layer-by-layer (incremental layer-by-incremental layer) assembly steps are carried out in one or more cavities that are sized to fit individual articles, with little or no unprinted powder surrounding each article (or incremental layer) within each cavity, or otherwise with a minimum of loose powder surrounding each article in each cavity. In other words, the cavity, which has a top-plan view defined by an interior periphery (edge), is charged with a layer of powder, and binding fluid is applied at least to the outer periphery of the layer of powder adjacent the inner periphery of the cavity to form an article such that only a minimal amount, if any, of unprinted powder remains between the cavity surface and the printed powder.

As used herein with regard to the invention, the term "tamping" is used interchangeably with the term "compressing", unless otherwise specified. Tamping is effected with the punch system, whereby one or more incremental layers or powders layers of an in-process 3DP article within a cavity is/are compressed. The punch system comprises an upper punch superposing a cavity and a lower punch or lower height adjustable platform disposed within a cavity. In some embodiments, the tamping is affected by: a) lowering the upper punch into the cavity before lowering the lower punch or platform in the cavity; b) lowering the upper punch into the cavity a greater distance than the lower punch or platform in the cavity is lowered; c) raising the lower punch or platform in a cavity before raising the upper punch in the cavity; or d) raising the lower punch or platform in a cavity a greater distance than the upper punch in the cavity is raised. A process of the invention can comprise one or more tamping steps.

As used herein, "translating" or "translation" (or other conjugation thereof) refers to the act or result of vertically (and linearly) displacing or moving one or more incremental layers within a cavity by use of the punch system. Translating and translation are considered non-compressive or essentially non-compressive actions, whereby a 3DP article or one or more layers in a cavity are pushed downward or upward by use of the punch system with essentially no change in the volume of the 3DP article. In some embodiments, the translation is affected by: a) lowering the upper punch and the lower punch or platform in a cavity the same or about the same distance; or b) raising the upper punch and the lower punch or platform in a cavity the same or about the same distance. In some embodiments the timing of the translation is effectuated by: a) lower and upper punch moving at approximately the same time; b) the lower punch moving before the upper punch, for a downward movement; c) the upper lunch moving before the lower punch, for an upward movement.

As used herein, "marking" refers to the act of forming at least one raised or lowered feature on the surface of an incremental layer (be it an incremental powder layer or incremental printed layer) such that the surface is no longer a strictly flat surface, meaning it is a non-flat surface. Marking is achieved by contacting the surface of the layer with a punch (or platform) such that an impression is made upon the surface. This meaning of marking is distinct from prior noncontact marking effectuated by 3DP ("noncontact 3DP marking"), such as the creation of recessed features via the exclusion of droplets in select exterior regions of an article, allowing the unbound powder to empty out. Such noncontact 3DP marking is discussed in U.S. Pat. No. 8,828,411. Such noncontact techniques for marking during 3DP may be considered option, either alone or in combination with the marking described herein.

As use herein in reference to an incremental layer, "shaping" refers to the act of altering the shape of one or more surfaces of an incremental layer or the shape of an entire layer such that the upper and lower surfaces of an incremental layer are not both flat parallel planes. Opposing surfaces of an incremental layer may or may not be flat, but they are not simultaneously flat and parallel planes. Both surfaces may be simultaneously flat, but they would also be non-parallel. A contoured, embossed or debossed surface is considered a non-flat surface. Shaping is achieved by contacting one or more surfaces of an incremental layer with a punch (or platform) such that the upper and lower surfaces of an incremental layer are not both flat parallel planes, and may include one or more of a contoured, an embossed, or a debossed surface.

A process of the invention can comprise one or more translating steps, one or more tamping (compressing) steps, one or more marking steps and/or one or more shaping steps.

Generally, a 3DP equipment assembly, apparatus or system comprises various subsystems including one or more three-dimensional printing build systems, one or more harvesting systems, and optionally one or more liquid removal systems. The equipment assembly can comprise one or more three-dimensional printing build systems, one or more harvesting systems, one or more liquid removal (drying) systems and optionally one or more other systems. In some embodiments, the equipment assembly further comprises one or more (sub)systems selected from the group consisting of one or more punch systems, one or more discharge systems, one or more powder recovery systems, one or more control systems, one or more build module or conveyor positioning systems, one or more conveyor drive motors, one or more article transfer systems, one or more inspection systems and one or more bed transfer systems. The 3DP equipment assembly, apparatus or system can comprise some or all of the above systems. For example, in certain embodiments of a cavity 3DP equipment assembly, apparatus, or system, it is not necessary to have a harvesting system since substantially all of the powder material entering a cavity is incorporated into a respective article formed within the cavity, with little or no excess powder for separation.

As used herein, a "three-dimensional printing build system" generally comprises a conveyor system, at least one build module, at least one build station, and optionally one or more other components. The function of the three-dimensional printing build system is to form one or more three-dimensionally printed articles from a multilayered bed of powder in a build module. In some embodiments, the 3DP build system forms a single 3DP article per build cycle in a cavity (receptacle). One or more, or plural, build modules are engaged with a conveyor system that is adapted to conduct the build module(s) along a predetermined path which passes through one or more build stations. A build module is conducted to a powder layering system (region), and an incremental powder layer is formed in the cavity. The build module is then conducted to a printing system (region), and a binding fluid is applied to the incremental powder layer according to a predetermined pattern thereby forming a partially or fully bound powder layer (an incremental printed layer).

The steps of conducting the build module, forming an incremental powder layer and applying a liquid to the layer to form an incremental printed layer are considered to be a single build lap of the process. Build laps are repeated such that an incremental printed layer from one lap adheres to a printed incremental layer from a prior or subsequent lap. Build laps are repeated in build modules a sufficient number of times to form single 3DP articles per cycle in build modules or to form a three-dimensionally printed bed comprising one or more three-dimensionally printed articles and loose powder, wherein the three-dimensionally printed article(s) comprise(s) at least two printed incremental layers.

The liquid applied to the powder may or may not dry sufficiently under ambient conditions between build laps; therefore, a liquid removal step can be included between build laps. In some embodiments, a dryer is present in the build station in order to dry in-process incremental layers after deposition of binding fluid. In such embodiments, a build lap would comprise the steps of conducting the build module, forming an incremental powder layer in the build module, applying a liquid to the powder layer to form an incremental printed layer, and exposing the printed layer to a dryer. If, however, the incremental layer does not dry sufficiently during build laps, then an optional liquid removal step can be conducted following completion of all the build laps, i.e. following completion of a build cycle, for a three-dimensionally printed article. In other words, a 3DP article that has completed a build cycle can be dried in an article dryer if needed.

The conveyor system is adapted to conduct one or more build modules through a predetermined course/path during and between build laps. Substantially any system useful for conveying solid materials from a first location to a second location and back to the first location can be used. In some embodiments, the conveyor system is a cyclic, linear, reciprocating or oscillating conveyor system. In some embodiments, the cyclic conveyor system conducts build modules from the first location to a second location and then back to the first location. In some embodiments, the conveyor system is a cyclic or iterative conveyor system that repeatedly conducts build modules through one or more build station(s). In some embodiments, the linear conveyor system conducts build modules from a first build station to a second build station and optionally one or more other build stations. In some embodiments, the oscillating system conducts one or more build modules through at least one build station in a first direction and then conducts the one or more build modules through the at least one build station in an opposite direction.

FIGS. 1A-1D depict top plan views of prior art open-bed build modules of a 3DP equipment assembly of U.S. Pat. No. 8,888,480, wherein plural articles are printed in a single bed of loose powder. The open bed system of FIG. 1A comprises a build module (1) having a single cavity (2) within which plural 3DP articles (3) are printed leaving behind a substantial amount of unprinted powder (4). The inner periphery (edge) defining the top plan view of the cavity is not shaped like the outer periphery of the 3DP articles in the printed powder bed. The open bed system of FIG. 1B is very similar to that of FIG. 1A. It comprises a build module (5) and a cavity (6) within which plural 3DP articles (7) are printed leaving behind a substantial amount of unprinted powder (8). The open bed build module (10) of FIG. 1C can be used to prepare multiple triangular 3DP articles; however, there is still a substantial amount of unprinted powder (11) that must be disposed of or recycled. The same is true of the build module (12) and unprinted powder (13) of FIG. 1D. Although FIG. 1C and FIG. 1D show much closer article-to-article spacing due to advantages in shape and packing, some unprinted powder is still required between articles to keep them from binding to one another. The print patterns for FIGS. 1A-1D differ but both leave behind a substantial amount of unprinted powder that must be separated from the articles and then recycled or disposed of. This is because the inner periphery of the top plan view of their respective cavities is not adjacent the outer periphery of the plan view of their respective 3DP articles. Thus prior art open bed systems have the key disadvantage of substantial waste of bulk powder or the requirement for disposal or recycle of substantial amounts of bulk powder. Another key disadvantage of open bed systems is that they do not permit recycling of and require disposal of the unprinted powder whenever two different bulk powders are used to form the layers, because the two different bulk powders become mixed during the harvesting step of the process. The key disadvantage is overcome with the cavity 3DP system of the invention, which is capable of printing 3DP articles comprising incremental layers made of different bulk powders while minimizing or eliminating the disposal of bulk powder.

The cavity 3DP system of the invention, however, is able to minimize and even eliminate the need to dispose of or recycle bulk powder. FIGS. 2A-2G depict top plan views of build modules and their respective cavities (receptacles) of the invention. The build module (15) of FIG. 2A comprises a cavity, the top plan view of which is defined by an inner periphery (edge, 17). A 3DP article (18) is printed within the cavity. The outer periphery of the plan view of the 3DP article (18) approximates the inner periphery of the top plan view of the cavity. During the build cycle, binding fluid is applied to outer periphery of respective powder layers such that the binding fluid is adjacent (or minimally spaced away from) the inner periphery of the cavity. As a result, little to no bulk powder needs be disposed of or recycled. The build module (20) of FIG. 2B operates in the same manner as that of FIG. 2A except that the cavity and print patter are hexagonally rather than circularly shaped. The build module (21) of FIG. 2C operates in the same manner as that of FIG. 2A except that the cavity and print patterns are heart-shaped rather than circularly shaped.

Figure 2D:
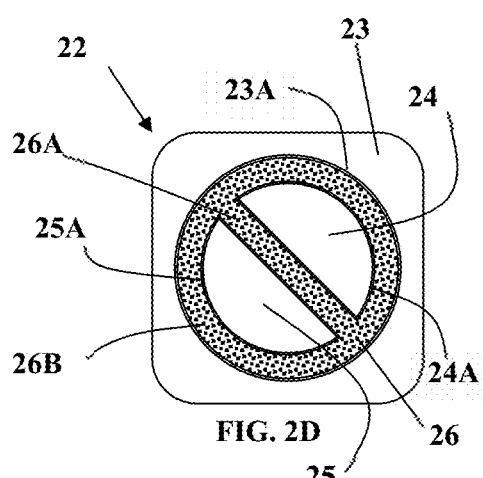

The build module (22) of FIG. 2D comprises a body (23) having an edge (23A) defining an outer periphery of the cavity. A height adjustable platform is disposed within the cavity and it has a top plan view that is shaped similar to the top plan view of the cavity. The build module also comprises stands (24, 25), which are not height adjustable and which are defined by respective edges (peripheries, 24A, 25A). As a result of this configuration, the 3DP article (26) comprises an annular portion (26B) and a connecting portion (26A). Accordingly, the cavity 3DP system of the invention can be used to prepare 3DP articles with sharper surface features than those of prior art 3DP systems (such as open bed 3DP systems) and can do so with a much higher incorporate rate of cavity powder into final article.

Figure 2E:
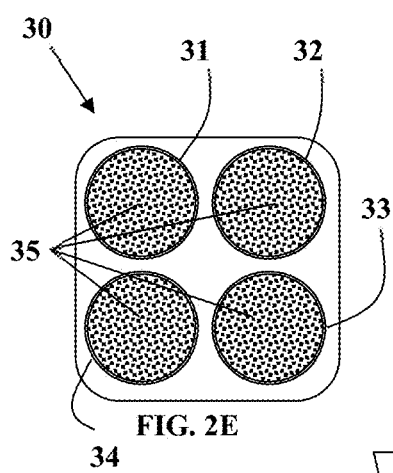
Figure 2F:
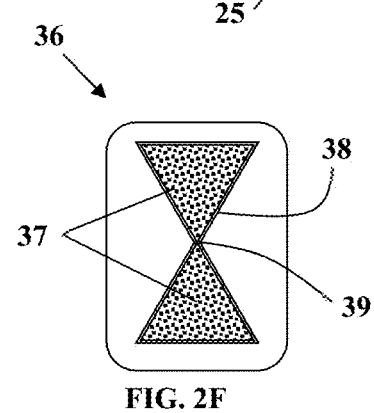

As an improved alternative to open bed systems, the build module (30) of FIG. 2E comprises plural cavities (receptacles, 31-34) within which respective single 3DP articles (35) are formed. A build module of the invention can comprise a body and plural cavities, the top plan view of each cavity being defined by an edge approximating the plan view of a 3DP article to be printed in the cavity, wherein the build module further comprises a height adjustable platform (or punch) in each build cavity, and the top plan view of the platform (or punch) approximates the top plan view of its respective cavity. The build module (36) of FIG. 2F is for an improved open bed system. The build module comprises a cavity the top plan view of which is defined by the edge (38), such that the edge (38) approximates the outer periphery of the plan view of articles (37) printed within the cavity. In the narrow example of FIG. 2F, opposing portions (39) of the edge (38) are very closely spaced or in contact with one another.

Figure 2G:
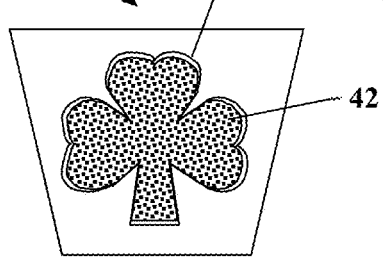

The build module (40) of FIG. 2G comprises a cavity having a top plan view defined by an edge (41) in the body of the build module. The shape of the outer periphery of the plan view of the article (42) approximates the shape of the edge (41).

The improved systems of FIGS. 2A-2G do not require disposal or recycle of large amounts of unprinted powder.

Figure 3:
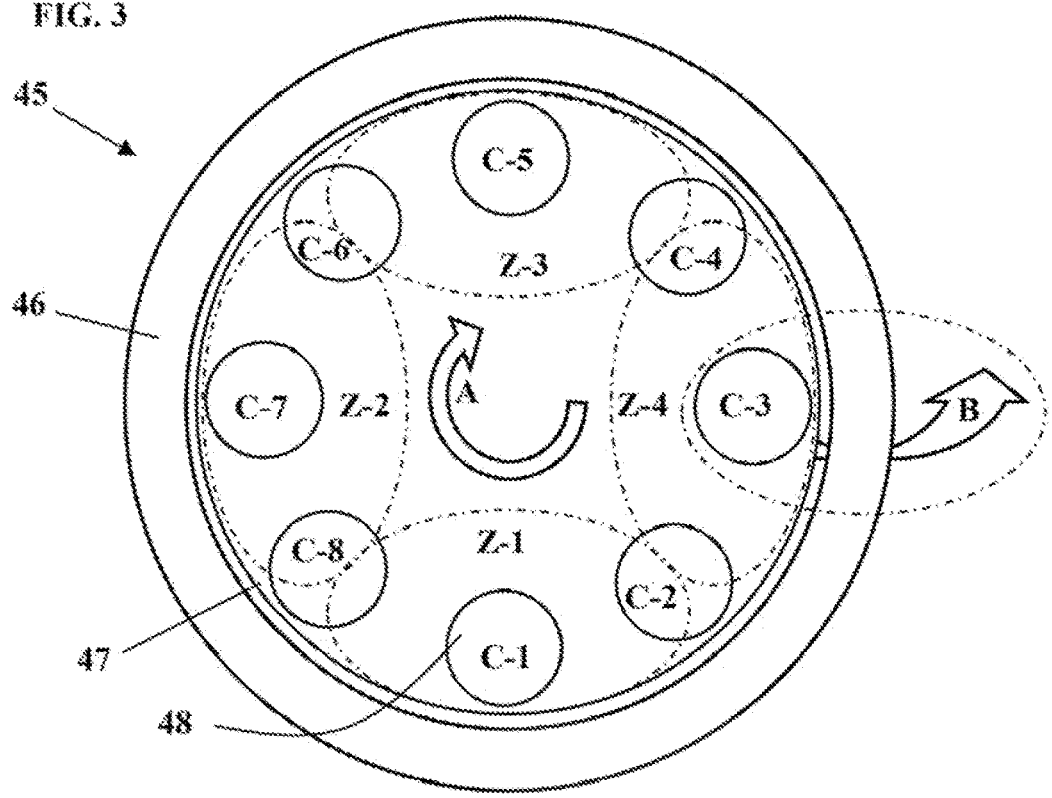
FIGS. 3 and 4 depict top plan views of exemplary three-dimensional printing equipment assemblies (or apparatuses) of the invention.

The 3DP equipment assembly (or apparatus) (45) of FIG. 3 comprises a powder layering region (Z-1), a printing region (Z-2), a liquid removal region (Z-3) and a punch region (Z-4). The assembly comprises a stationary body and a conveyor (47) which comprises plural build modules (48)

with respective cavities. The conveyor conducts the build modules in a circuitous path in the direction of Arrow (A) from region (Z-1) to region (Z-2) to region (Z-3) to region (Z-4) per build lap. The assembly also comprises a discharge region, substantially integral with the punch region, wherein the 3DP articles are discharged from their respective cavities.

Figure 4:
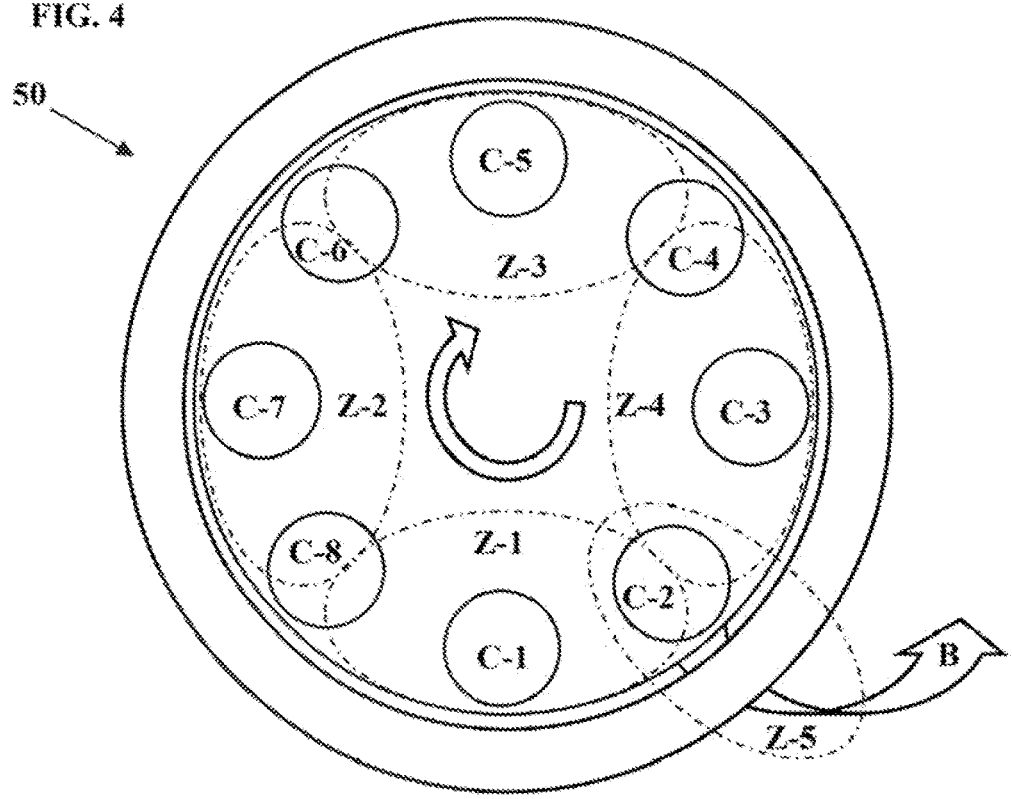

The 3DP equipment assembly (or apparatus) (50) of FIG. 4 is similar to that of FIG. 3, except that the discharge region (Z-5) is now separate from the punch region (Z-4). In this case, the assembly may comprise two (full or partial) punch systems. A full punch system comprises: a) an upper punch and a lower punch, optionally in a cavity; or b) an upper punch and a lower height adjustable platform in a cavity. A partial punch system comprises: a) an upper punch; b) a lower punch in a cavity; or c) a lower height adjustable platform in a cavity.

Figure 5A:
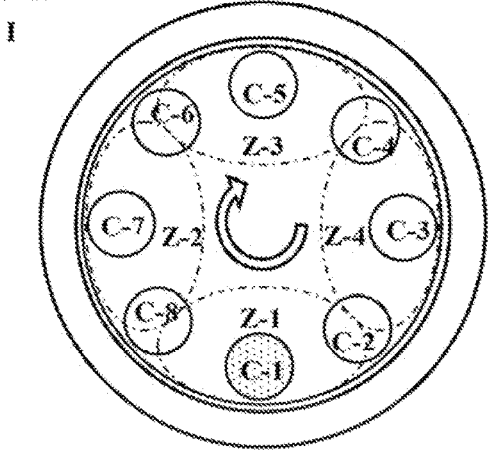
FIGS. 5A-5J depict top plan views of the exemplary three-dimensional printing equipment assembly (or apparatus) of FIG. 3 during in-process use for the preparation of single 3DP articles in cavities.
Figure 5B:
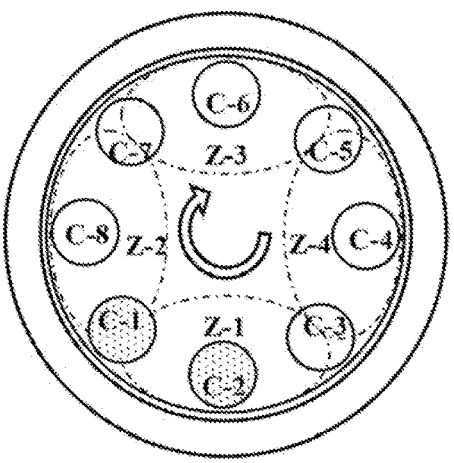
Figure 5D:
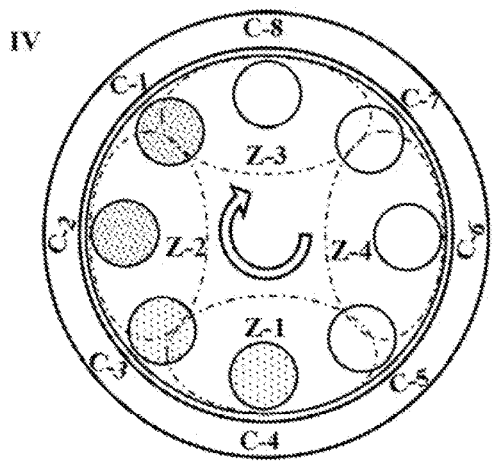
Figure 5C:
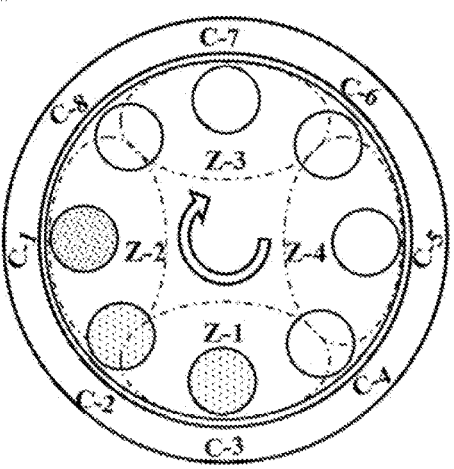
Figure 5E:
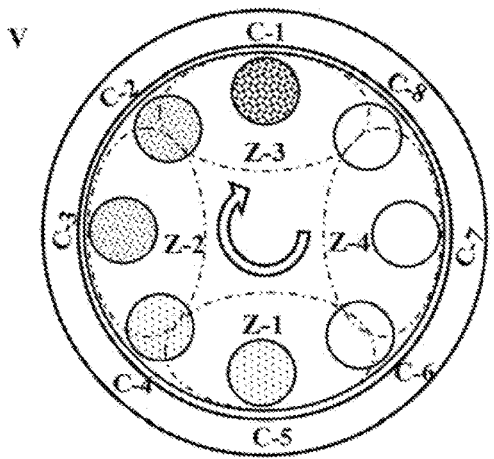
Figure 5F:
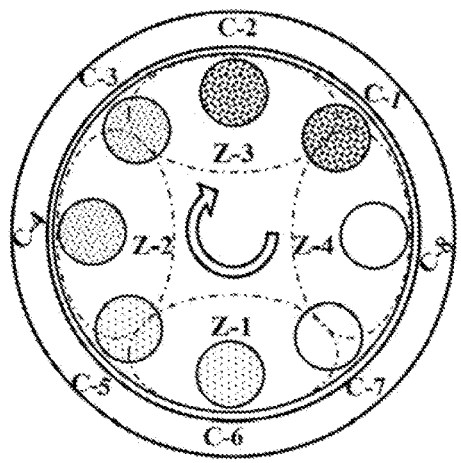
Figure 5G:
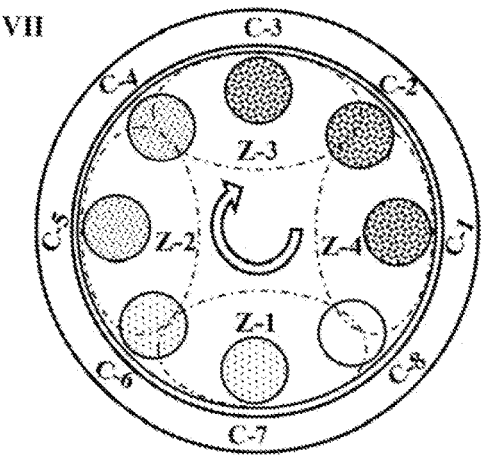
Figure 5H:
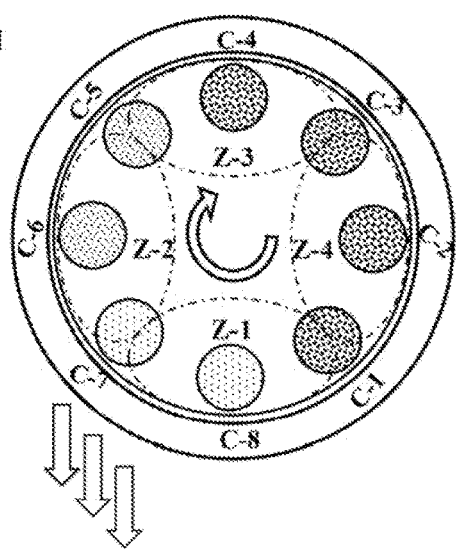
Figure 5J:
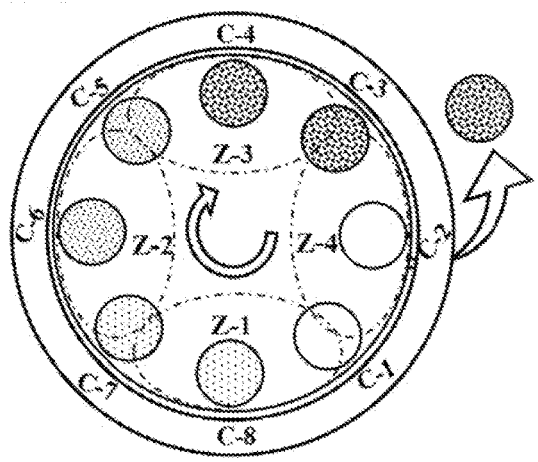
Figure 5I:
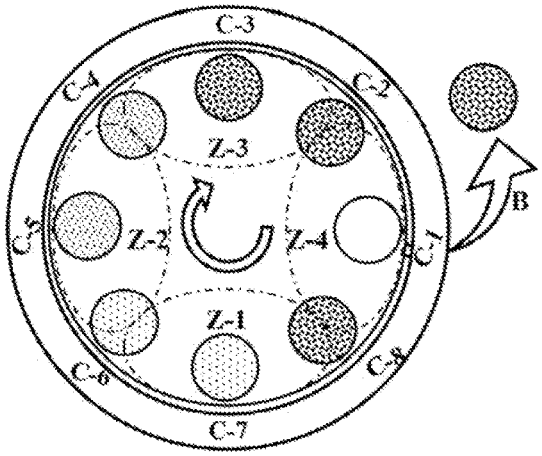

FIGS. 5A-5I depict top plan views of the exemplary three-dimensional printing equipment assembly (or apparatus) of FIG. 3 during in-process use for the preparation of single 3DP articles in respective cavities (C-1 through C-8). In FIG. 5A (phase I), a layer of powder is added to cavity (C-1) in the powder layering region (Z-1). The conveyor is advanced clockwise to place cavity (C-2) in the region (Z-1), whereby the cavity (C-2) receives its layer of powder and cavity (C-1) approaches the printing region (Z-2) (FIG. 5B, phase II). The conveyor is again advanced clockwise (FIG. 5C, phase III), whereby the cavity (C-3) receives its layer of powder, cavity (C-2) approaches the printing region (Z-2), and the layer in cavity (C-1) is printed upon. The conveyor is again advanced clockwise (FIG. 5D, phase IV), whereby the cavity (C-4) receives its layer of powder, cavity (C-3) approaches the printing region (Z-2), the layer in cavity (C-2) is printed upon and cavity (C-1) approaches the drying region (Z-3). The conveyor is again advanced clockwise (FIG. 5E, phase V), whereby the cavity (C-5) receives its layer of powder, cavity (C-4) approaches the printing region (Z-2), the layer in cavity (C-3) is printed upon, cavity (C-2) approaches the drying region (Z-3), and the printed layer in cavity (C-1) is dried. The conveyor is again advanced clockwise (FIG. 5F, phase VI), whereby the cavity (C-6) receives its layer of powder, cavity (C-5) approaches the printing region (Z-2), the layer in cavity (C-4) is printed upon, cavity (C-3) approaches the drying region (Z-3), the printed layer in cavity (C-2) is dried, and cavity (C-1) approaches the punch region (Z-4). The conveyor is again advanced clockwise (FIG. 5G, phase VII), whereby the cavity (C-7) receives its layer of powder, cavity (C-6) approaches the printing region (Z-2), the layer in cavity (C-5) is printed upon, cavity (C-4) approaches the drying region (Z-3), the printed layer in cavity (C-3) is dried, cavity (C-2) approaches the punch region (Z-4), and the incremental layer in cavity (C-1) is translated downward to create a space above it for receiving additional powder when in the powder layering region (Z-1). The conveyor is again advanced clockwise (FIG. 5H, phase VIII), whereby the cavity (C-8) receives its layer of powder, cavity (C-7) approaches the printing region (Z-2), the layer in cavity (C-6) is printed upon, cavity (C-5) approaches the drying region (Z-3), the printed layer in cavity (C-4) is dried, cavity (C-3) approaches the punch region (Z-4), the incremental layer in cavity (C-2) is translated downward, and cavity (C-1) approaches the powder layering region (Z-1). The above steps define a single build lap for this specific embodiment. The build lap is repeated as many times as required to form a 3DP article comprising plural printed incremental layers. After completion of a build cycle, each article is discharged from its respective cavity. For example, FIG. 5I depicts initiation of the discharge phase. Notice that in-process (incomplete) article of cavity (C-8) is approaching the powder layering region (Z-1) but the completed article in cavity (C-1) has been discharged. The conveyor is again advanced clockwise (FIG. 5J), whereby the empty cavity (C-1) approaches the powder layering region (Z-1) in preparation of receiving another layer of powder to initiate formation of another 3DP article.

Figure 6:
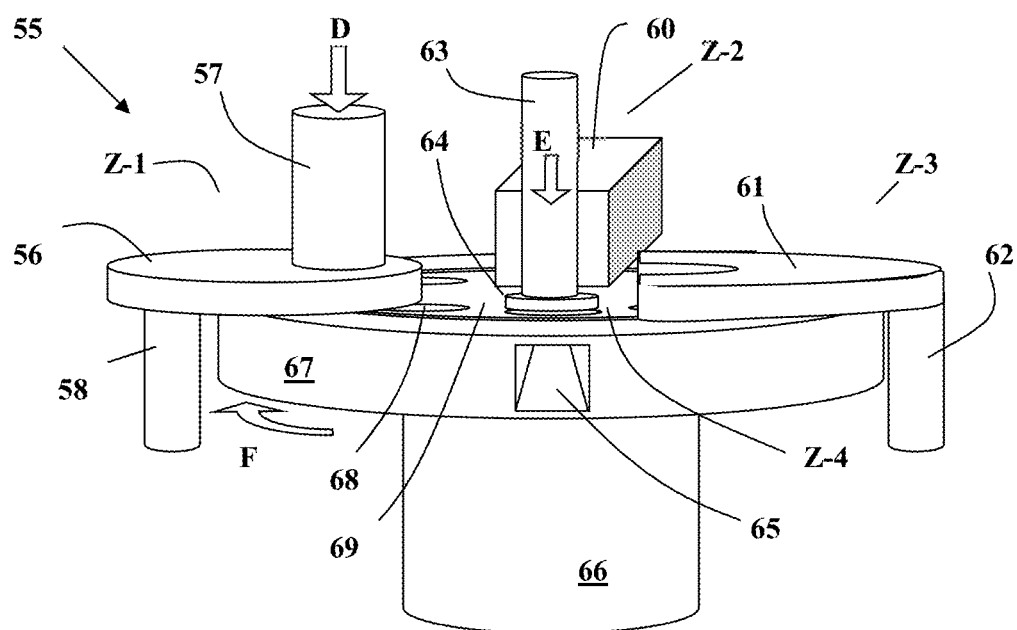
FIG. 6 depicts a perspective view of another exemplary three-dimensional printing equipment assembly (or apparatus) of the invention.

FIG. 6 depicts a perspective view of another exemplary three-dimensional printing equipment assembly (or apparatus) (55), which comprises a powder layering system (56) in the respective region (Z-1), a printing system (60) in the respective region (Z-2), a drying system (61) in the respective region (Z-3), and punch system (63) in the respective region (Z-4). The powdering layering system, which comprises a powder feed system or reservoir (57) is held in place by at least one support (58). The drying system is held in place by at least one support (62). The printing system and punch system are also held in place by supports (not shown). The assembly comprises a stationary body (67), within which a conveyor (69, in this case a turret) comprising a motor drive (66) and plural build modules with respective cavities (68) rotates (spins) to conduct the cavities sequentially through each of the process regions. The punch system (63) comprises a punch (64) with a tip having a periphery that approximates the periphery of the cavities such that the punch can slide in and out of the cavities. Completed articles are discharged through the discharge port (65) or chute.

Figure 7:
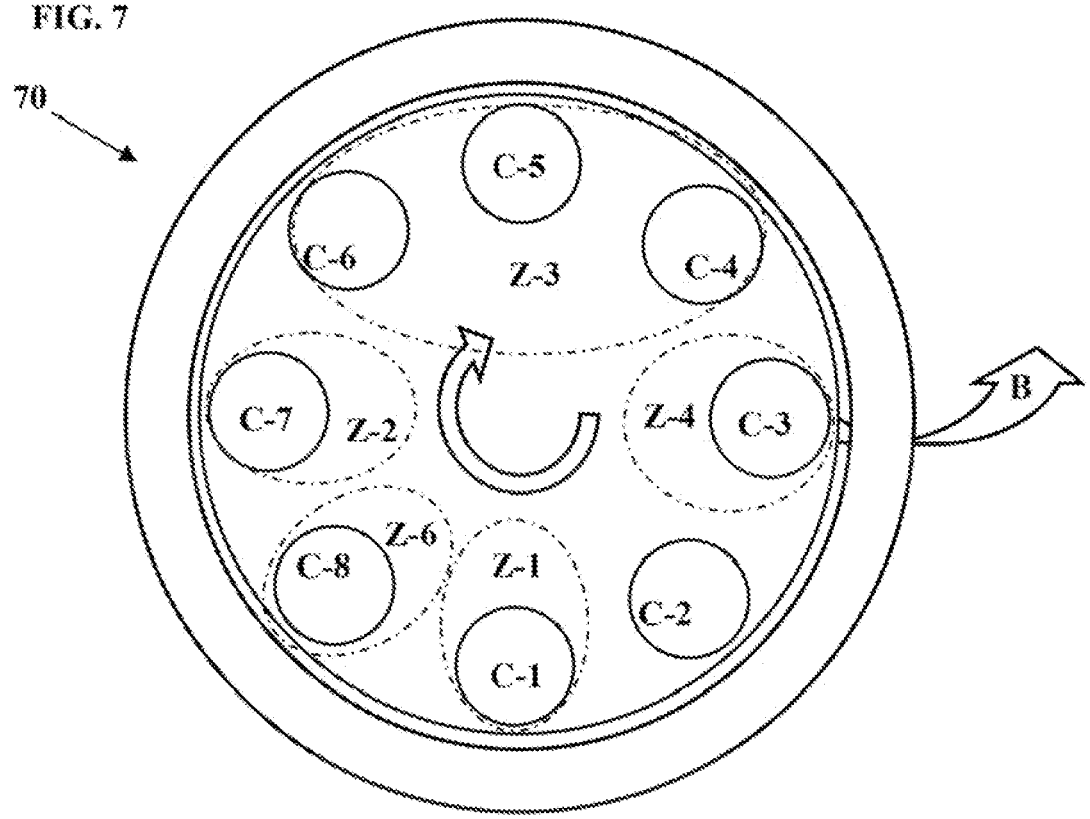
FIG. 7 depicts a top plan view of another exemplary three-dimensional printing equipment assembly (or apparatus) of the invention.

FIG. 7 depicts a top plan view of another exemplary three-dimensional printing equipment assembly (or apparatus) (70) of the invention. It comprises a powder layering region/system (Z-1), a first punch region/system (Z-6), a printing region/system (Z-2), a drying region/system (Z-3), and a second punch region/system (Z-4). Even though the sequential order of the systems of assembly (70) is depicted as (Z-1) to (Z-6) to (Z-2) to (Z-3) to (Z-4), the order can be (Z-1) to (Z-2) to (Z-6) to (Z-3) to (Z-4), or (Z-1) to (Z-2) to (Z-3) to (Z-6) to (Z-4), or (Z-1) to (Z-2) to (Z-3) to (Z-6), or (Z-1) to (Z-2) to (Z-3) to (Z-4).

The first punch system can be used to translate or compress material in a cavity within the corresponding region. It may also be used to smooth the surface of the material. It may also be used to form or shape the surface, i.e. to contour, emboss, deboss or otherwise mark the surface, of the material before printing.

The second punch system can be used to translate or compress material in a cavity within the corresponding region. It may also be used to form or shape the surface, i.e. to contour, emboss, deboss or otherwise mark the surface, of the material before discharging or additional printing. It may also be used to discharge a 3DP article from the cavity.

Figure 8:
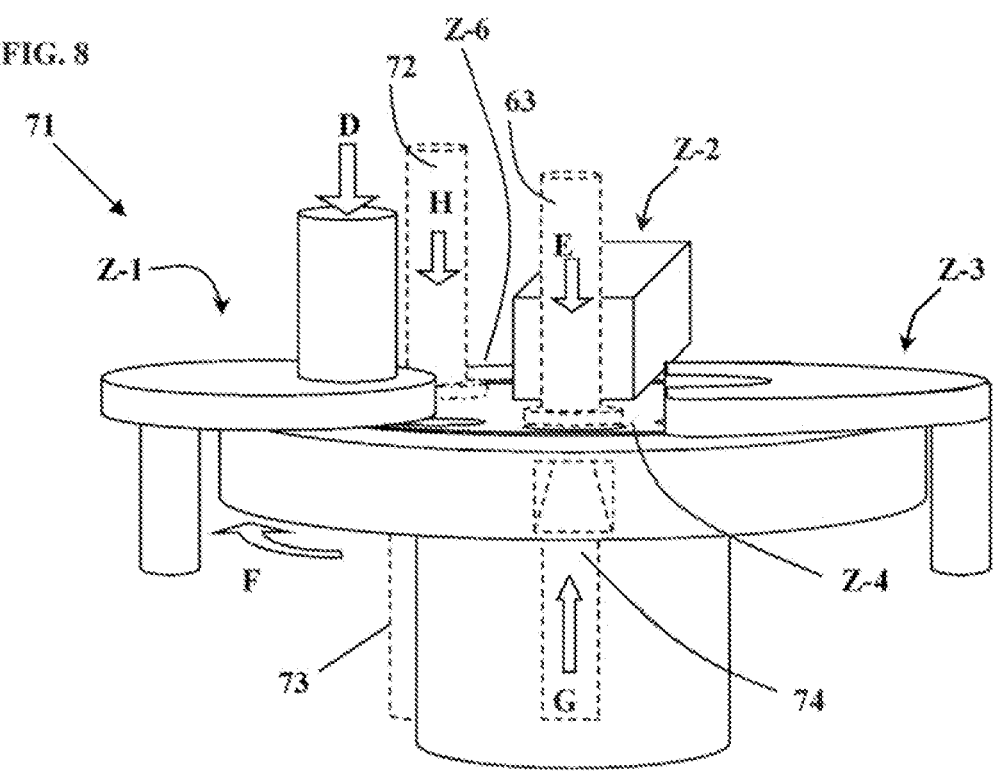
FIG. 8 depicts a perspective view of another exemplary three-dimensional printing equipment assembly (or apparatus) of the invention.

FIG. 8 depicts a perspective view of an exemplary 3DP equipment assembly (or apparatus) (71) of the invention. It is similar to the assembly/apparatus of FIG. 7 in terms of the arrangement or sequence of the respective regions/systems; however, the assembly of FIG. 8 depicts alternative embodiments of the first (Z-6) and second (Z-4) punch systems.

The first punch system comprises an upper punch (72) and a lower punch (73). They are depicted in dashed lines because either one of the two may be absent or both may be present, meaning that the first punch system can comprise the upper punch and/or the lower punch.

The second punch system comprises an upper punch (63) and a lower punch (74). They are depicted in dashed lines because either one of the two may be absent or both may be present, meaning that the second punch system can comprise the upper punch and/or the lower punch. The second punch system can be used to discharge a 3DP article by pushing it upwards or downwards out of its respective cavity.

FIGS. 9A-9I depict partial sectional side elevation views of an exemplary punch system, exemplary powder layering system (81), exemplary build module (83) (with cavity) and exemplary liquid deposition (printing) system (90) during in-process use for the preparation of incremental layers of an uncompressed 3DP article in a cavity.

In FIG. 9A, a first incremental printed layer (85) has already been formed in the cavity of the build module (83). The powder layering system (81) is depicted as having charged loose powder (86) on top of the printed layer. The lower punch (84) is disposed in the cavity and helps maintain the in-process materials in place. The cavity is then conducted to an optional first punch system comprising the upper punch (86, FIG. 9B), which can be lowered (Arrow J, FIG. 9C) onto the loose powder to smooth, contour, modify or mark its surface. The upper punch is then raised (Arrow K, FIG. 9D) and the cavity is conducted to the printing system (90, FIG. 9E), which deposits droplets of binding fluid (91) onto the powder layer such that the in-process (incomplete) 3DP article (92) now comprises two incremental printed layers. After an optional drying step (not depicted), the cavity is then conducted to a second punch system (FIG. 9F), which translates the in-process article (92) downwardly (Arrow J) in the cavity by a vertical distance corresponding to the vertical height (thickness) of the next incremental powder layer to be added to the cavity. After raising the upper punch (Arrow K, FIG. 9G), the cavity is conducted to a powder layering system and charged with another incremental powder layer (93, FIG. 9H), thereby leaving behind the in-process article (94, FIG. 9I) in the cavity.

FIGS. 10A-10C depict an alternate embodiment of the steps depicted in FIGS. 9F-9G. Here, the in-process article (92, FIG. 10A) is compressed by lowering the upper punch (Arrow J, FIG. 10B) into the cavity without lowering or prior to lowering the lower punch, thereby forming the compressed in-process article (5). A space for receiving the next layer is thus created in the cavity (FIG. 10C). The use of punches during the formation steps of a 3DP article for the first time in powder-layering based 3DP technology allows for the formation of 3DP articles comprising compressed and non-compressed incremental printed layers. Accordingly, the invention also provides a 3DP article comprising one or more compressed incremental printed layers and one or more non-compressed incremental printed layers.

Even though the surfaces of the upper and lower punches that contact the in-process 3DP article are depicted as being flat in the embodiments thus far, the surfaces of the punches can be non-flat, meaning shaped (or contoured) as desired. The upper punch (96, FIG. 11A) comprises a convex lower face (97, surface) that forms a corresponding concave face (98) on an incremental layer. Both the upper (96) and lower (99) punches of FIG. 11B comprise convex faces that form corresponding concave faces on an in-process article. The upper punch (100, FIG. 11C) comprises a concave lower face (101, surface) that forms a corresponding complementary convex face (102) on an incremental layer. Both the upper (100) and lower (104) punches of FIG. 11D comprise concave faces that form corresponding complementary convex faces (103) on an incremental layer. Both the upper (118) and lower (119) punches of FIG. 11E have complex contoured faces that form complementary complex contoured faces (114) on an incremental layer.

The use of punches with contoured (non-flat) faces for the first time in powder-layering based 3DP technology allows for the formation of 3DP articles comprising partially or non-uniformly compressed incremental printed layers. Accordingly, the invention also provides a 3DP article comprising one or more partially or non-uniformly compressed incremental printed layers, or comprising one or more partially or non-uniformly compressed incremental printed layers and one or more non-compressed incremental printed layers. The invention also provides a 3DP article comprising one or more contoured (non-flat) incremental printed layers, or comprising one or more contoured incremental printed layers and one or more non-contoured (flat) incremental printed layers.

Other punch faces are contemplated. A punch face may comprise raised (or potentially recessed) lettering, numbering, or other symbols in order to provide an imprint into an exterior or interior incremental layer of a 3DP article that reflects the contour of the punch face in reverse (i.e., a raised feature on the punch face creating a lowered feature on the incremental layer, and vice versa). The punch face may include specific patterns or textures with a similar goal of creating and imprint into an interior or exterior incremental layer of a 3DP article. In certain embodiments, the pattern or texture of features on the punch face allows the powder from more than one incremental layer to mingle within the same horizontal slice of a 3DP article. For example, in a case for which there are two sequential incremental layers with different respective powders, instead of each powder substantially remaining within its own respective layer, one or both powders may shift upward or downward into a neighboring incremental layer when displaced by the action of a non-smooth punch face having raised or recessed features. In certain embodiments, this may include depressions that are created in an instant incremental layer comprised of a first powder that are subsequently filled with a second powder on the next powder spreading step, or this may include raised areas in an instant incremental layer comprised of a first powder and extending into the space allocated for the next incremental layer having a second respective powder, or combinations of both.

The punch system can be used to discharge a 3DP article from a cavity. FIGS. 12A-12B depict the use a lower punch to discharge the 3DP article (105) from a cavity in the build module (123) by pushing the article upwardly (Arrow K) and out of the cavity. The discharged article can then be conducted away from the build module by an article transfer system.

FIG. 13 depicts a perspective view of a prior art uniaxially compressed 3DP dosage form (106B) according to U.S. Pat. Nos. 7,931,914 and 8,758,658, wherein the non-compressed 3DP dosage form (106A) is uniaxially compressed after completion of the build cycle and completion of the drying cycle. The entire uniaxially compressed dosage form (106B) comprises only uniformly compressed printed incremental layers, because the entire dosage form was uniformly uniaxially compressed after formation of all the incremental layers. It does not comprise a combination of compressed and non-compressed incremental printed layers. It does not comprise a non-uniformly compressed incremental printed layer or a combination of a non-uniformly compressed incremental printed layer and a non-compressed incremental printed layer.

The assembly (apparatus) and method of the invention, however, now permit the formation of powder layering-based 3DP articles having complex internal and external geometries. The 3DP article (107) of FIG. 14A comprises a non-compressed incremental printed layer (108) and a compressed incremental printed layer (109). The 3DP article (110) of FIG. 14B comprises a first section (111) of non-compressed incremental printed layers (first lowest density section), a second section (112) of lightly compressed incremental printed layers (second intermediate density section), and a third section (113) of more heavily compressed incremental printed layers (third highest density section). Other 3DP articles comprising compressed and non-compressed incremental printed layers of varying geometries can also be prepared.

The 3DP article (115) of FIG. 15A comprises upper and lower higher density sections (117) and an intermediate lower density section (116). The 3DP article (120) of FIG. 15B comprises a first section (121) comprising a first bulk powder and a second section (122) comprising a second bulk powder, wherein the powders differ in composition.

The use of non-flat punches faces now permits preparation of powder-layering based 3DP articles having embossed or debossed surface features. The 3DP article (124) of FIG. 15C comprises a face with a debossed (lowered) feature (125). The 3DP article (126) of FIG. 15D comprises opposing faces with corresponding embossed (raised) features (128).

The 3DP article (124) of FIG. 15C can be modified to include more than one bulk powder composition in an incremental printed layer. FIG. 15 depicts a sectional side elevation view of the 3DP article (124) comprising lower (124b) and upper (124a) printed layers, each made from a first bulk powder onto which a first binding fluid has been deposited. The upper layer includes the space (125) created by using a punch with a non-flat surface (an embossed face). The space has been filled in with a second bulk powder that is different in composition than the first bulk powder of the layers (124a, 124b). As a result, the incremental printed layer (124a) comprises at least one first portion (region), made from a first bulk powder and a first binding fluid, and at least one second portion (region), made from a second bulk powder and second binding fluid. The first and second portions are horizontally adjacent (immediately adjacent). The first bulk powder is different from the second bulk powder. The first and second binding fluids can be the same or different. The difference(s) can be difference(s) in composition and/or physical properties.

FIG. 16 depicts a partial sectional side elevation view of an exemplary liquid removal system (130), lower punch (138) and build module of the invention. This liquid removal system (dryer) is particularly suitable for removing liquid from incremental printed layers during preparation of an in-process 3DP article. It comprises a body (131) having a duct (133) for conducting air from a source (132) through to the surface of the target incremental layer (137). The dryer optionally comprises a temperature sensor (135) for sensing the temperature of the air. If the conducted air is not heated beforehand, it may be heated with one or more heating elements (134) in the body (131). Moist air, which rises from the process area of the dryer, can be captured and removed from the process area by an evacuation system (136).

The alternate liquid removal system (140, FIG. 17) comprises one or more heating elements (141) superposing the drying process area and/or one or more heating elements (142) embedded within the build module in a location thermoconductively adjacent to the cavity.

Figure 18:
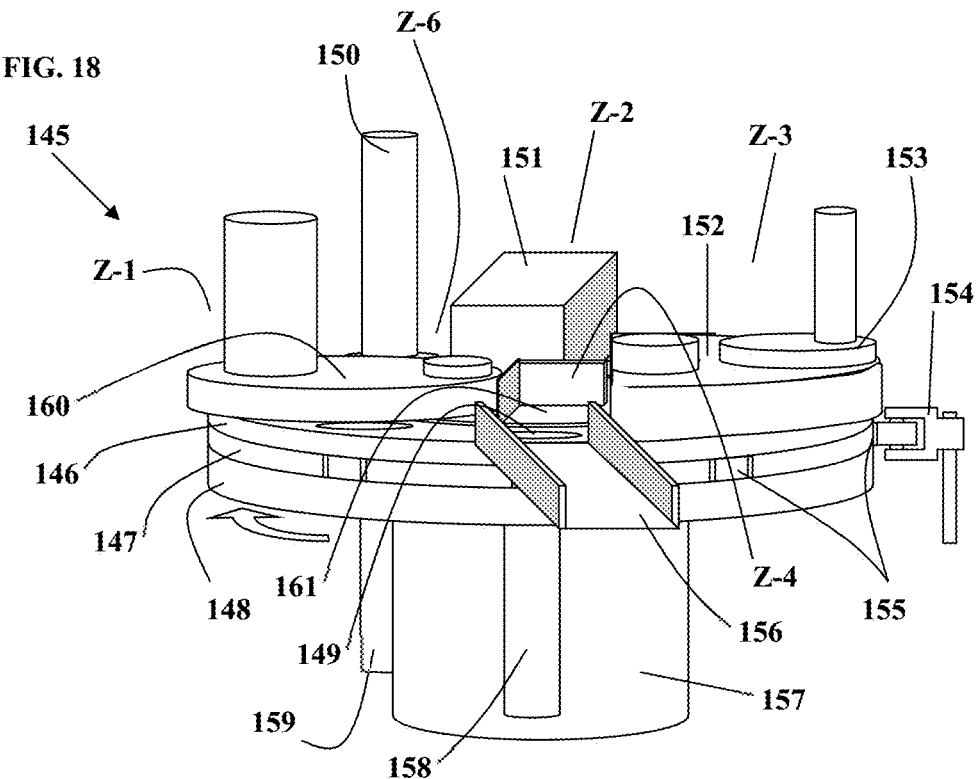
FIG. 18 depicts a perspective view of another exemplary three-dimensional printing equipment assembly (or apparatus) of the invention.

The 3DP equipment assembly/apparatus of the invention can be provided in varying embodiments. FIG. 18 depicts an assembly/apparatus (145) comprising a powder layering region/system (Z-1), first punch region/system (Z-6), printing region/system (Z-2), drying region/system (Z-3), discharge region/system (Z-4), drive motor/system (157), height adjuster (154), combination rotary conveyor and build module system (146, 147) with plural cavities (149), and stationary body (148). The first punch system comprises an upper punch (150) and a lower punch (159). The system also comprises a second lower punch (158) that discharges 3DP articles from their respective cavities by pushing them upwards so that a push mechanism (161) can direct the 3DP article to the chute (156). The drive motor drives the conveyor which conducts cavities from one region to another. The height adjuster (154) adjusts the height of the height adjustable platform in each cavity.

Figure 19:
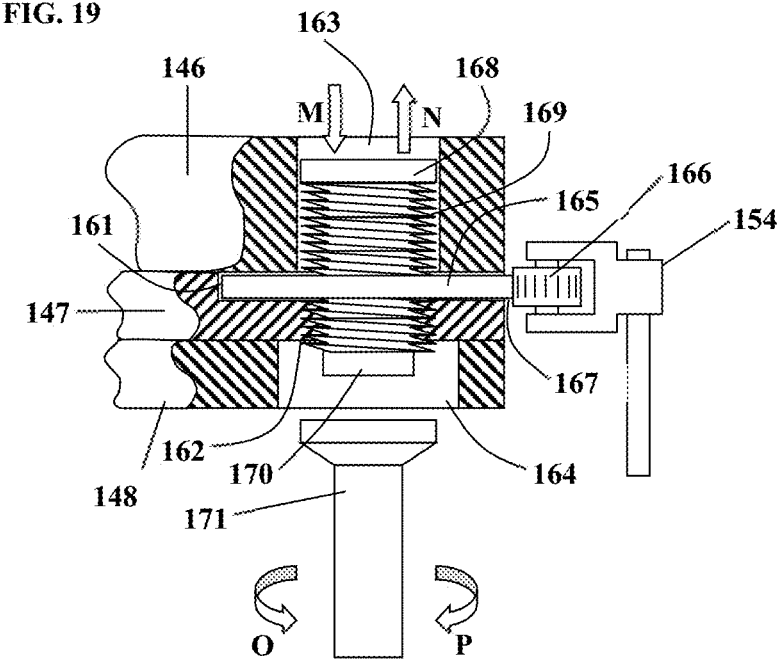
FIG. 19 depicts a partial sectional side elevation view of an exemplary build module, height adjustable platform and lower punch of the invention.

FIG. 19 depicts a partial sectional side view of the combination rotary conveyor and build module system (146, 147) with a respective cavity (163), the height adjuster (154), and a lower rotary drive (171). As the conveyor (147) rotates, it rotates the build modules (146) engaged to it. In this particular embodiment, the build module comprises a height adjustable platform (168) having a threaded body (169) engaged with a complementarily threaded nut (165) and with a complementarily threaded bore (162) of the conveyor (147). The outer perimeter of the nut (165) briefly contacts the foot or wheel (166) of the height adjuster (154), thereby rotating the nut and causing the height of the platform (168) to lower (Arrow M) with respect to the upper surface of the build module. Alternatively, the platform can be raised (Arrow N) or lowered (Arrow M) by rotating the nut (165) in the required direction with the height adjust (154) or by engaging the bottom of the threaded body (169) with the lower rotary drive (171), which is rotated (Arrow O or Arrow P) in the required direction.

Figure 20:
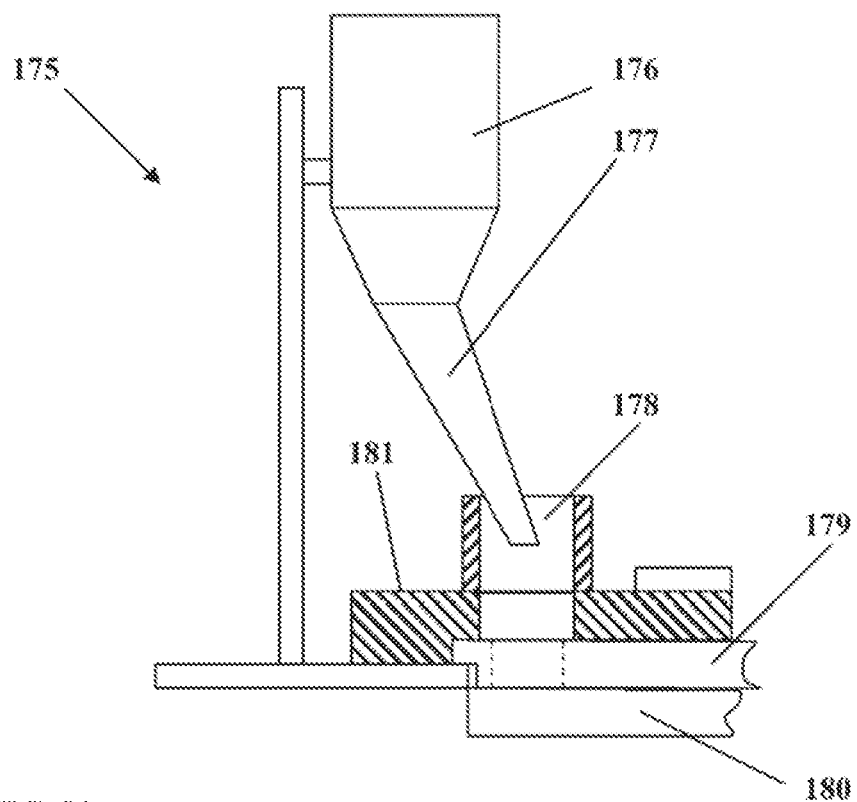
FIG. 20 depicts a partial sectional side elevation view of an exemplary powder layering system and build module of the invention.

The powder layering system typically comprises a powder spreader, powder feeder and powder reservoir. FIG. 20 depicts a powder layering system (175) comprising a reservoir (176), feeder (177), hopper (178), and body (181), which also serves as a spreader. The powder layering system forms a layer of powder in a cavity by dropping powder from the hopper into the cavity. The spreader spreads the powder, if needed, in the cavity and also removes excess powder from the cavity.

Figure 21:
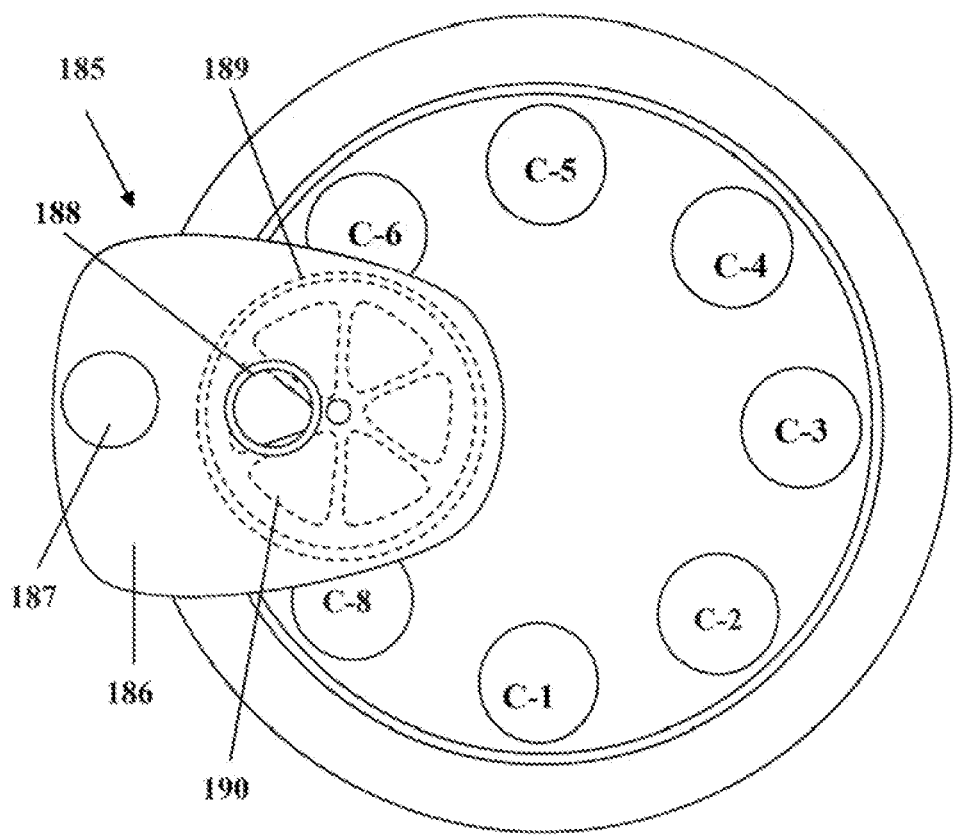
FIG. 21 depicts a top plan view of an exemplary powder layering system and exemplary turret with plural receptacles.

FIG. 21 depicts a top plan view of an alternate powder layering system (185) comprising a support (187), hollow body or shroud (186) within which a paddle wheel spreader (189) is disposed. During use, powder charged into the hopper (188) is dropped into the spreader, which drops powder into a cavity beneath the spreader. The spreader spins to remove excess powder from the cavity and smooth the surface of the powder in the cavity. Cavities (C-1 to C-8) are repeated filled in this manner.

Figure 22:
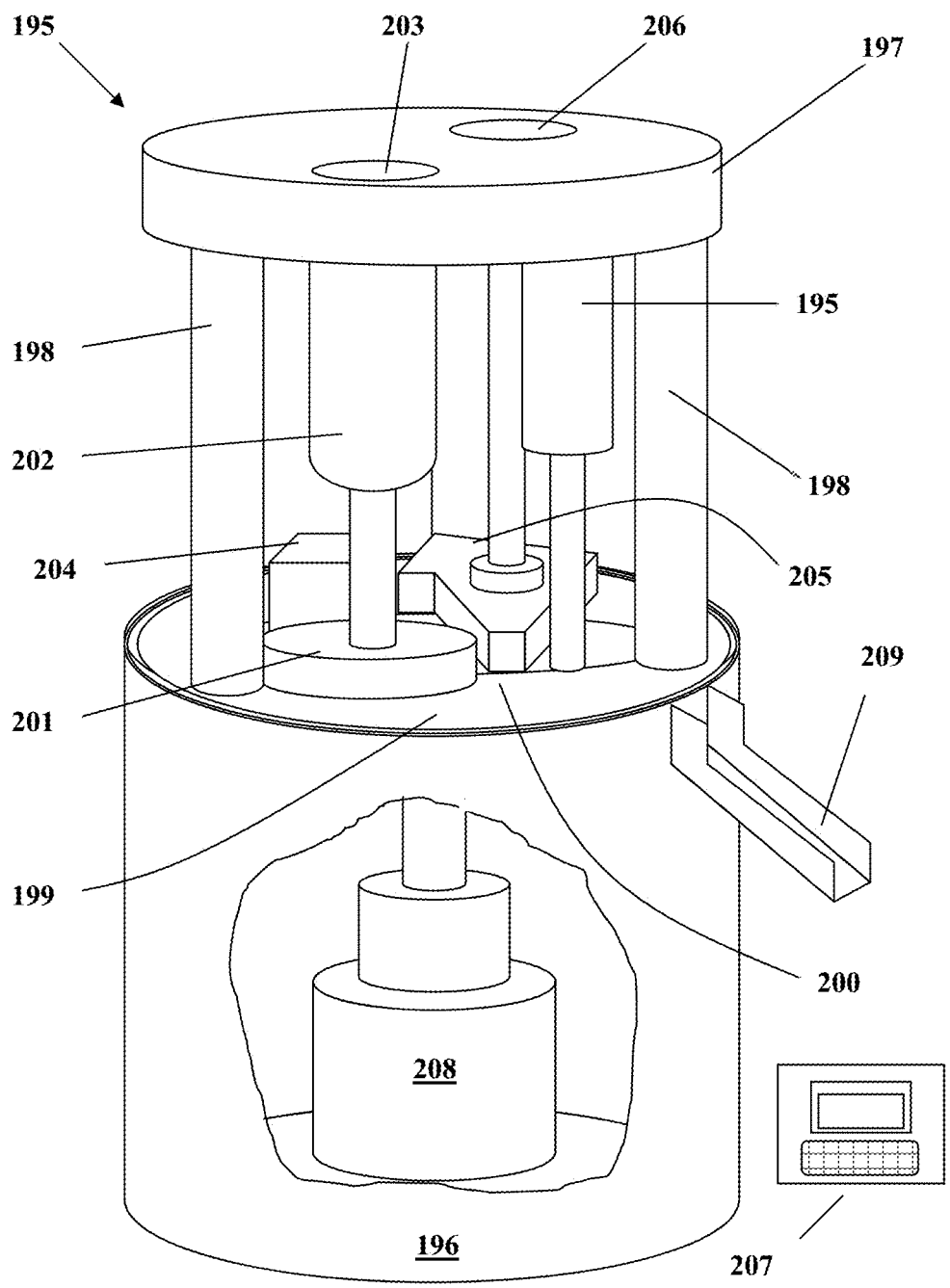
FIG. 22 depicts a partial sectional perspective view of a 3DP apparatus of the invention.

The equipment assembly/apparatus (195) of FIG. 22 comprises a drive system (208) that spins/rotates the combination conveyor and build module system (200) such that its cavities are conducted beneath the powder layering system (201), printing system (204), drying system (205) and punch system (195). The powder layering system has a reservoir (202) that can be charged through a port (203) in the cover (197) of the assembly/apparatus (195). The cover is supported by supports (198) that are mounted onto a stationary platform (199). The drying system includes an evacuation system that removes moist air from the drying area through a tube and out through a port (206) in the cover (197). 3DP articles are discharged from cavities to a chute (209) that directs the articles further downstream in the process, e.g. for drying or dedusting. Various components are computer (207) to synchronize their operation.

A build lap with the assembly/apparatus (195) requires a single complete revolution of the conveyor such that a 3DP article comprising 10 incremental printed layers would required 10 build laps (10 revolutions) of the conveyor. However, the various components of the system can be arranged as needed to provide the desired process steps with respect to revolutions of a conveyor.

Figure 23:
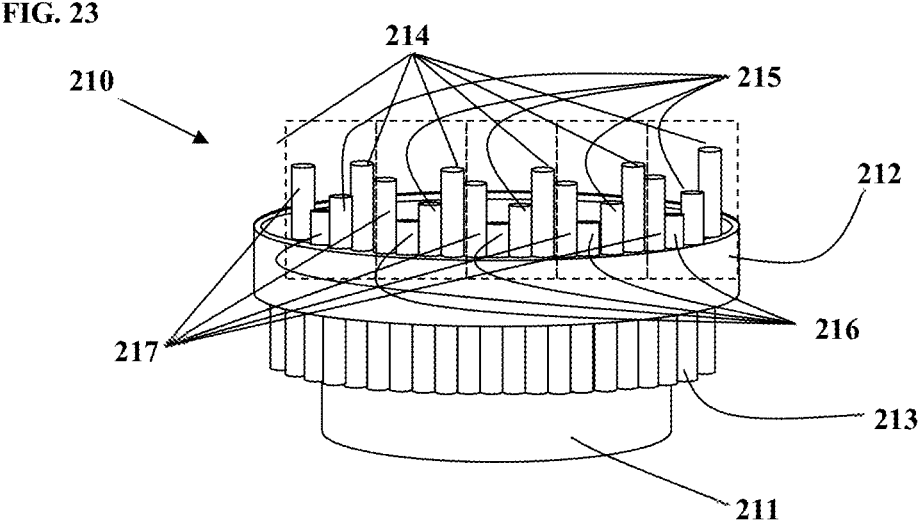
FIGS. 23-25 depict perspective views of three different exemplary 3DP equipment assemblies (or apparatuses) of the invention.

The assembly/apparatus (210) of FIG. 23 plural process stations (enclosed in dashed lines), each station comprising in sequence a powder layering system (214), a printing system (215), a drying system (216), and a punch system (217). This assembly comprises at least ten process stations (five shown and five not shown) arranged sequentially along the length of the conveyor (212). This means that only a single revolution of the conveyor (driven by the drive system (211)) would be required to prepare a 3DP article comprising ten incremental printed layers. This assembly also comprises a lower punch beneath each cavity, but only comprises ten upper punches above the cavities. In other words, the assemblies of the invention can comprise less upper punches than lower punches, meaning they can comprise partial and full punch systems.

Figure 24:
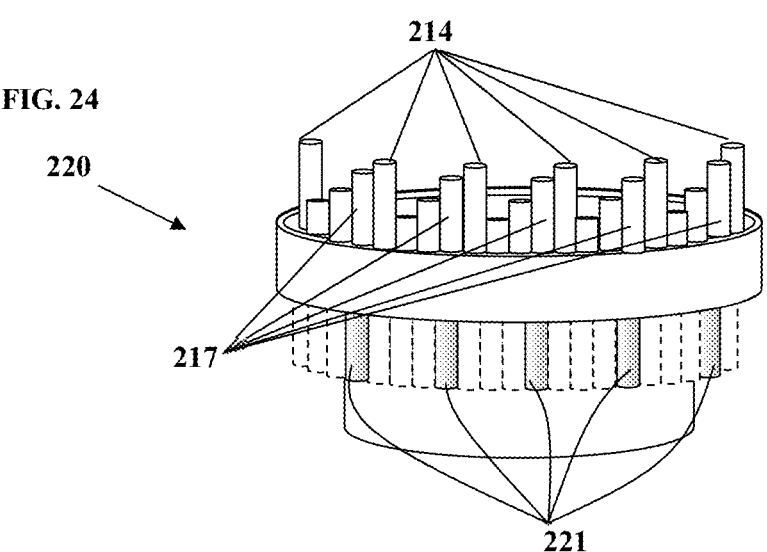

The assembly/apparatus (220) of FIG. 24 differs from that of FIG. 23 in that each process station comprises in sequence a powder layering system (214), a punch system (217), a printing system (215), a drying system (216), meaning that the punch system has been placed in a different operational order with respect to the one of FIG. 23. Moreover, this optional embodiment does not require a lower punch beneath each cavity, since the lower punches (221) are only located beneath the upper punches (217). The other lower punches are optional. However, this assembly still comprises ten process stations (five depicted, five not depicted)

Figure 25:
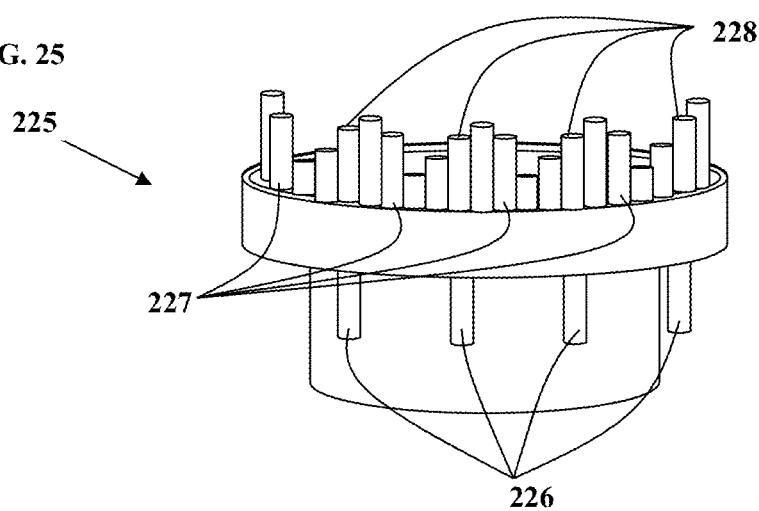

The assembly/apparatus of FIG. 25 comprises eight process stations, each comprising in order a powder layering system, a first punch system (228), a printing system, a drying system, and a second punch system (227). As in FIG. 24, this assembly does not require a lower punch beneath each cavity.

Figure 26:
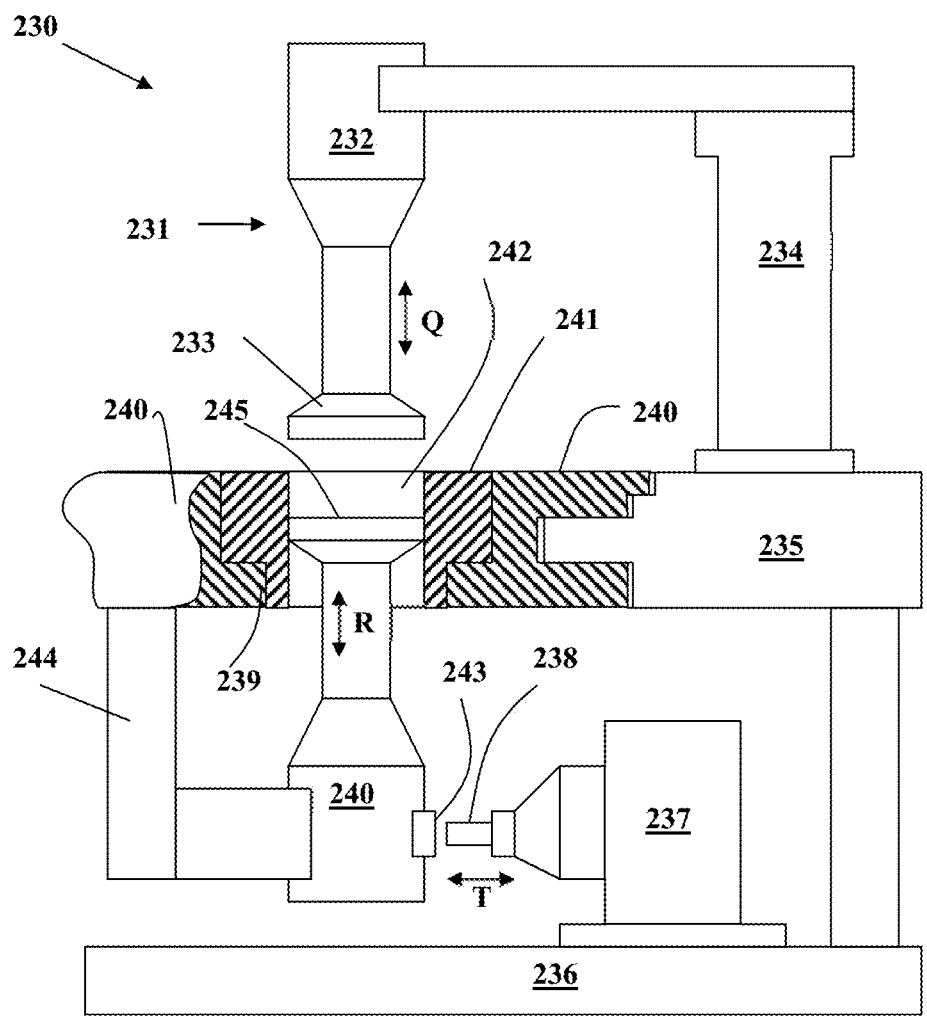
FIG. 26 depicts a partial sectional side elevation view of an exemplary punch system and exemplary build module of the invention.

FIG. 26 includes a more detailed partial sectional side elevation view of the assembly (230) comprising an upper punch system (231), upper punch drive (232), upper punch (233), support (234), platform (235), base (236), conveyor drive (244), conveyor (240), build module (241), cavity (242), lower punch drive (240), lower punch (245), lower punch actuator (237), and coupling (238, 243). The build module can be a bushing, shaft, collet, sheet, die or other similar device such that a conveyor will comprise plural such devices each having a cavity therein. The build module is placed within a seat (239) in the conveyor. The upper and lower punches are aligned with each other and the cavity. In this embodiment, the lower punch is substantially equivalent to a height adjustable platform within the cavity. During operation, the cavity is placed between the punches. The upper punch drive (232) raises and lowers (Arrow Q) the upper punch (233). The lower punch drive (240) raises and lowers (Arrows R) the lower punch (245) after the actuator (237) has coupled with the drive (240) by laterally (Arrow T) engaging the shaft (238) with the coupling (243). In an alternate embodiment, the lower punch drive (240) is removed and the actuator (237) engages with the lower punch and then raises and lowers the punch directly.

Assemblies/apparatuses of the invention comprising plural build stations are particularly suitable for preparing 3DP articles comprising incremental layers differing in composition. In some embodiments, a 3DP article comprises: a) at least a first incremental printed layer comprising a first bulk powder, and at least a second incremental printed layer comprising a different second bulk powder; b) at least a first incremental printed layer comprising a first composition, and at least a second incremental printed fluid comprising a different second composition; c) at least a first incremental printed layer comprising at least one component from a first binding fluid, and at least a second incremental printed fluid comprising at least one different component from a second binding fluid; or d) a combination thereof.

The invention also provides a process for preparing a 3DP article comprising at least a first incremental printed layer comprising a first composition and at least a second incremental printed layer comprising a different second composition, the process comprising: a) forming at least one first incremental printed layer; and b) forming at least one second incremental layer, wherein: 1) bulk powder used to form the first incremental printed layer is different from the bulk powder used to form the second incremental printed layer; 2) printing fluid used to form the first incremental printed layer is different from printing fluid used to form the second incremental printed layer; or 3) a combination of 1) and 2), and wherein there is no substantial excess of one or more bulk powders surrounding a 3DP article when formed.

Figure 27:
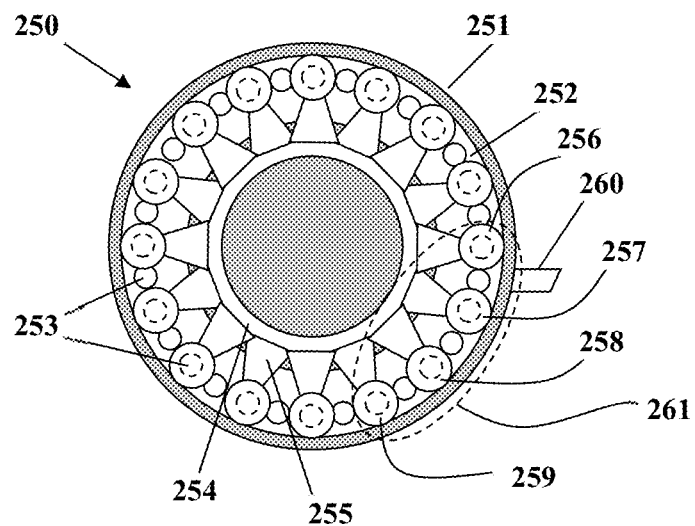
FIG. 27 depicts a top plan view of an exemplary 3DP equipment assembly (or apparatus) of the invention.

FIG. 27 depicts a top plan view of an alternate assembly/apparatus (250) of the invention comprising a body (251), conveyor (252) with plural build modules and respective cavities (253, some depicted in dashed lines), a support system (254), discharge system (260) and plural build stations (261, exemplary one encircled in dashed line), which build stations comprise powder layering systems (256), printing systems (257), in-process layer drying systems (258), and punch systems (259). The assembly/apparatus (250) comprises four build stations. In this embodiment, a single cycle of the conveyor provides four build laps. The bulk powder in each respective build station can be the same or different than that of another. The binding fluid in each respective build station can be the same or different than that of another. If desired, this assembly/apparatus can be used to prepare 3DP articles comprising two, three, four or more incremental printed layers differing in composition.

Figure 28:
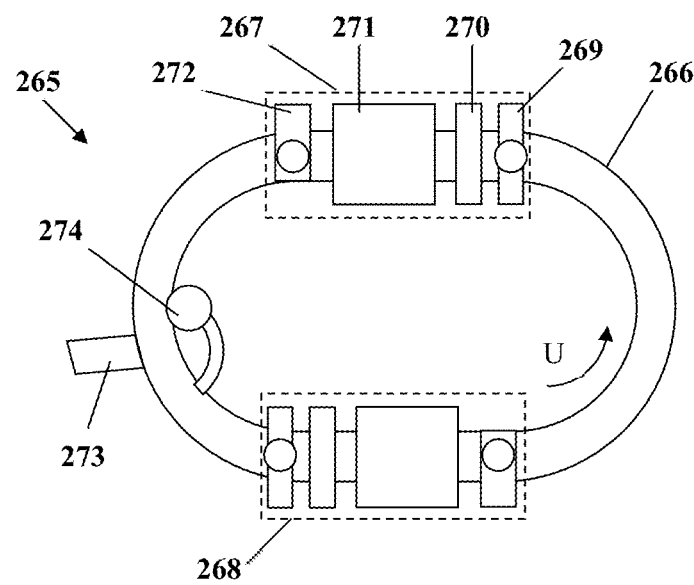
FIG. 28 depicts a top plan view of an exemplary continuous 3DP equipment assembly having a racetrack conveyor, plural build stations and an article transfer system.

FIG. 28 depicts a top plan view of an alternate assembly/apparatus (265) comprising a cyclic conveyor (266), plural build modules with respective cavities (not depicted), at least one discharge system comprising a discharger (274) and chute (273), and plural build stations (267, 268), each comprising a powder layering system (269), printing system (270), in process layer drying system (271), and punch system (272). In this embodiment, a single cycle of the conveyor provides two build laps. The bulk powder in each respective build station can be the same or different than that of another. The binding fluid in each respective build station can be the same or different than that of another. If desired, this assembly/apparatus can also be used to prepare 3DP articles comprising two or more incremental printed layers differing in composition.

Figure 29:
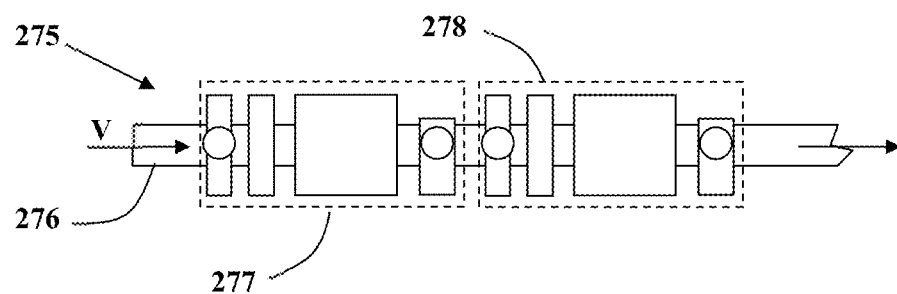
FIG. 29 depicts a top plan view of another exemplary continuous 3DP equipment assembly having a linear conveyor and plural build stations.

FIG. 29 depicts a top plan view of a portion of an alternate assembly/apparatus (275) comprising a linear conveyor (276), plural build modules with respective cavities (not depicted), at least one discharge system comprising (not depicted), and plural build stations (277, 278), each comprising a powder layering system, printing system, in process layer drying system, and punch system. Build modules are conducted sequentially through build stations (Arrow V). The bulk powder in each respective build station can be the same or different than that of another. The binding fluid in each respective build station can be the same or different than that of another. If desired, this assembly/apparatus can also be used to prepare 3DP articles comprising two or more incremental printed layers differing in composition.

Figure 30:
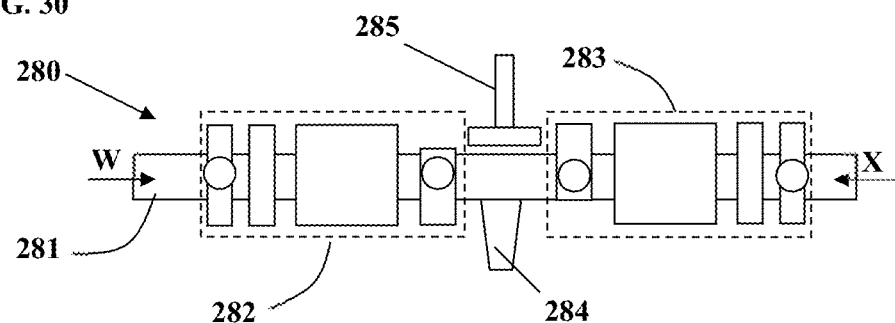
FIG. 30 depicts a top plan view of another exemplary continuous 3DP equipment assembly having a linear conveyor, plural build stations and an article transfer system.

FIG. 30 depicts a top plan view of an alternate assembly/apparatus (280) comprising a reciprocating (oscillating) conveyor (281), plural build modules with respective cavities (not depicted), at least one discharge system comprising a discharger (285) and chute (284), and plural build stations (282, 283), each comprising a powder layering system, printing system, in process layer drying system, and punch system. In this embodiment, the conveyor conducts build modules back and forth (Arrows W and X) through the build stations. The bulk powder in each respective build station can be the same or different than that of another. The binding fluid in each respective build station can be the same or different than that of another. If desired, this assembly/apparatus can also be used to prepare 3DP articles comprising two or more incremental printed layers differing in composition.

Figure 31:
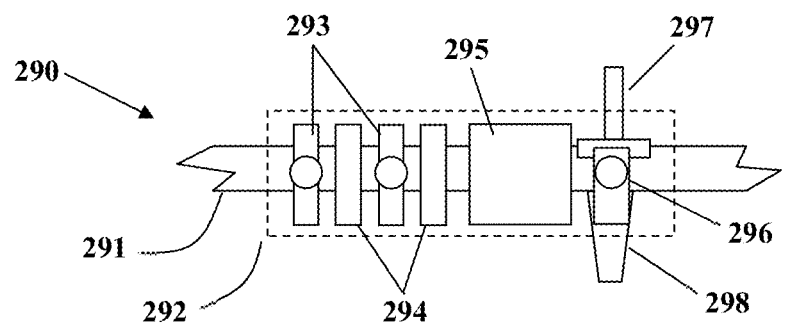
FIG. 31 depicts a top plan view of a portion of another exemplary continuous 3DP equipment assembly having a conveyor, build station and article transfer system.

FIG. 31 depicts a top plan view of a portion of an alternate assembly/apparatus (290) comprising a conveyor (291), plural build modules with respective cavities (not depicted), at least one discharge system (not depicted), and at least one build station (292) comprising at least two powder layering systems (293), at least two printing systems (294), at least one process layer drying system (295), at least one punch system (296) and at least one discharge system (297, 298). Build modules are conducted through the first powder layering system to the first printing system to the second powder layering system to the second printing system and to the layer drying system. Another punch system (not depicted) can be placed between the first printing system and the second powder layering system. In such case, build modules are conducted through the first powder layering system to the first printing system to the first punch system to the second powder layering system to the second printing system and to the layer drying system.

Figure 32:
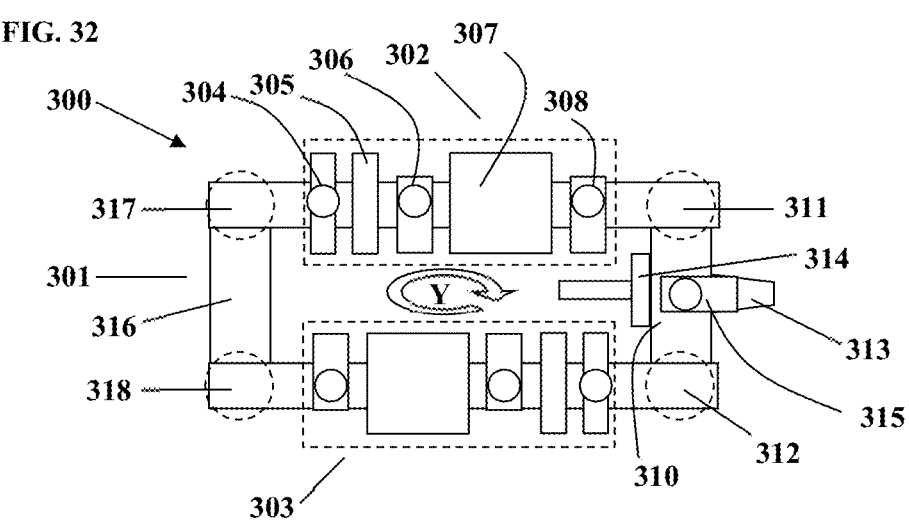
FIG. 32 depicts a top plan view of an exemplary continuous 3DP equipment assembly having a segmented conveyor with horizontal displacement, plural build stations and an article transfer system.

FIG. 32 depicts a top plan view of an alternate assembly/apparatus (300) comprising a modular conveyor (301), plural build modules with respective cavities (not depicted), at least one discharge system (313, 314)), at least two build stations (302, 303), at least two build module transfer means (310-312, 316-318). The build station comprises a powder layering system (304), a printing system (305), a first punch system (306), a process layer drying system (307), and a second punch system (308). With a first portion of the conveyor, build modules are conducted (Arrow Y) through each system of one build station and then transferred to another portion of the conveyor using the transfer means. Completed 3DP articles are discharged with the discharge system and a punch system (315). A single conveyor cycle thus provides two build laps.

Figure 33:
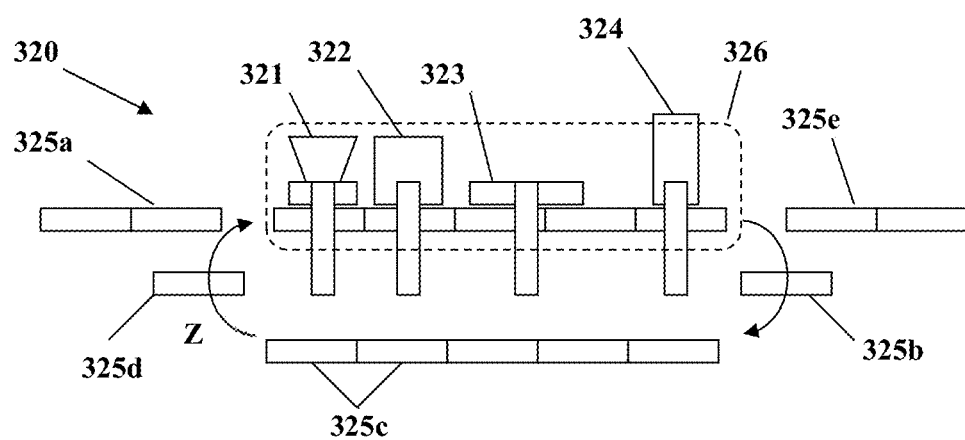
FIG. 33 depicts a side elevation view of an exemplary continuous 3DP equipment assembly having a modular conveyor with vertical displacement and a build station.

The assembly/apparatus (320) of FIG. 33 (side elevation view) provides vertical displacement of build modules (325a-325e) using a combination linear and cyclic (Arrow Z) modular conveyor. Modules (325a) are loaded into the cyclic portion of the conveyor and through the powder layering system (321), printing system (322), layer drying system (323) and punch system (324) of the build station (326). The modules are then displaced vertically (325b) and cycled (325c, 325d) back to the entry point of the build station. Upon completion of printing, modules (325e) are conducted away from the build station. The invention thus provides a 3DP assembly/apparatus comprising a combination modular (segmented) conveyor system comprising at least one linear region and at least one cyclic region. A single conveyor cycle thus provides one build lap.

Figure 34:
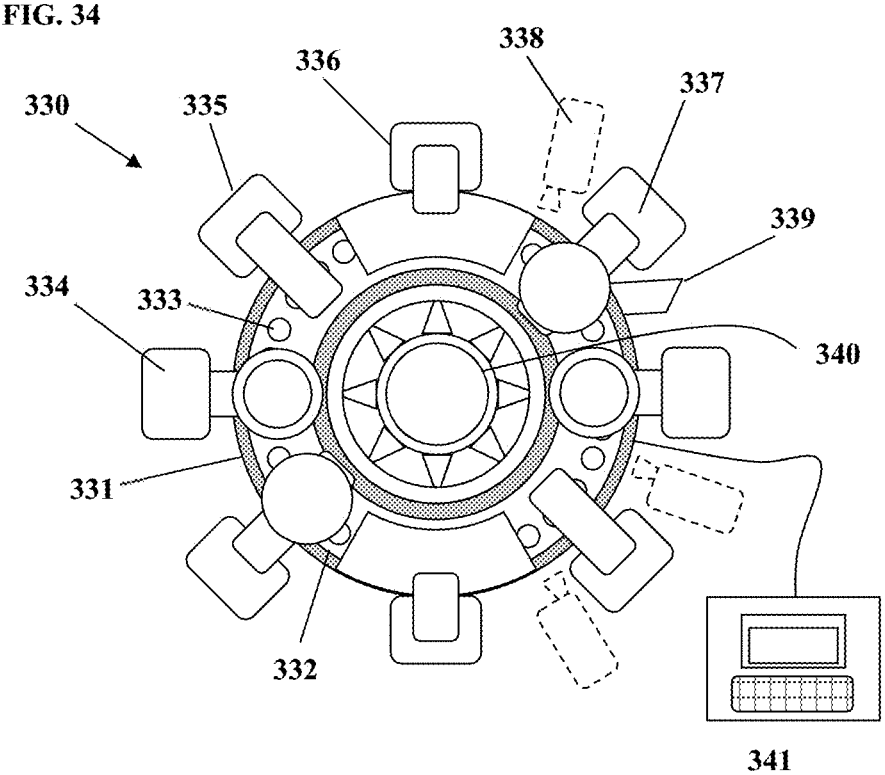
FIG. 34 depicts a top plan view of an exemplary continuous 3DP equipment assembly having a conveyor, plural powder layering systems, plural printing systems, plural punch systems, plural drying systems, computer controller, an article transfer system and optionally one or more inspection systems.

FIG. 34 depicts a top plan view of an alternate assembly/apparatus (330) of the invention comprising a body (331), a conveyor (332) with plural cavities (333), drive means (340) for advancing the conveyor from one position to the next, a computer controller (341), discharge system (339), and two build stations, each comprising a powder layering system (334), printing system (335), drying system (336), and punch system (337). The system further comprises one or more inspection systems (338) for in-process monitoring features of the incremental powder layers and/or printed layers. A single conveyor cycle thus provides two build laps. The bulk powder in each respective build station can be the same or different than that of another. The binding fluid in each respective build station can be the same or different than that of another. If desired, this assembly/apparatus can also be used to prepare 3DP articles comprising two or more incremental printed layers differing in composition.

A discharger (discharge system) can comprise substantially any means for moving a solid material from one location to another, especially a system adapted for removing solids from a conveyor. A discharger can comprise a rod, bar, plate, diverter, or other fixed or articulated moving means for lifting or pushing or otherwise transferring articles so as to exit one section of an apparatus, system, or component, and optionally to enter another. In a first position, a discharger does not direct articles away from the build system and in a second position it does.

Figure 35:
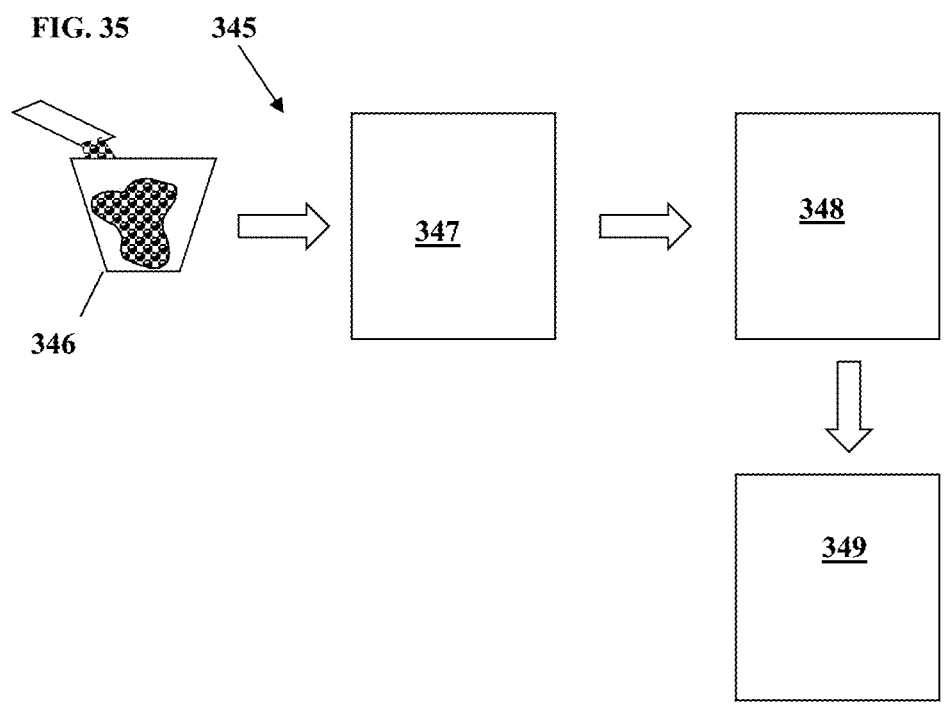
FIG. 35 depicts an overall process flow diagram indicating movement of 3DP articles through various parts of the equipment assembly.

3DP articles are further processed downstream from the build system. FIG. 35 depicts a generalized sequence of process areas/systems (345) comprising a 3DP article collection system (346), a 3DP article drying system (347), a 3DP article dedusting system (348) and a 3DP article packaging system (349). Each of these systems can process one or more articles at a time. Although the depiction of a 3DP article collection system (346) implies gravimetric filling of a bulk container, this depiction is only symbolic, as all other collection means are contemplated and may be deployed in analogous sequence to that shown in FIG. 35.

Figure 36:
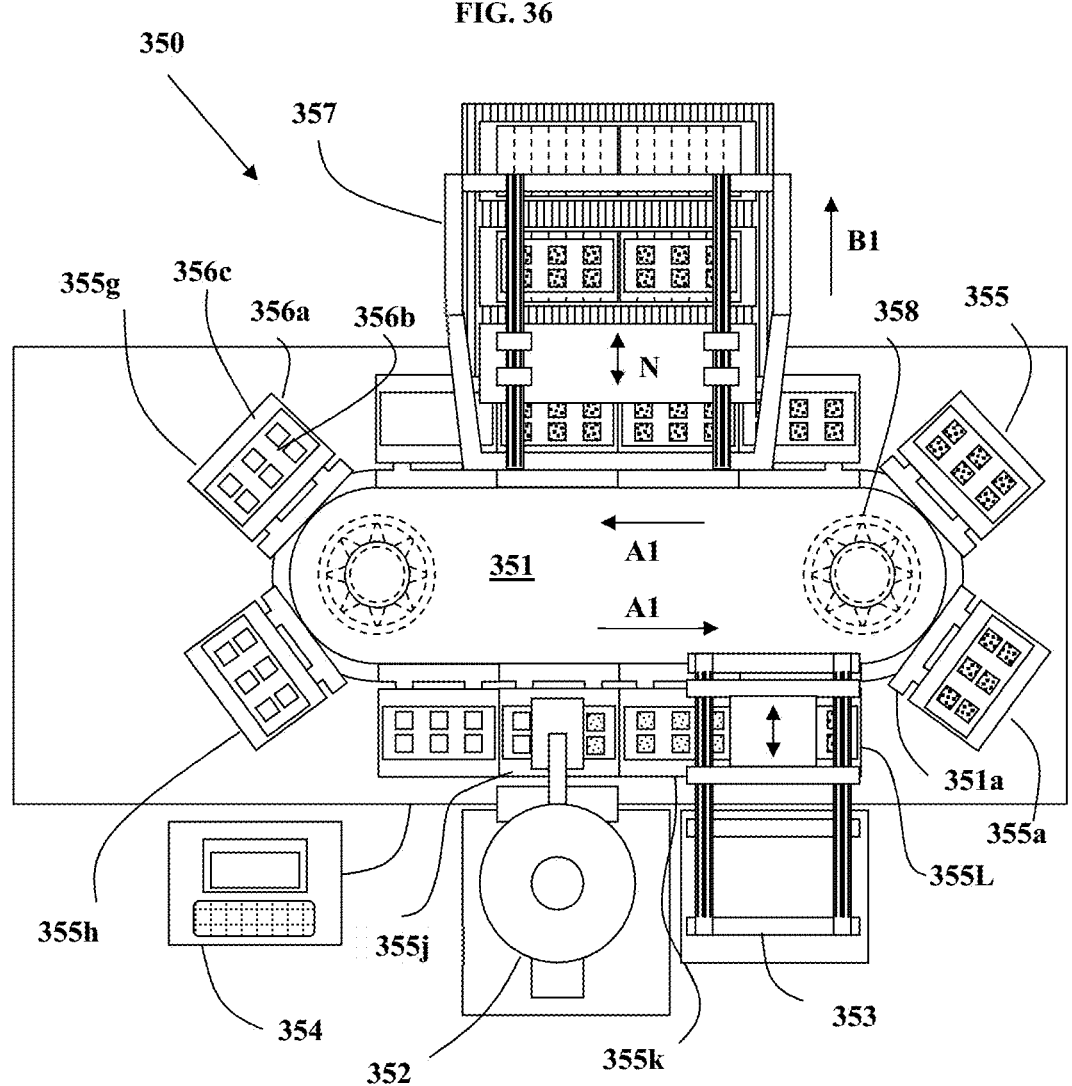
FIG. 36 depicts a top plan view of an exemplary layout of an exemplary multi-cavity three-dimensional printing equipment assembly.

FIG. 36 depicts a top plan view of an exemplary multi-cavity three-dimensional printing equipment assembly (350) comprising a conveyor (351) that conducts plural build modules (355) engaged with the conveyor system along a predetermined path through build regions in one or more build stations, respectively, comprising: a) at least one powder layering system (352) that forms incremental powder layers within build modules; and b) at least one printing system (353) that deposits a liquid (binding fluid) according to a predetermined pattern to incremental powder layers within build modules. The build modules receive and temporarily retain powder from the powder layering system. The cyclic conveyor system forms a continuous loop system that repeatedly transports/cycles the build modules from the at least one powder layering system to the at least one printing system to form a 3DP bed or form one or more 3DP articles in the cavities of the build modules. The exemplary conveyor system comprises at least one drive (358) and plural conveyor modules (351a), thereby forming a segmented or modular conveyor system. A conveyor module is engaged with a corresponding build module and conducted along a predetermined pathway in the direction of Arrow A1.

The equipment assembly in FIG. 36 is depicted finishing printing of a first batch of 3DP articles, via a cavity 3DP process, and starting the 3-D printing of a second batch of 3DP articles. The just-completed 3DP articles from the end of a first build cycle are in build module (351a), and the beginning of the second batch starts with a printed incremental layer in build module (355L). Build module (355a)

includes six 3DP articles, each in its respective cavity. In cavity 3DP, the top plan view of the 3DP articles approximates the top plan view of the respective cavities, which in this particular embodiment are depicted as square-shaped. As the build modules (355, 355a-355L) are conducted along the predetermined course, they pass through the article transfer system (357), which transfers build modules and completed 3DP articles or just completed 3DP articles, one or more at a time, away from the 3DP build system. A build module comprises a body (356a), and upper surface (356c) having plural cavities within each of which a height adjustable build platform (356b) is disposed. The build module (355h) is now ready to receive powder.

The build module (355j) is depicted passing through the powder dispensing region of a powder layering system. The build module (355k) is depicted between the powder layering system and the printing system. The build module (355L), which is the first build module of the next build lap, is depicted passing through the printing region of the printing system. A control system, comprising at least one or more computers and one or more use interfaces (354), can be used to control and integrate (coordinate) operation of the various components and systems of the equipment assembly. In some embodiments, operation of each of the conveyor system, the height adjustable platforms of the build modules, the at least one powder layering system, and the at least one printing system are controlled by the control system. In some embodiments, operation of the bed transfer system is controlled by the control system.

An equipment assembly can further comprise an article and/or build module transfer system (357) that transfers 3DP articles (and optionally corresponding build modules), one or more at a time, away from the 3DP build system. The exemplary transfer system simultaneously removes two or more 3DP articles or build modules in an article transfer region.

In some embodiments, a three-dimensional printing equipment assembly comprises:
a) a three-dimensional printing build system comprising:
a conveyor system adapted to conduct plural build modules;
plural build modules engaged with the conveyor system, wherein the build modules can receive and temporarily retain powder from a powder layering system, and wherein each build module comprises one or more cavities; and
at least one build station comprising: 1) at least one powder layering system adapted to form incremental powder layers within build modules temporarily disposed in a powder dispensing region of the build station; and 2) at least one printing system adapted to apply a liquid according to a predetermined pattern to incremental powder layers temporarily disposed within build modules in a printing region of the build station;
wherein the conveyor system repeatedly transports the build modules from the powder dispensing region of the at least one powder layering system to the printing region of the at least one printing system to form one or more 3DP articles in the build modules;
b) at least one article (and/or build module) transfer system that transfers completed 3DP articles (and/or build modules), one or more at a time, away from the build region of the 3DP build system;
c) at least one control system that controls operation of one or more systems of the equipment assembly;
d) optionally, at least one liquid removal system; and
e) optionally, at least one packaging system adapted to package one or more 3DP articles at a time.

A build module receives and retains powder deposited therein by a powder layering system. In some embodiments, the build module comprises a height adjustable platform (or lower punch) disposed within a cavity in the upper surface of the build module, wherein the cavity is defined by sidewalls and edges. The height adjustable platform in combination with the sidewalls forms a cavity for the powder. The platform raises or lowers incrementally. Powder is placed within the cavity and onto the platform.

FIG. 37 depicts an exemplary build module (365) comprising a body (361), one or more cavities (362), and height adjuster (364) engaged with and adapted to raise and lower one or more height adjustable platforms (punches) (365) disposed in the respective cavities. A build module can be permanently or removably engaged with the conveyor system. Although the body and cavity of the build module are depicted having a rectangular shape, they can be shaped as needed. In a cavity 3DP system, the top plan view of the cavity approximates the plan view of an 3DP article to be printed in the cavity. The height adjuster can comprise one or more height adjusters. In some embodiments, the height adjuster is incrementally height adjustable thereby rendering the height adjustable platform also incrementally height adjustable. In some embodiments, an incrementally height adjustable component or system is raises by one or more increments before and/or after placement of a layer of powder on a build module and prior to placement of a subsequent layer of powder the build module.

The height of an increment (thus the thickness of an incremental layer) can be controlled in different ways. In some embodiments, the height adjuster is computer controlled, whereby the computer controls raising or lowering of the height adjusting means by the size of an increment and/or by the number of increments. The size (height, vertical displacement) of an increment can vary from incremental layer to incremental layer, be the same from incremental layer to incremental layer or a combination thereof. In some embodiments, the size of the increment is the same for each incremental layer (build lap) of a build cycle, is different for one or more incremental layers of a build cycle, or a combination thereof.

The size of a vertical increment can be relative to a prior initial position of the build platform or the height adjuster of the powder fill head or both. For example, the platform is lowered within the cavity by a first increment to a first position relative to upper surface of the build module. A printed incremental layer is formed on the platform at the first position during a first build lap. The platform is then lowered by a second increment to a second position but relative to where it was at the first position. Another printed incremental layer is formed on the platform while at the second position during a second build lap. This process is repeated until completion of a build cycle.

The size of a vertical increment can be relative to one or more absolute positions of the platform in the cavity of a build module. For example, the build module can comprise plural encoders distributed vertically within or adjacent the cavity. The size of a first vertical increment, then, is defined by the absolute position (absolute vertical distance) of the platform with respect to a first encoder. When the platform is lowered by a second increment to a target second vertical position, which is determined according to or defined by the absolute vertical distance of the platform with respect to a second decoder. This type of absolute positioning can be exemplified as follows. If the target increment is 0.50 mm below the upper surface of a build module, the platform is commanded to drop 0.50 mm. If the next target increment is to be an additional 0.25 mm, then the platform is commanded to drop to a depth of 0.75 mm below the upper surface of the build module rather than to command it to drop by 0.25 mm relative to the initial 0.5 mm increment. This approach is generally superior to using relative moves (0.500, then 0.250) as any minor positioning errors will be resolved or at least not accumulate.

The height of an increment can also be controlled by the relative vertical displacement of the lower and/or upper punch of a punch system. In some embodiments, the upper and lower punches (platform) are lowered the same distance in the same direction, wherein the vertical distance corresponds to the height of the increment. In some embodiments, the upper punch is lowered a first distance and the lower punch is lowered a second distance, wherein the first distance is greater than the second distance such that the difference in distances corresponds to the height of an increment. In some embodiments, the upper punch is lowered a first distance and the lower punch is lowered a second distance, wherein the first distance is greater than the second distance, and both lower and upper punch are subsequently raised such that the height of an increment corresponds to the net change in vertical distance moved by the lower punch. In some embodiments, one or more vertical movements may be made by the upper and lower punches, and the height of the increment corresponds to the relative vertical distance from the top surface of the solid material in the cavity to the height of the top surface of the sidewalls of the cavity. In some embodiments, the height (thickness) of an incremental layer is equal to the vertical distance between the top of the cavity and the top of solid material (i.e. prior powder layer or prior incremental layer) in the cavity.

The height of the platform (or lower punch) within a cavity can be controlled, changed or adjusted with a servo motor or other such means.

The exemplary powder-layering system (381) depicted in FIG. 41 is mounted on a support (table, frame, body, 384) and comprises at least one powder fill head (381), at least one powder reservoir (387) and at least one powder feeder tube (383) driven by a powder feeder drive (384). It transfers powder from the powder reservoir to the powder fill head. The powder feeder tube can comprise a drive motor and screw-type shaft, e.g. an auger or shaft with spiral blades/vanes, such as found in a Schenk feeder. The powder-layering system supplies powder to, and optionally forms, the incremental powder layer when a build module passes through the powder dispensing region (386, also referred to as a layering region).

In some embodiments, a powder fill head comprises a powder fill head body, at least one powder fill head hopper and at least one powder spreader. The hopper receives material from the powder feeder tube to form a temporary supply of powder, which is optionally agitated by powder fill head agitator, which can be a powder fill head distribution plate instead. In some embodiments, the hopper is replaced with a chute (not shown, or distribution plate) having a channeled interior surface that distributes powder evenly across the width of the surface and downward onto a build module. In some embodiments, the powder fill head further comprises at least one powder-height controller adapted to control the relative distance between the powder spreader and a surface (such as the upper surface of the build module, the height adjustable platform, or a prior powder layer) below the powder spreader. An optional distribution bar (or plate, not shown) can be placed between the outlet of the fill head body and the powder spreader (roller). The distribution bar serves to better distribute powder across a layer of powder prior to being contacted by the powder spreader, whereby an incremental powder layer is formed.

The powder-height controller can raise or lower the powder spreader so as increase or decrease the thickness of a layer of powder placed onto the platform (lower punch) or a prior layer of powder on the platform. For example, if the platform (lower punch) is lowered by a first increment and the powder-height controller is raised by the same or another second increment, then the thickness of powder laid down will approximate the sum of the first and second increments. If the platform is lowered by a first increment and the powder-height controller is lower by a second increment, then the thickness of powder laid down will approximate the difference of the first increment minus the second increment. Alternatively, the powder spreader in combination with the powder-height controller can cooperate to compress a layer of powder that has been previously laid down. This can be accomplished by first laying down a layer of powder having a first thickness during a first build lap, lowering the powder-height controller and powder spreader and then passing the layer of powder under the lowered powder spreader thereby compressing the layer of powder.

In some embodiments, the powder spreader is a cylindrical roller the axis of which has a radial direction of motion opposite the linear direction of motion of a build module through the powder layering system. For example, the surface of the cylinder has a first linear direction opposite the second direction by which an underlying build module passes under the cylinder. In some embodiments, the powder spreader is a cylindrical roller, bar, rod, plate or straight smooth edge. Powder fill heads of other construction can be used.

The amount or rate of powder discharged from the powder fill head can be regulated with one or more controls. A powder discharge feedback controller can monitor the accumulation of powder at the powder spreader as the powder is being discharged from the powder fill head and spread to form an incremental powder layer. If the rate at which powder is released is too fast, an excessive amount of powder will accumulate at the powder spreader possibly causing it to spread the powder improperly. The feedback controller then sends a signal thereby causing the rate of powder discharge from the powder fill head to decrease. Conversely, if the feedback controller senses that the rate of powder discharge is too slow, it sends a signal thereby causing the rate of powder discharge to increase. The feedback controller can employ one or more visual, laser, acoustic or mechanical sensors or a combination thereof. Other control approaches may be used, such as gravimetric control from a source of powder supply, either alone or in conjunction with the approaches above.

A conveyor module comprises a body, engagement means (male and/or female) and one or more build module engagement means adapted to removably or permanently engage build modules. In some embodiments, adjacent segments (modules) of the conveyor are pivotally engaged by means of engagement means such that the segments can pivot about an axis. Although engagement means can be a hinge-type joint, other engagements can be used.

FIG. 42 depicts a perspective view of a powder layering system (390) depositing bulk powder into the individual cavities (394) of a build module comprising plural cavities. Bulk powder is charged into the hopper (391) by means of a conduit (392). The layering system deposits powder into the cavities, but the system can optionally further comprise a powder removal system that removes excess powder from the upper surface of the build module, thereby leaving behind loose powder only in the cavity(ies) of the build module.

FIG. 43 depicts a top plan view of a partial build station comprising a powder fill head (397) and a print head (399) below which is a conveyor module (395) and corresponding build module (396) moving in the direction of Arrow Q1 through a powder dispensing region and a printing region, respectively. The fill head, which is disposed transverse to the direction of motion of the build module, which comprises plural cavities, remains transversely and longitudinally stationary (with respect to the plane defining the upper surface of the build module, even though it can move vertically toward or away from said plane) as it places an incremental layer of powder (401) into and across the width of one or more cavities. The fill head (397) comprises a spreader (398 depicted in dashed line) and hopper. The build module moves in the direction of Arrow Q1, whereby it passes through the printing region beneath the print head (399) and print module (400), which are disposed transverse to the direction of motion of the build module. The print head remains transversely, longitudinally and vertically stationary with respect to the plane defining the upper surface of the build module. The print module applies liquid onto the incremental layer of powder according to a predetermined pattern, thereby forming an incremental printed layer (402) in respective cavities. The exemplary print head comprises a single print module (400; depicted in dashed line) that spans the width of a cavity of the build module.

FIG. 38 depicts an exemplary printing system that applies liquid (binding fluid) to a powder layer in the printing region of the printing system. In some embodiments, the liquid is applied according to a Cartesian coordinate system or according to a polar coordinate system (radial system, cylindrical coordinate system, circular coordinate system, or spherical coordinate system). An exemplary printing system comprises at least one print head (372), which deposits liquid onto an incremental layer of powder in a build module, and at least one liquid feed system that conducts liquid from one or more liquid reservoirs to the at least one print head. In some embodiments, the printing system comprises plural print heads, plural liquid feed systems, plural reservoirs or a combination thereof. In some embodiments, the printing system comprises a single print head, plural liquid feed systems, and plural reservoirs.

The print head of FIG. 38 directs a stream of droplets of liquid into a printing region (374) through which build modules pass. The exemplary system comprises a frame or gantry (371) by way of which the print head (372) can translate/move in the direction of Arrow D1, which is transverse to the direction of motion of a build module during printing. The printing system can be mounted to a support (373). Translation of the print head can be performed manually or via computer controlled operation. In some embodiments, the print head is stationary when applying liquid onto an incremental layer of powder, meaning that as liquid is being applied to a powder layer during a print lap, the print head (in particular the print modules) does not move in a direction which is transverse, with respect to the build plane, to the direction of motion of a build module during printing, i.e. during the application of liquid. Such a means of printing is different than prior systems wherein the print head (in particular the print module(s)) moves back and forth, in a direction which is transverse to the direction of motion of a build module, during printing.

A print head can comprise one or more print modules that deposit the liquid onto a layer of powder. The print head can comprise plural print modules that form corresponding printing regions. When a print head comprises plural print modules, the arrangement/layout of the print modules can be as needed. The print head (375) of FIG. 39 comprises plural print modules (376) arranged in plural columns with each column comprising plural print modules. A powder can pass across the print modules in the direction of Arrow E1 such that the print direction is transverse to the horizontal shape of the print module.

Other suitable arrangements for the print modules are depicted in FIG. 40. The print head (379) comprises a single print module. The print head (380) comprises four print modules pared in groups (380a, 380b) of two offset horizontally from one another. The print head (378) is somewhat similar to head (380) except that the print modules (380a, 380b) are wider horizontally and offset to a greater extent horizontally than are the print modules (378a); moreover, the print modules are horizontally offset from one another. The print head (377) comprises two linearly and transversely offset groups (377a, 377b) of print modules. When viewed in the direction of Arrow E1, the adjacent edges of the two groups overlap (each group overlaps the dashed line).

By offsetting the print modules as depicted for module (378), the apparent overall print resolution of the print head can be increased. The print modules can be offset in staggered, interlaced, sabered, or angled arrangements relative to the print head in order to increase overall print density/resolution. For example, if the print resolution of each print module is 75 dpi (drops per inch), then the apparent overall print resolution of the print head (378) can be 75 dpi, 150 dpi, 225 dpi, 300 dpi, 375 dpi, 450 dpi or even higher. If the print resolution of each print modules is 100 dpi, then the apparent overall print resolution of the print head (378) can be 100 dpi, 200 dpi, 300 dpi, 400 dpi or even higher. In some embodiments, the print resolution of the print head is the same as or greater than the print resolution of a print module comprised within the print head. In some embodiments, the print resolution of the print head is a multiple of the print resolution of one or more print modules comprised within the print head. In some embodiments, the print resolution of the print head is the less than the print resolution of a print module comprised within the print head.

The arrangement of one or more print modules in the print head can be modified as needed to provide the desired printing result. The print head (405) depicted in FIG. 44A comprises four print modules (406) arranged in both transverse and longitudinal displacement (with respect to the direction of motion of the print head). Together the four print modules span the width of the cavity of the build module. The embodiment (407) of FIG. 44B differs from that of FIG. 44A in that the four print modules (408) are only transversely displaced but not longitudinally displaced.

In some embodiments, the one or more print heads is/are stationary when applying liquid onto an incremental layer, i.e. when printing. The one or more print heads can, in particular, be transversely and longitudinally stationary, with respect to the linear direction of motion of a build module (and thus an incremental layer of powder), when printing. Particular embodiments include those wherein: a) the printing is performed according to a Cartesian coordinate algorithm; b) the build module moves during printing in a linear direction that is perpendicular to the disposition of the print module (and one or more print heads); c) the print head and one or more print modules are stationary when printing (when applying liquid to an incremental layer of powder) and do not move in a direction that is transverse or longitudinal with respect to the direction of motion of the build module; and/or d) printing is performed according to a polar coordinate algorithm.

The three-dimensional printing system/assembly of the invention employs Cartesian coordinate and/or polar coordinate based printing system and algorithms. Unlike other systems that move the print heads transversely and/or longitudinally when printing, the print heads of the invention can be (but need not be) substantially stationary during printing. The term "transversely" is determined in relation to the direction of motion of a build module beneath a print head and means substantially perpendicular to the direction in which a build module is conducted through a printing area. The term "longitudinally" is determined in relation to the direction of motion of a build module beneath a print head and means substantially parallel to the direction in which a build module is conducted through a printing area. Application of liquid across the width of powder layer beneath a print head is accomplished by employing one or more print modules that individually or together traverse at least 75%, 80%, at least 85%, at least 90%, at least 95%, at least 97.5% or at least 99% the width of the powder layer. In the present case, the "width" of the powder layer is determined along a direction transverse to the direction of motion of a build module beneath a print head, and the term "length" is determined along a direction parallel to the direction of motion of a build module beneath a print head. In other words, a single print head can traverse the width or plural print heads transversely adjacent to each other can traverse the width of the powder layer.

In particular embodiments, the print head comprises plural print modules that individually do not, but together do span the width of an incremental powder layer and/or of the cavity of a build module. In some embodiments, one or more print modules together span at least 50%, at least 55%, at least 75%, at least 90%, at least 95%, at least 99% or all of the width of the cavity of the build module. In particular embodiments, the build module moves in a first direction, and the print head is stationary when liquid is being applied to the incremental powder layer. In particular embodiments, printing is performed primarily or solely according to a Cartesian coordinate algorithm. For example, the algorithm controls application of the droplets of the printing fluid relative to the linear (non-radial, straight) direction of the conveyor such that the print head applies droplets in a direction that is parallel (longitudinal) or is perpendicular (transverse) with respect to the linear direction of motion of the conveyor. The conveyor and corresponding build modules only move in a straight linear direction beneath the print head and build head.

An alternate embodiment of the invention is depicted in FIG. 44C, wherein the print head (409) comprises one or more or plural print modules that do not span the width of an incremental powder layer and/or of the cavity of a build module. This print head is either stationary when printing (when applying liquid to an incremental layer of powder) or moves transversely, with respect to the direction of motion of the build module, while applying liquid to the powder. The print modules of the print heads (377, 378, 380, 409 of FIGS. 40 and 44C) are arranged such that the jets on multiple print heads are interleaved to increase the print density across the print bed. For example, individual print modules having a native print density of 100 dpi are interleaved together such that four of the print heads together provide a 400 dpi print density.

In some embodiments, clusters of print modules, such as depicted in FIG. 44D, are arranged so their overall span covers only part of the width of a powder layer, such that plural print heads (each containing a cluster of print modules with interleaved jets) are required to cover the full width of the powder layer. For example, three print heads (410), each having a cluster of print modules which together spans only 2.5", would need to be arranged in a horizontally offset manner in order to cover the width of a powder bed or layer that is between 5 to 7.5 inches wide.

The at least one printing system can apply liquid according to any predetermined print pattern or randomly onto an incremental layer of powder. The pattern can be the same from incremental layer to incremental layer or can be different for one or more incremental layers of a printed article. Generally, two adjacent print patterns (i.e., vertically neighboring within the same 3DP article design) will comprise at least two overlapping printed portions such that at least a portion of the printed/bound powder in one printed incremental layer will adhere (be bound) to at least a portion of the printed/bound powder of an adjacent printed incremental layer as one is formed atop the other. In this manner, plural stacked adjacent printed incremental layers adhere to each other thereby forming a three-dimensionally printed article comprising plural adjacent printed incremental layers of completely or partially bound powder. Even though a three-dimensionally printed article can include undercuts, overhangs, cavities, holes and other such features, at least part of the printed portions of adjacent printed incremental layers must adhere to one another in order to form and fill the composite volume of the article.

The printing system employs Cartesian coordinate-based and/or polar coordinate-based printing algorithms when applying liquid to an incremental powder layer. The system includes a computer and associated software that comprises one or more print jobs. A print job includes, among other things, information on the thickness of incremental layers and the predetermined pattern to be printed on the incremental layers of a printed article. The print job provides layer-by-layer instructions to the print head (print module(s)) about the creation and placement of droplets of liquid onto the incremental powder layer. The print job is based upon the series of two-dimensional images (slices) that, when stacked, together form a predetermined three-dimensional image (object).

Without being held bound to a particular mechanism, a target three-dimensional article is designed, such as with a CAD program. A virtual image of the target article is sliced virtually into plural stacked thinly-sliced images (which are referred to herein as "two-dimensional" images), wherein each two-dimensional image is actually the thickness of an incremental powder layer. The sum total of thicknesses of the image slices equals the total "height" of a target article. Each two-dimensional "image" is then converted into a subset of printing instructions, which together define a predetermined printing pattern for that image. All of the subsets of printing instructions are joined together to form a final set of printing instructions that are used by the computer to control printing. Aside from incremental layer thickness, two-dimensional shape of predetermined patterns, and shape of target article, the final set of print instructions also includes specification of or consideration of linear speed of the build module beneath the print head, rate of application of liquid to incremental powder layers, length and width of the incremental powder layer, dimensions of the cavity of a build module, incremental height adjustment of the height adjustable platform of the build module, rate of loading of powder into the powder fill head, rate of loading of powder into a build module to form an incremental layer, rate of transfer of powder from a feed reservoir to the fill head, resolution of the two dimensional image to be printed on each incremental layer, the number of applications of liquid to each incremental layer, application of one or more specific liquids to one or more specific locations of the incremental layer, starting and stopping of liquid application with respect to each build module, the number of articles to be printed, the number of build modules in the equipment assembly, the number of build modules to be printed upon, rate at which the platform of the build module moves down, timing for starting and stopping powder delivery relative to the entire build cycle, rotational speed of leveling device (roller) and other such parameters.

An equipment assembly comprises a control system comprising one or more controllers. Without being held bound to a particular mechanism, a homing switch located at a fixed point of the conveyor provides a reference point as to the location of the "first" build module in a group of build modules. From there, a computer is able to determine the location of the rest of the build modules in that group by knowing the size of the conveyor, the spacing of the build modules and the dimensions of the build modules. The control system can also comprise a proximity sensor that specifies the location of one or more build modules relative to the conveyor. The control system comprises a synchronizer that facilitates synchronization of operation of the various components of the equipment assembly. By taking into consideration the track (linear) speed of the conveyor and the target thickness and width of an incremental layer, a computer is able to instruct the powder layering system to charge powder onto the build modules at a certain feed rate. After part of a lap or after one or two calibration laps, the powder feed rate can be continuous. Once a proper incremental powder layer is formed, deposition of liquid onto the incremental layer can begin. A proximity sensor senses the leading edge of a build module and then sends instruction to the print system. A computer controlling the print system takes into consideration a set of printing instructions (which can include among other things the target print resolution (density), the image(s) (pattern(s)) to be printed on the incremental layer, the target rate of liquid deposition, the number of liquids to be deposited, the dimension of the print head and print modules, track speed, the set of images (patterns) that are to be printed to form a target 3D printed article, target article porosity or density, or other such parameters) and the signal generated by a wheel encoder, for example, to provide a pulse that sets the print rate at which to consume the image files in the printing instructions and the resolution at which to print the image file(s). Following completion of layering and printing per the printing instructions, a build cycle is completed.

As described herein, the powder system can comprise one or more feedback controllers that determine the proper powder feed rate into a powder feeder and into the build modules. Likewise, the printing system can comprise one or more feedback controllers that determine the rate at which printing fluid (liquid) is being applied and/or consumed and can therefore control the liquid application rate and can also the reloading of liquid reservoir(s).

A liquid removal system, such as a dryer, can comprise one or more relative humidity controllers, temperature controllers and conveyor speed controllers. The system is therefore capable of adjusting drying time and conditions to provide printed articles containing the desired level of moisture. The liquid removal system may use one or more heat transfer mechanism such as conduction, convection, or radiation.

In some embodiments, one or more components of the equipment assembly are computer controlled. A controller is independently selected at each occurrence from a computerized controller, electronic controller, mechanical controller or a combination thereof. In some embodiments, the control system comprises one or more computerized controllers, one or more computers, one or more user interfaces for one or more computers. In some embodiments, one or more components of the three-dimensional printing build system are computer controlled. In some embodiments, the conveyor system, the height adjustable platforms of the build modules, the at least one powder layering system and the at least one printing system are computer controlled. In some embodiments, the equipment assembly is adapted to spread layers of powder and print droplets of liquid in a predetermined pattern according to instructions provided by a computerized controller. In some embodiments, the predetermined pattern is based on one or more two-dimensional image files comprising pixels. In some embodiments, the two-dimensional image files are structured such that certain pixels indicate dispensing of droplets, and other pixels represent no dispensing of droplets. In some embodiments, the two-dimensional image files include different colors of pixels to indicate dispensing of different liquids, or no dispensing of liquid.

Figure 47:
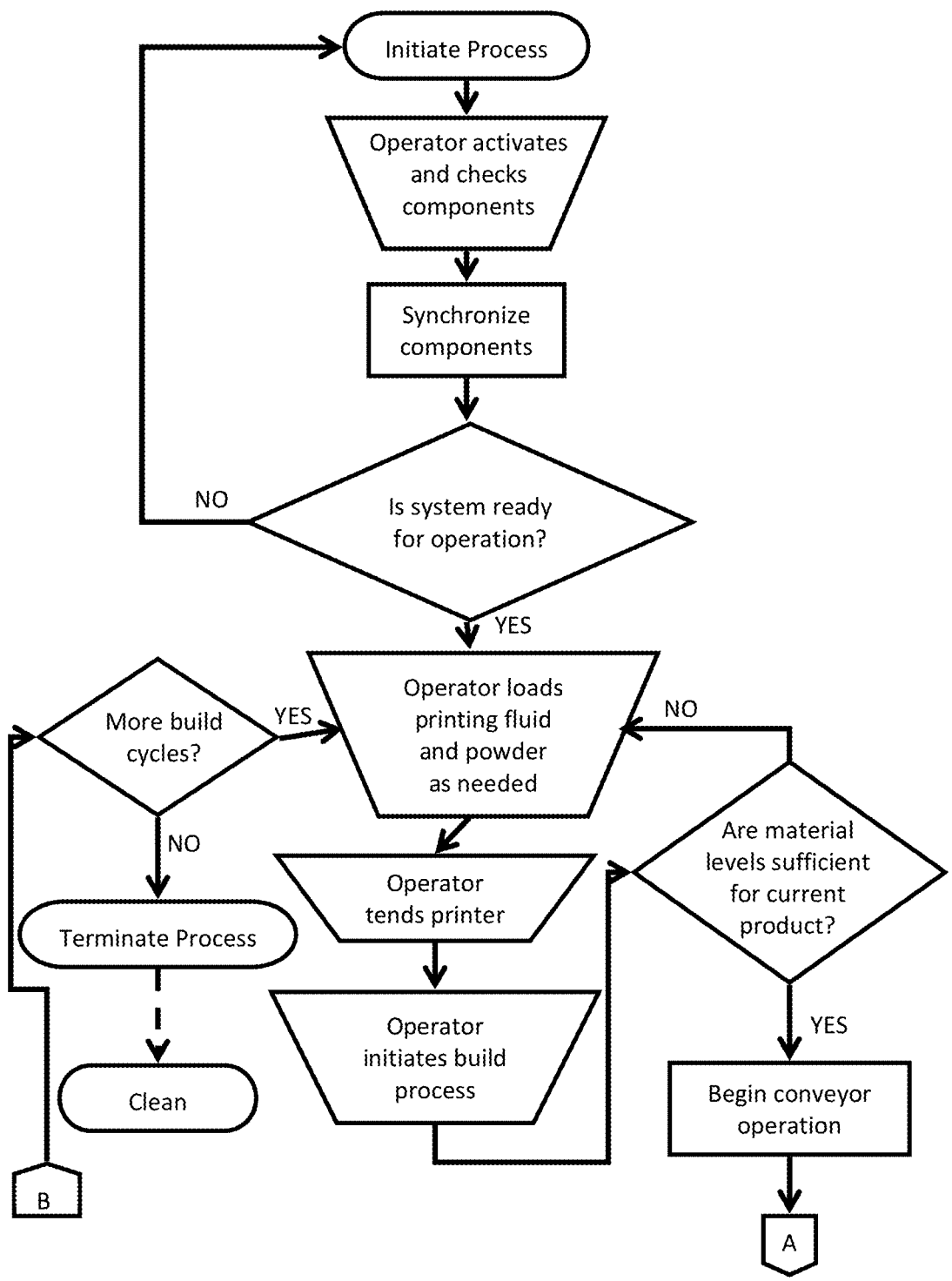
FIGS. 47-49 together depict an exemplary logic flow for operation of the equipment assembly of the invention.
Figure 48:
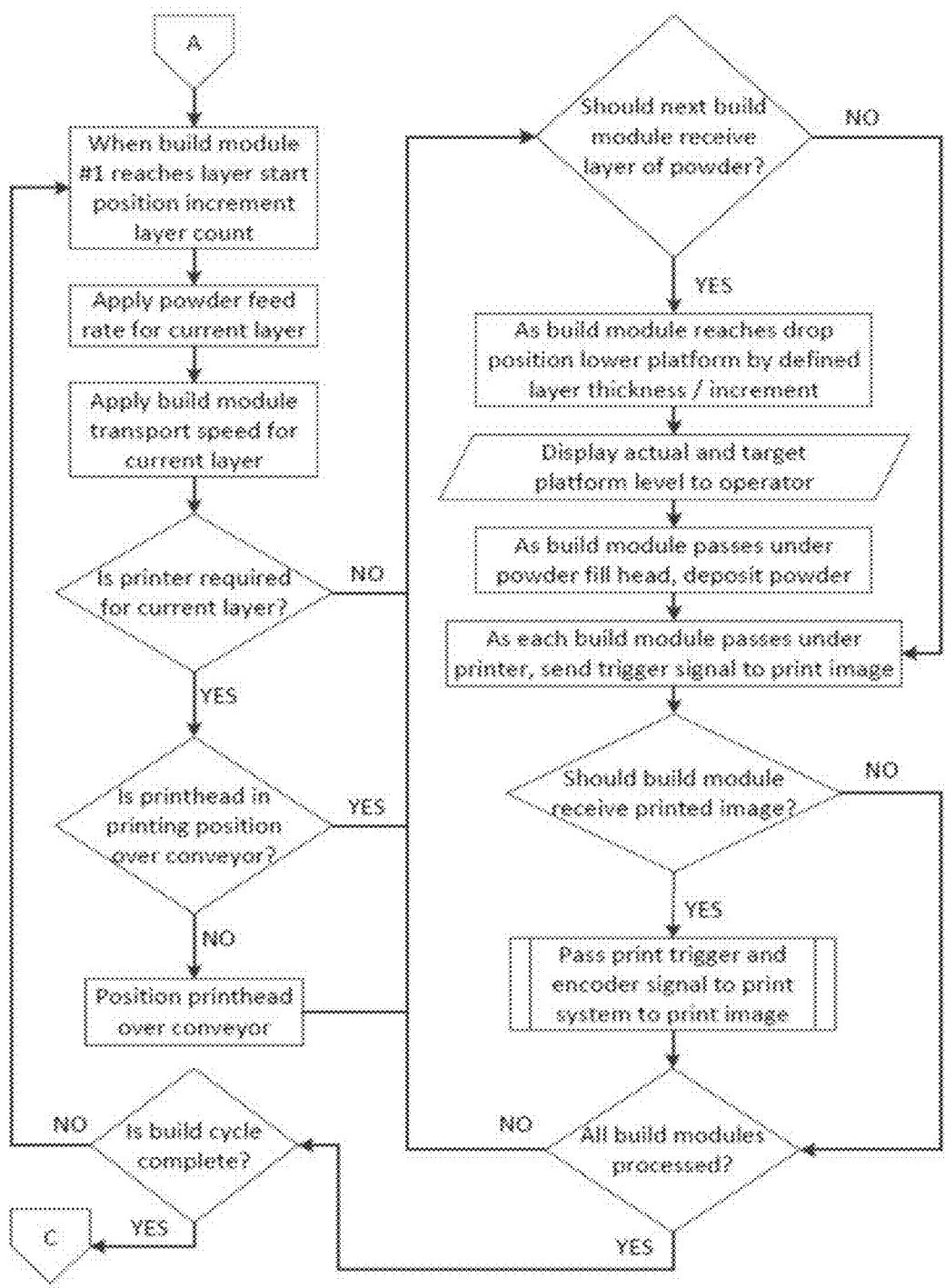
Figure 49:
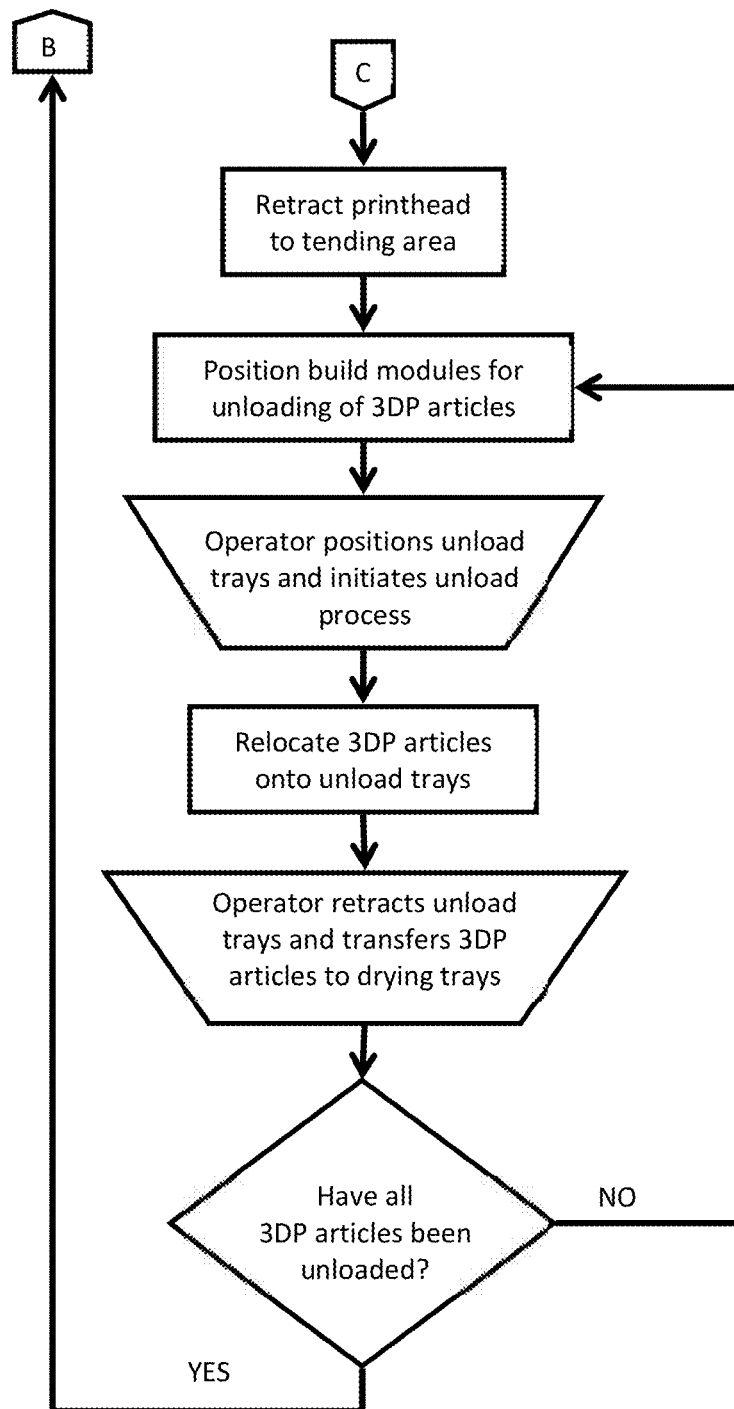

FIGS. 47-49, depict a flow chart for operation of an exemplary embodiment of the invention. The process is initiated, e.g. by an operator or electronic component such as a computer. An operator activates and checks the status of system and assembly components, which are then synchronized, after which time the system (assembly) is ready for operation. Printing fluid and powder are loaded into their respective systems as required of the product to be three-dimensionally printed. The level of printing fluid(s) and powder(s) are checked and when the required amount is present, conveyor operation is initiated.

Moving to FIG. 48, the powder feed rate and transport speed (conveyor speed) for the build module is applied and a query is made to determine whether or not a build module is supposed to receive powder. If so, the platform is lowered and a layer of powder is deposited onto the build module as it passes under the powder fill head. If not, the build module does not receive powder. A query is then made to determine whether or not the powder layer is supposed to receive a printed image. If so, a two-dimensional pattern is printed onto the layer as the build module passes under the print head. If not, the build module does not receive printing solution. A query is made to determine whether or not all of the build modules mounted on the conveyor have been processed, i.e. whether or not the build lap is completed or whether or not the build module is supposed to receive another layer of powder. If not, any unprocessed build module is processed. If all of the build modules have been processed, i.e. the build lap is complete, a query is made to determine whether or not a build cycle is complete. If not, one or more additional build laps are conducted. If so, the build modules are prepared for unloading of 3DP articles (and/or build modules) as described in FIG. 49. Completed 3DP articles are unloaded and transferred to a drying system. After all 3DP articles have been unloaded, a query is made according to FIG. 47 to determine whether or not additional build cycles will be conducted. If not, the process is terminated. If so, the next build cycle process is initiated.

Figure 50:
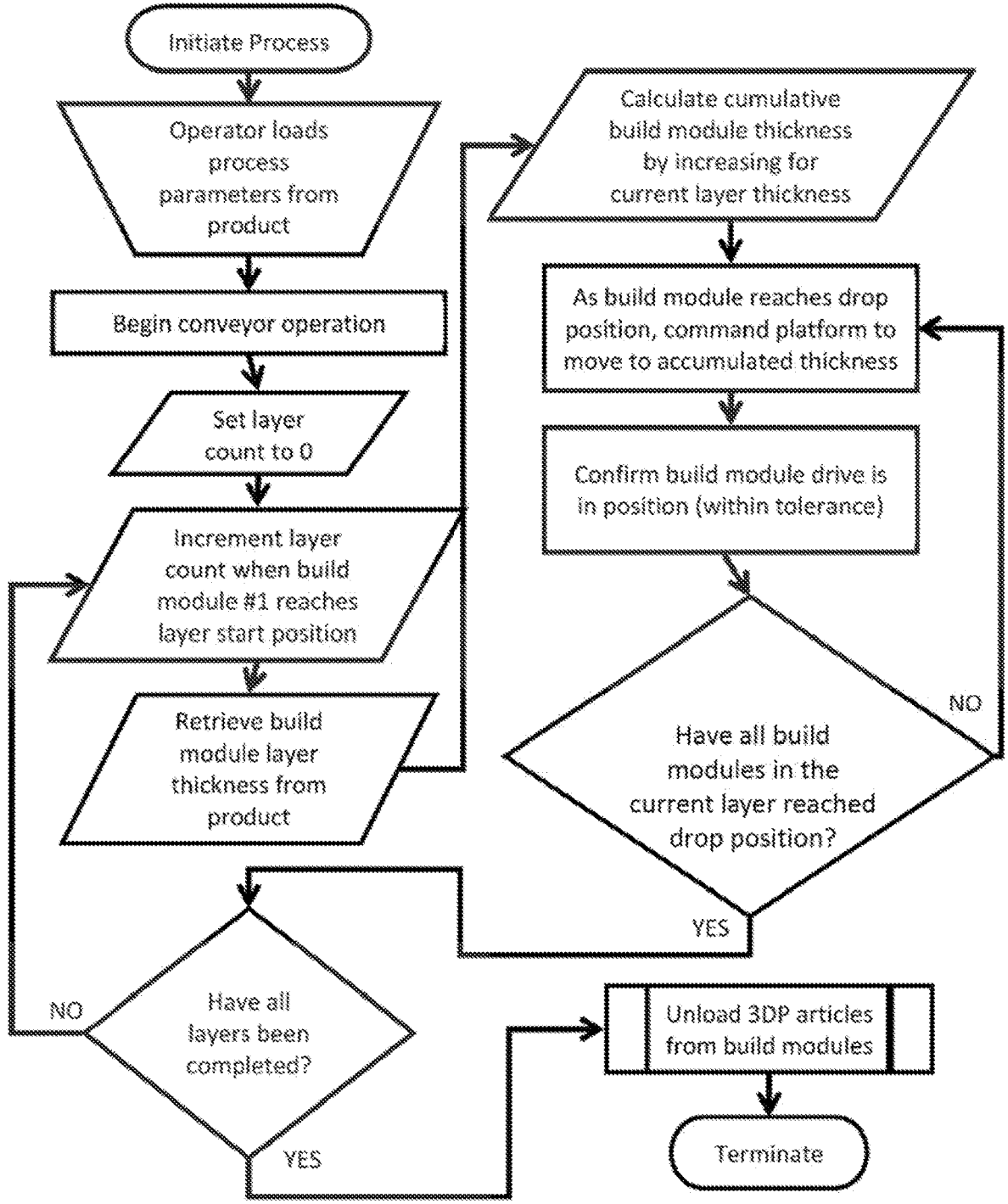
FIG. 50 depicts an exemplary logic flow for operation of the powder layering system.

FIG. 50 depicts an exemplary subroutine detailing how the platform layer increment is controlled within a build lap and a build cycle. In this example, the layer thickness (increment) is provided by a product definition. A cumulative thickness is calculated according to the number of powder layers already laid down. The platform (punch) is dropped to the calculated thickness and a determination is made to confirm that it is at the correct position within a predefined tolerance. A query is then made to determine whether or not the platform of all the build modules in a particular build lap have dropped to the correct position. If not, the platforms are adjusted as required. If so, a query is made to determine whether or not all layers of a build cycle are complete. If not, the process of this figure is repeated for each of the build layers as needed until the build cycle is complete.

Figure 51:
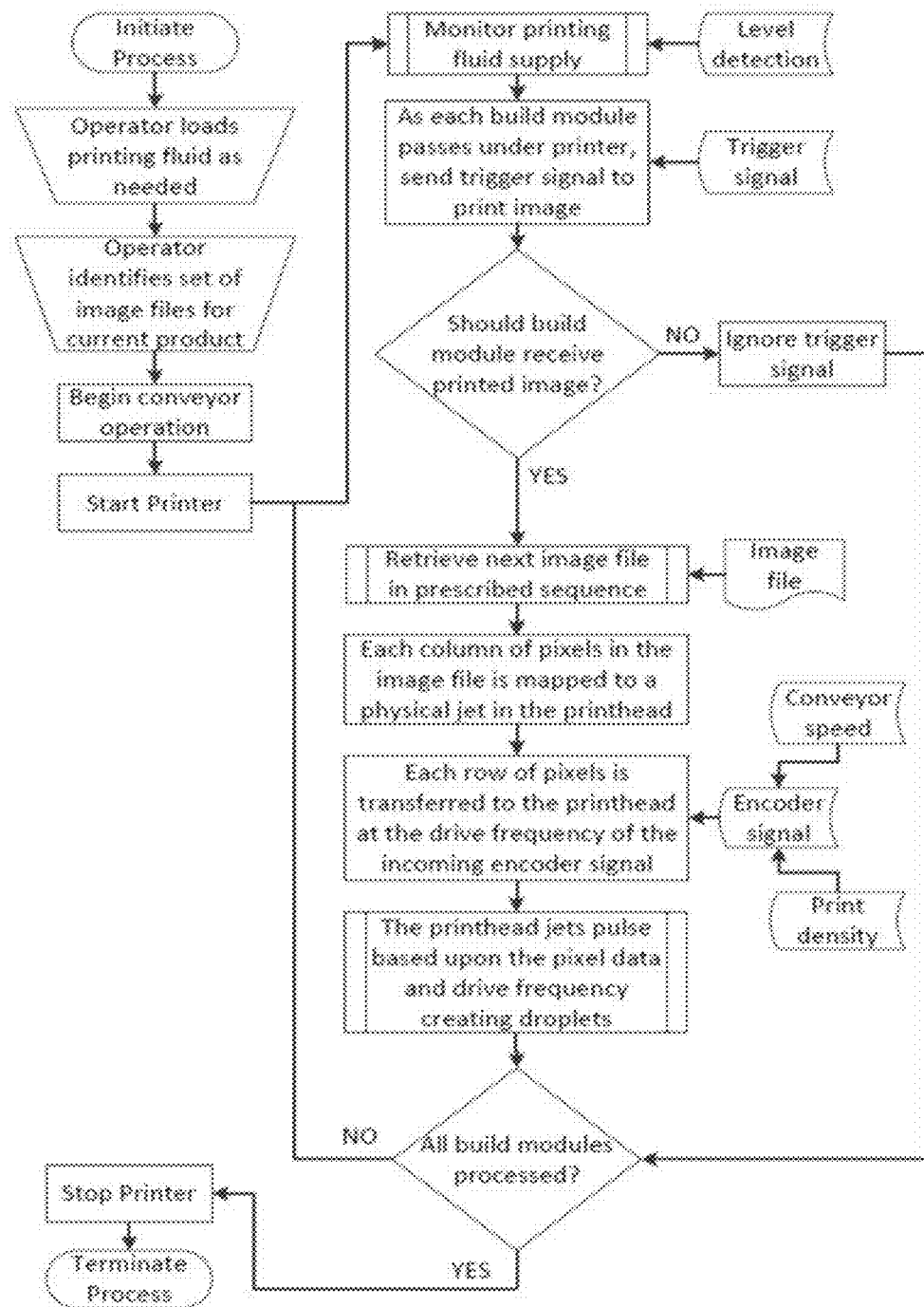
FIG. 51 depicts an exemplary logic flow for operation of the printing system.

FIG. 51 describes an exemplary subroutine detailing operation of the printing system. A build process is initiated and the necessary amount(s) of printing fluid is loaded into the reservoir(s). A set of image files are identified and conveyor operation is begun. During operation, the level of printing fluid(s) is monitored so that it can be replenished as needed. When a build module passes beneath a printhead, a trigger signal is generated prompting a query to determine whether or not the build module is to receive a printed image. If not, the trigger signal is ignored. If so, a print image file is received and processed such that the columns of image pixels (pixels that are aligned along the axis of movement of the build module) are assigned to specific jets of the printhead. In addition, rows of image pixels are sent to the printhead taking into consideration the linear speed of the conveyor and the intended print density of the image to be printed. The printhead then delivers printing fluid droplets, as per the printing instructions, to the powder layer on a build module. A query is then made to determine whether or not all build modules have been processed. This query can be repeated for the build lap and/or build cycle level. Upon completion of a build cycle, the process can be terminated. If needed, the printhead can be retracted and cleaned.

Figure 52:
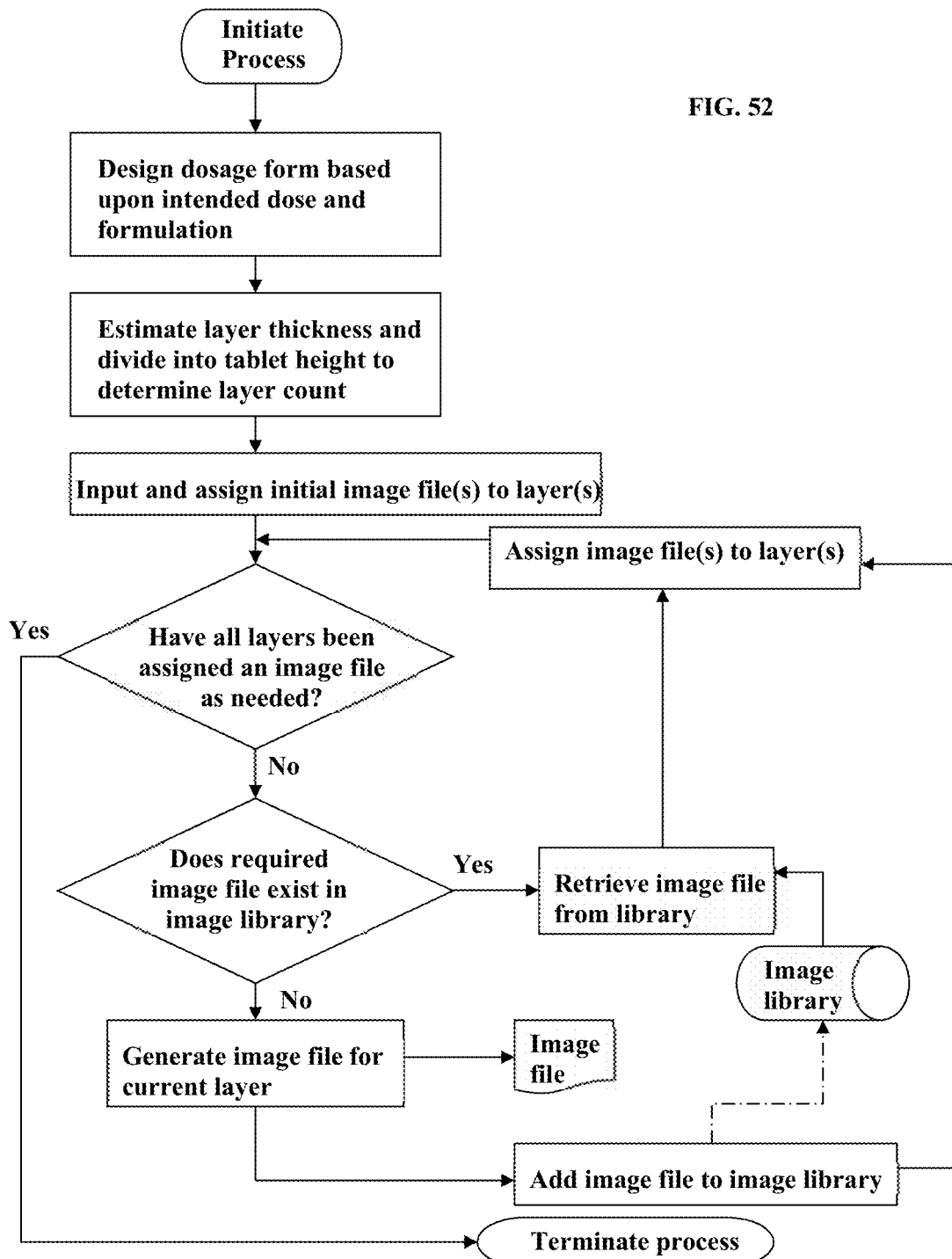
FIG. 52 depicts an exemplary logic flow for design of a dosage form.

FIG. 52 depicts a flow chart of an exemplary process for designing a dosage form and determining the layer thickness thereof and image files (two-dimensional printing patterns) there for. The process can be conducted with or without a computer. A dosage form having a specified three-dimensional structure and comprising a target dose of drug is designed. The approximate target powder layer thickness is selected and the height of the dosage form is divided by the target incremental powder layer thickness to provide the number of powder layers required to prepare the dosage form. Based upon the layer and its location within the dosage form, each layer is assigned as needed an initial two-dimensional pattern, i.e. an image file, which ultimately results in a set of printing instructions employed by the printing system to create a corresponding printed increment layer. The image file assigned to each layer can be input, or it can be retrieved from an image library. In order to determine whether or not archived images from the image library are required, the system queries whether or not all layers have been assigned an image file as needed. If so, the design of the dosage form is complete and the process is terminated. If not, the system queries whether or not the image required for a specific layer exists in the image library. If so, the image file is retrieved from the library and assigned to the respective powder layer. The system then again queries whether or not all layers have been assigned an image file as needed and the loop of logic continues as needed until completion of design of the dosage form. If the image file is not present in the image library, a new image file is created, optionally stored in the image library, and assigned to the respective layer, and the loop of logic continues as needed until completion of the dosage form design. It should be understood that one or more layers might not require any image file at all, meaning that specific layer would not be printed during preparation of the dosage form.

Figure 53:
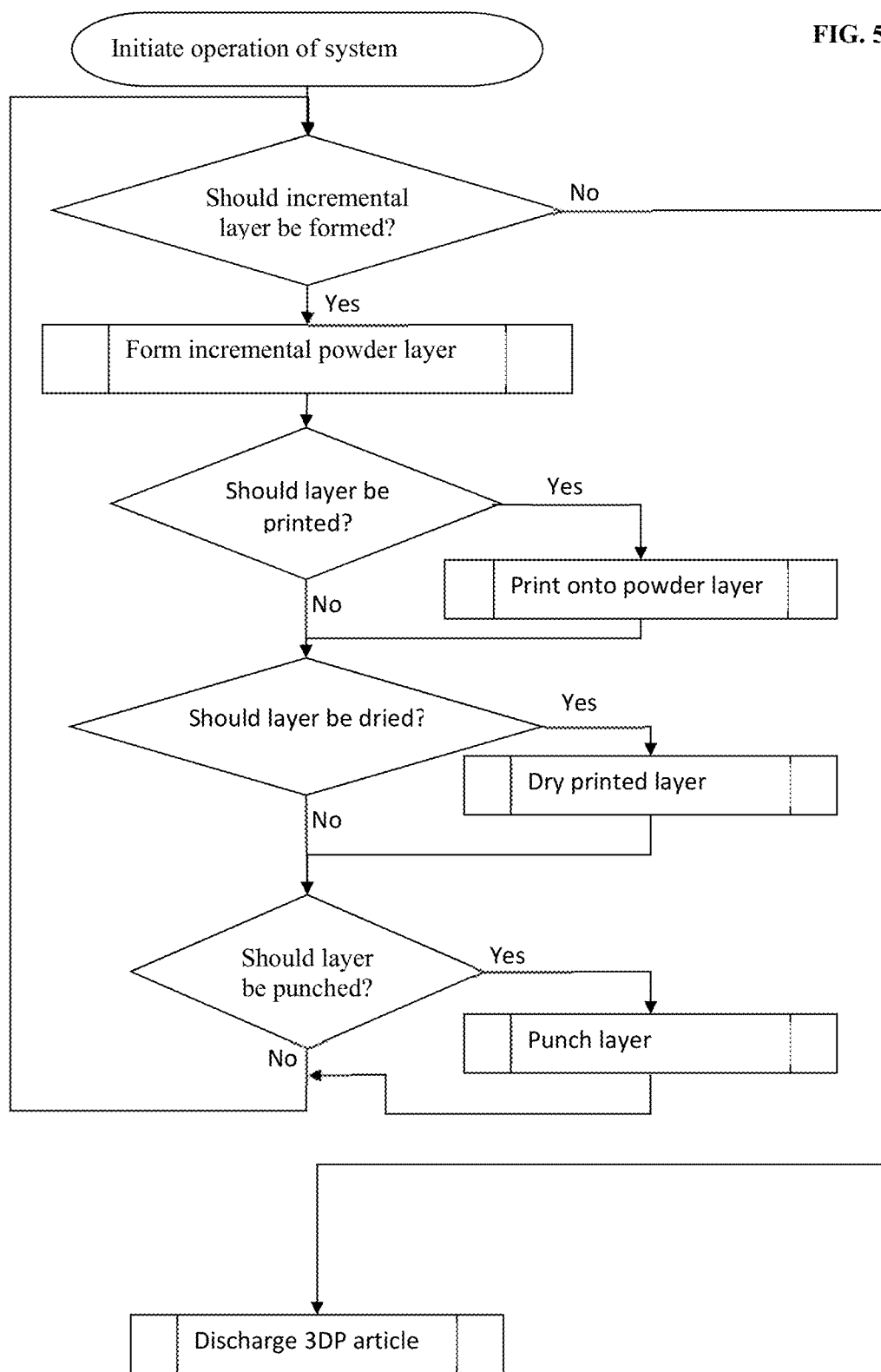
FIG. 53 depicts an exemplary logic flow for general operation of a 3DP system with an in-process layer punch system and in-process layer drying system.

The a generalized flow chart for operation of a 3DP system comprising an in-process punch system and in-process drying system is depicted in FIG. 53. The system determines if an (another) incremental layer should be formed. If not, the build operation is terminated and the 3DP article is discharged. If so, the system forms a powder layer in a receptacle and determines if binding fluid should be deposited (printed) onto the powder layer. If so, it deposits the binding fluid and continues the build operation. If not, it continues the build operation and determines if the layer should be dried with an in-process drying system. If so, it dries the layer and continues the build operation. If not, it continues the build operation and determines if the layer should be punched. If so, it punches the layer and continues the build operation. If not, it determines whether or not an (another) incremental layer should be formed. This operation loop continues until no more incremental layers are to be formed.

Figure 54:
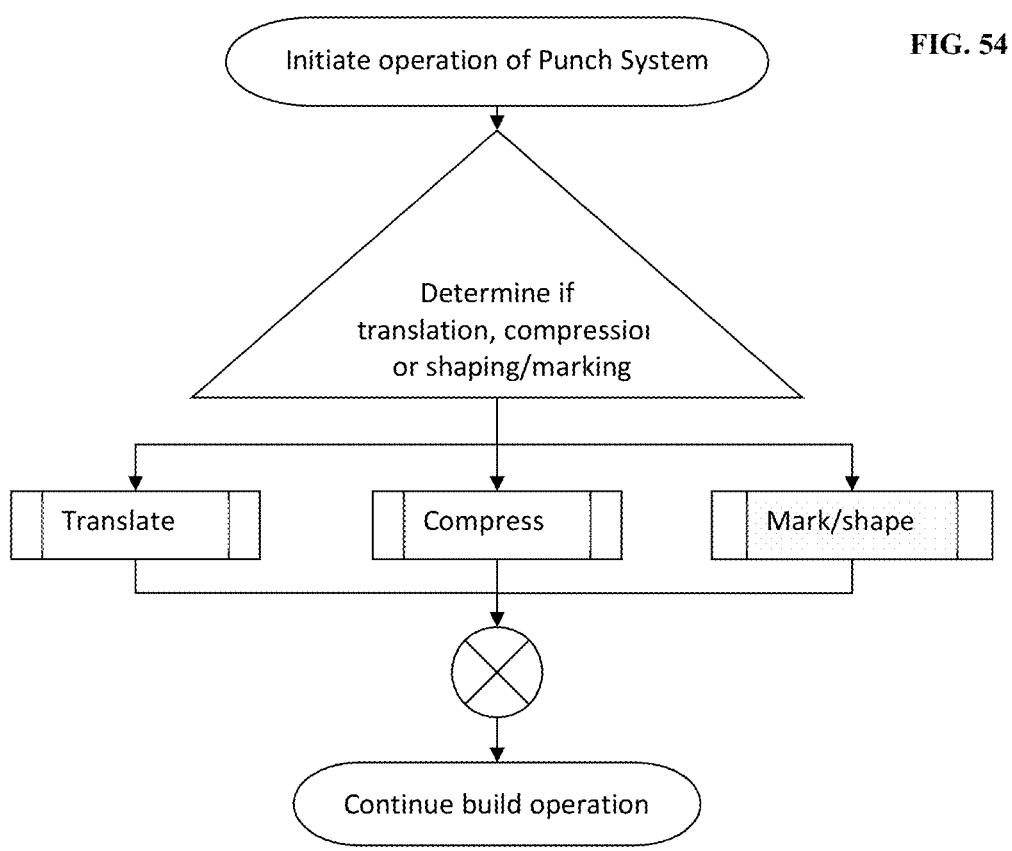
FIG. 54 depicts an exemplary logic flow for operation of the punch system depending upon which operation the punch system is to conduct.

If one or more layers are to be punched in-process, the generalized flow chart of FIG. 54 can be used for overall operation of the punch system. Here, the system determines whether the layer(s) should be translated, compressed, marked or shaped. Following completion of one or more of those operations, the build operation is continued.

Figure 55:
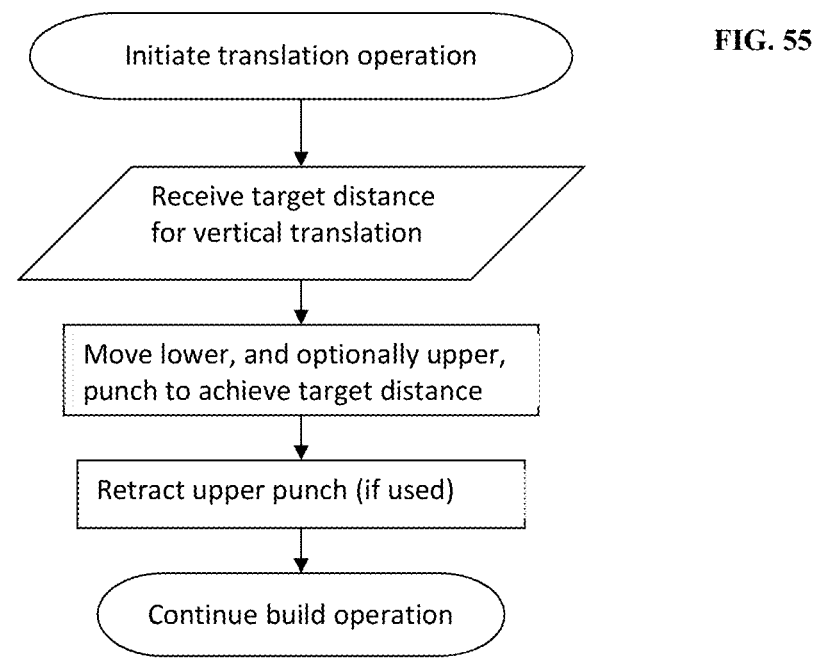
FIG. 55 depicts an exemplary logic flow for conducting a translation operation with a punch system.

A generalized flow chart for operation of the punch system during translation is depicted in FIG. 55. The punch system receives information containing the target vertical distance that the layer(s) is(are) to be translated within a cavity. The lower (and optionally the upper punch) are then moved the target vertical distance to translate the layer(s) in the cavity. The upper punch, if it was used, is retracted vertically, and the build operation is continued.

Figure 56:
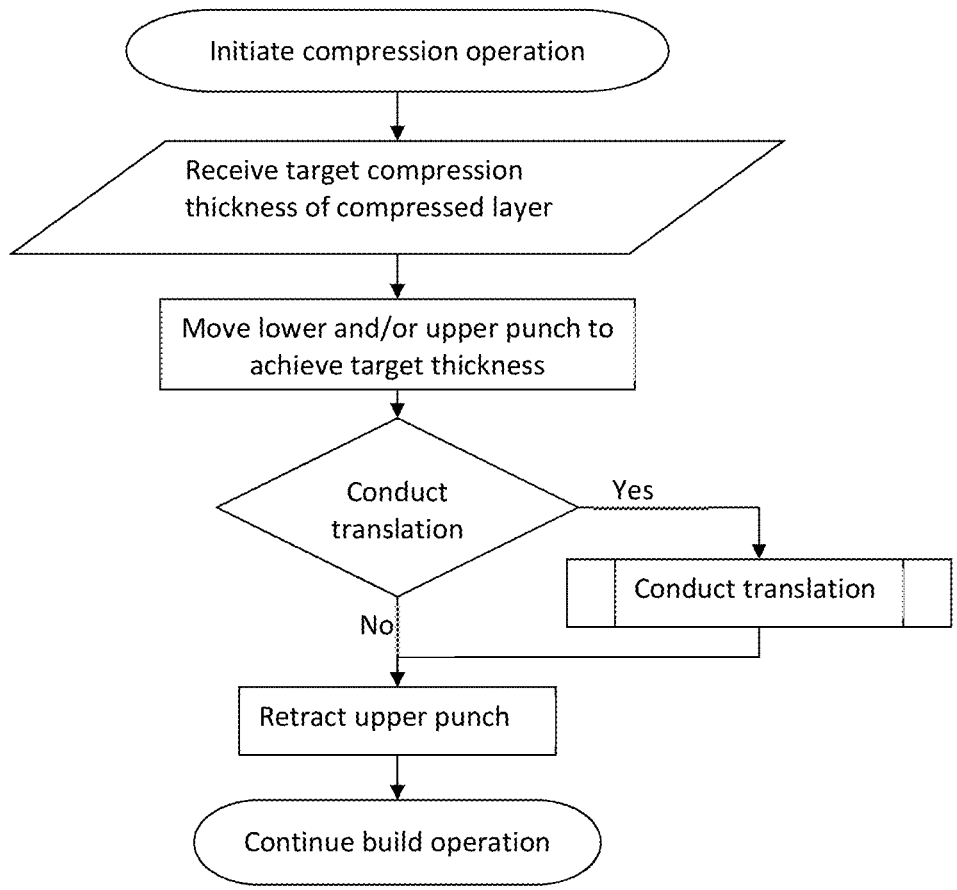
FIG. 56 depicts an exemplary logic flow for conducting a compression operation with a punch system.

A generalized flow chart for operation of the punch system during compression is depicted in FIG. 56. The punch system receives information containing the target compression thickness that one or more layer(s) within a cavity is(are) to be compressed. The lower and/or upper punch is(are) then moved to achieve the target thickness. The system then determines whether or not the layer(s) must also be vertically translated within the cavity. If so, the translation is conducted and operation is continued. If not, operation is continued and the upper punch, if it was used, is retracted vertically and the build operation is continued.

Figure 57:
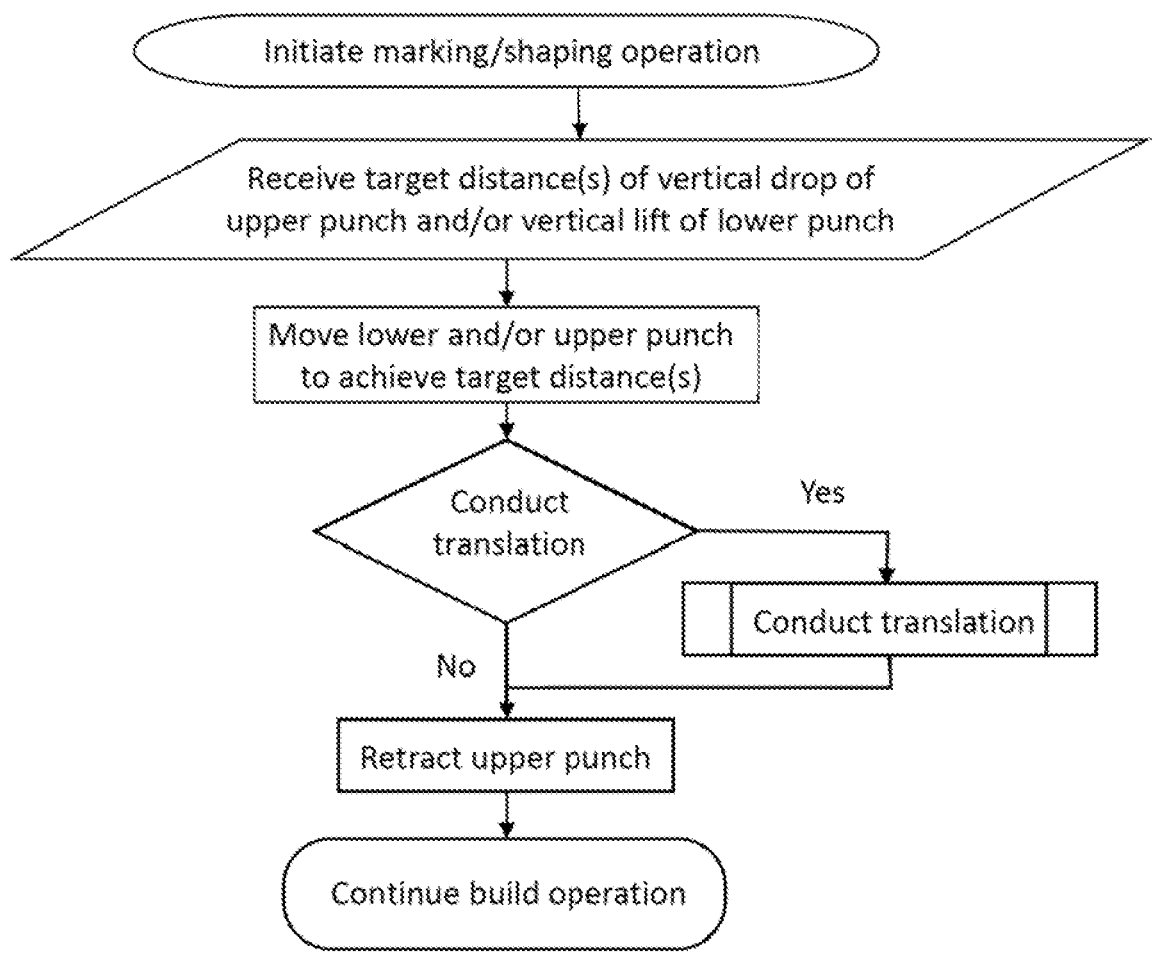
FIG. 57 depicts an exemplary logic flow for conducting a marking or shaping operation with a punch system.

A generalized flow chart for operation of the punch system during marking or shaping is depicted in FIG. 57. The punch system receives information containing the target vertical drop of the upper punch and/or the target vertical lift of the lower punch. The lower and/or upper punch is(are) then moved to achieve the target distance(s). The system then determines whether or not the layer(s) must also be vertically translated within the cavity. If so, the translation is conducted and operation is continued. If not, operation is continued and the upper punch, if it was used, is retracted vertically and the build operation is continued.

In some embodiments, the bed transfer system or article transfer system is adapted to transfer 3DP beds (3DP articles) to one or more liquid removal systems, one or more harvesting systems and/or one or more packaging systems. In some embodiments, the transfer system is integrated with the conveyor system, the liquid removal system or both.

A liquid removal system is adapted to receive one or more build modules, one or more completed 3DP articles and/or one or more in-process 3DP articles and to remove liquid there from. A liquid removal system can be a process area through which one or more of the build modules are conducted. For example, the liquid removal system (61) in FIG. 6 can remove or reduce liquid from the incremented printed layers of an in-process 3DP article. Alternatively, the liquid removal system can be another process area not directly associated with the three-dimensional printing build system, such as a temporary retaining or storage area wherein three-dimensionally printed beds are placed and dried under ambient conditions. In some embodiments, a liquid removal system is one or more dryers.

Figure 45:
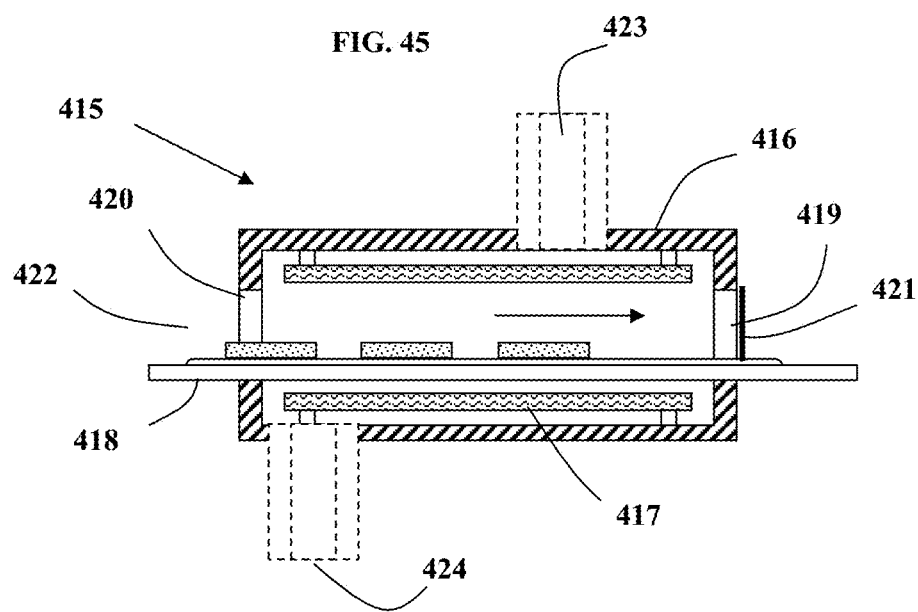
FIG. 45 depicts a sectional side elevation view of an exemplary article drying system.

FIG. 45 depicts an alternate embodiment of a dryer (415) suitable as a liquid removal system. The dryer comprises a housing (416), within which are contained plural heating elements (417) and a conveyor system (418). The housing comprises an inlet (420) and an outlet (419) through which 3DP articles, and optionally their respective build modules, are conducted by way of the conveyor. In some embodiments, the dryer comprises one or more covers (421) for the inlet and/or outlet. The dryer optionally further comprises an exhaust system (423) to remove vapor and/or a heated air source (424) that provides heated air to the dryer.

In some embodiments, the three-dimensionally printed bed comprises loose powder and one or more three-dimensionally printed articles. An equipment assembly of the invention can further comprise one or more harvesting systems adapted to separate loose powder from the one or more three-dimensionally printed articles. In some embodiments, the harvester comprises loose powder collection means and three-dimensionally printed article collection means. In some embodiments, the harvester comprises a vibrating and/or orbiting surface adapted to receive the three-dimensionally printed bed. In some embodiments, the harvester comprises one or more deagglomerators.

In some embodiments, the equipment assembly further comprises one or more dedusters adapted to remove loose powder from articles that have been harvested. In some embodiments, a deduster comprises one or more air brushes. An deduster system comprises a frame, a receiving platform having an air-dispenser, bed transfer mechanism moveably engaged with the frame and superposing a bed transfer region, aspirator(s), deagglomerator, deduster, printed article collector, and powder collector. It can also comprise at least one air brush. An article (or build module) transfer mechanism can comprises mounts adapted to translate along tracks. The bed transfer mechanism also can comprise a receptacle comprising a cavity adapted to receive and temporarily retain 3DP articles. The receptacle can reciprocate in a vertical manner by means of reciprocator engaged with the receptacle and the body of the article transfer mechanism. During operation, a conveyor conducts and positions one or more articles beneath the receptacle and in an article transfer region so as to align the article(s) with the cavity. The receptacle then lowers onto the transport tray an amount sufficient to retain substantially all of the three-dimensionally printed bed within the cavity. An aspirator then aspirates the articles by way of a conduit and a perforated plate in the cavity and above the article, thereby removing a major portion of the loose powder while leaving behind one or more printed articles within the cavity of the receptacle. The bed transfer mechanism then slides/translates the printed articles over one or more airbrushes adapted to direct a flow of air at the printed articles in the cavity to assist in releasing additional loose powder from the printed article(s). A powder collector is adapted to receive loose powder and other solid material not otherwise collected by the aspirator. The article transfer mechanism continues to move until it superposes a deagglomerator. The aspirator is then turned off and the printed particles fall onto of the process tray of the deagglomerator, which is adapted to remove and collect agglomerates from the printed article(s) to provide deagglomerated printed articles. The article transfer mechanism then returns to its original position in preparation of loading and processing of additional articles.

The deduster can also comprise a vibrating process tray adapted to remove and collect dust from the deagglomerated printed articles to provide dedusted printed articles. The finished printed articles are conducted to a printed article collector. The deduster and/or deagglomerator can further comprise solids collector for collecting loose powder and/or agglomerates.

A deduster system may comprise a housing, receptacle, drawer, enclosure, one or more air jets, e.g. air knives, within the enclosure, inlet for the enclosure, and an outlet for the enclosure. A perforated build tray having one or more printed articles that have been harvested is placed in the drawer which is subsequently pushed into the enclosure by way of the inlet, thereby forming a substantially enclosed dedusting area. One or more air jets direct pressurized air toward the printed article(s), whereby both coarse and fine loose powder that has clung onto the printed article(s) is dislodged there from. The loose powder falls into the receptacle and is conducted to the outlet along with the flow of air released by the air jet(s). The dedusted printed article(s) is (are) are retrieved by opening of the drawer. The recovered loose powder collected in a container. Collection of the loose powder can be done manually, mechanically and/or with a vacuum system and/or air-handling system. The deduster system and/or the harvester system can be placed within a larger enclosure to minimize spreading of dust in a process area.

Loose powder, agglomerates or particulates collected during the build cycle, drying, harvesting, deagglomerating and/or dedusting can be disposed or can be blended to form recovered bulk material that can be milled (optionally) and recycled back into a feed supply of virgin unprinted bulk material. Such a bulk material recovery system can comprise one or more vacuum systems, one or more pressurized air systems, one or more non-vacuum mechanical systems, one or more manual systems or a combination thereof for transferring bulk material from one location to another. In some embodiments, the cavity 3DP assembly excludes a harvester and a powder recycle system.

Conveyor systems useful for conducting solid articles from one location to another during manufacture include, by way of example, a modular conveyor, non-modular conveyor, continuous conveyor, contiguous conveyor, conveyor belt, cam, pallet conveyor or link conveyor. Combinations thereof can be used.

Figure 46:
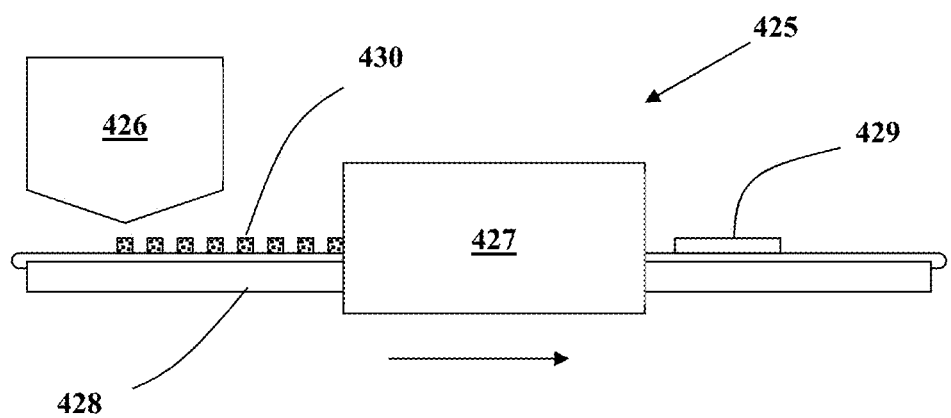
FIG. 46 depicts a side elevation view of an exemplary article packaging system.

FIG. 46 depicts a side elevation view of an exemplary packaging system (425) adapted to package one or more three-dimensionally printed articles (430). The system comprises a hopper (426) that provides three-dimensionally printed articles which are placed onto a conveyor (428). The articles are conducted through a packaging module (427) that places one or more articles into a package (429). Suitable packaging systems can employ bottles, blister packs, tubes, boxes and other such containers.

The various components and systems of the equipment assembly will comprise parts made of durable materials such as metal, plastic, rubber or a combination thereof. In some embodiments, components of the equipment assembly comprise 304 or 316 stainless steel where possible.

Figure 58:
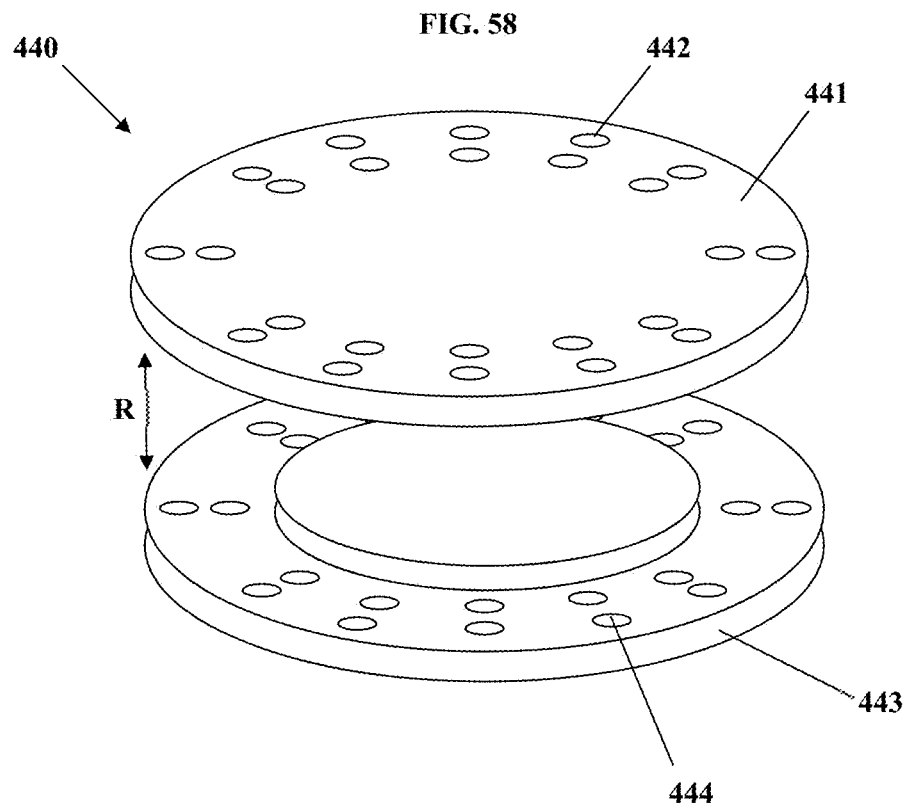
FIG. 58 depicts a perspective view of a turret disc assembly.

FIG. 58 depicts a perspective view of a turret disc assembly (440) comprising a removable upper turret disc (or plate; 441) having plural receptacles (cavities) (442) and a lower turret disc (or plate; 443) having plural respective lower punches (height adjustable platforms, 444) that are vertically aligned with respective cavities of the upper disc. The upper plate is removably engaged with and can be removed from or installed onto the lower plate (Arrow R). The lower plate is optionally removable.

Figure 59:
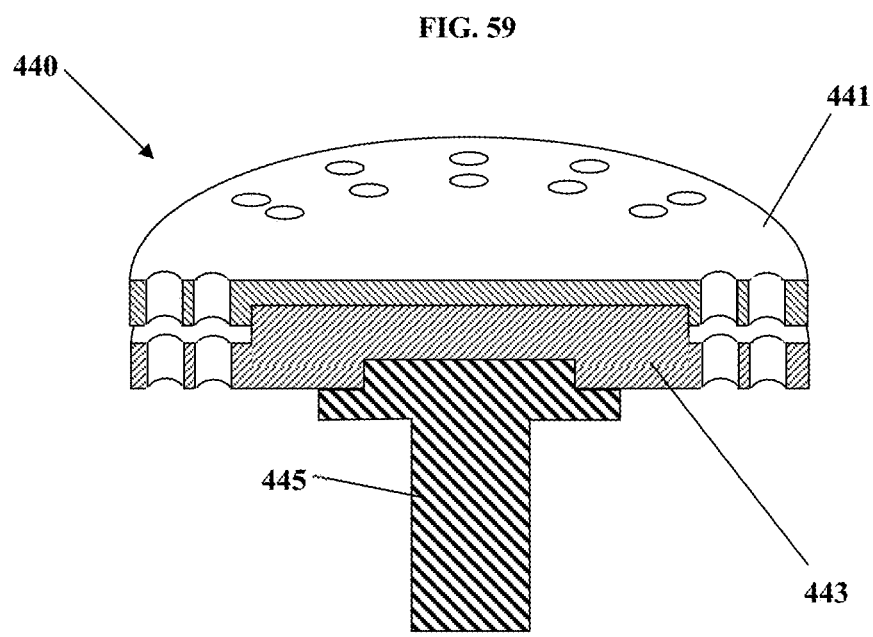
FIG. 59 depicts a cross-sectional side elevation view of the turret disc assembly of FIG. 58.

FIG. 59 depicts a cross-sectional perspective side elevation view of the turret disc assembly (440). The lower disc is engaged with the upper disc and engaged with a drive shaft (445), which rotates (spins) the entire turret assembly during operation. Although a drive shaft is depicted, any other means of actuating and spinning the turret assembly can be used. The lower disc has punches (incrementally height adjustable platforms) that raise into respective receptacles in the upper disc during operation.

Figure 60:
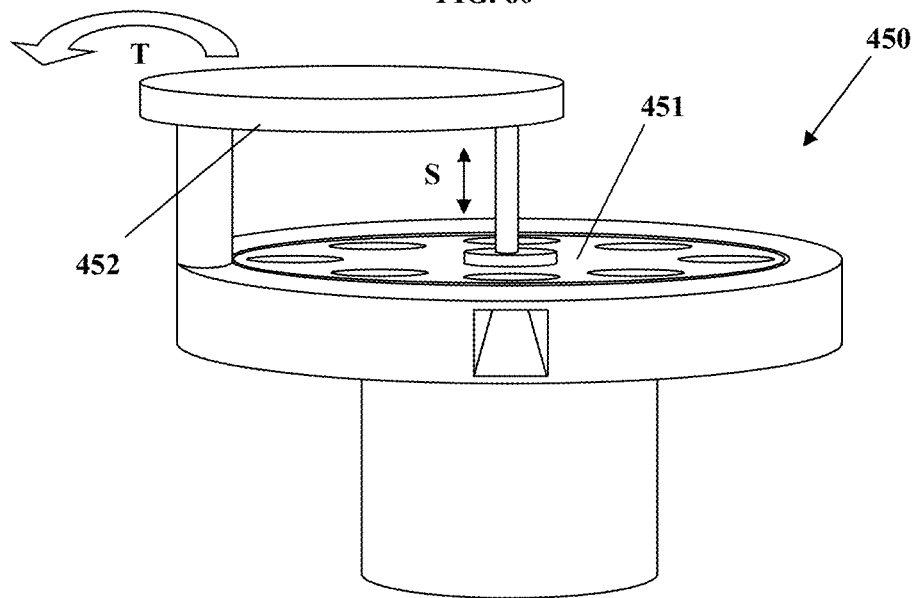
FIG. 60 depicts a perspective view of a 3DP equipment assembly employing a removable turret disc.

Since the upper disc and/or lower disc of the turret disc assembly can be removable, the equipment assembly can further comprise a turret disc replacement system. FIG. 60 depicts a 3DP equipment assembly (450) comprising a turret disc replacement system (452), which removes and installs (Arrow S) turret discs (451). In some embodiments, the replacement system (452) also rotates (Arrow T) about an axis to remove and reinstall the turret disc.

The powder can comprise one or more materials suitable for pharmaceutical or non-pharmaceutical use. In some embodiments, the powder comprises one or more pharmaceutical excipients, one or more pharmaceutically active agents, or a combination thereof. In some embodiments, the three-dimensionally printed article is a pharmaceutical dosage form, medical device, medical implant, or other such article as described.

Exemplary types of pharmaceutical excipients that can be included in a three-dimensionally printed article include, by way of example and without limitation, chelating agent, preservative, adsorbent, acidifying agent, alkalizing agent, antifoaming agent, buffering agent, colorant, electrolyte, flavorant, polishing agent, salt, stabilizer, sweetening agent, tonicity modifier, antiadherent, binder, diluent, direct compression excipient, disintegrant, glidant, lubricant, opaquant, polishing agent, plasticizer, other pharmaceutical excipient, or a combination thereof.

Exemplary types of non-pharmaceutical excipients that can be included in a three-dimensionally printed article include, by way of example and without limitation, ash, clay, ceramic, metal, polymer, biological material, plastic, inorganic material, salt, other such materials or a combination thereof.

In some embodiments, the powder comprises one or more, two or more, three or more, four or more, five or more, six or more, seven or more, eight or more, nine or more, ten or more or plural components, each component being independently selected at each occurrence. In some embodiments, the equipment assembly comprises one or more, two or more, three or more, four or more, five or more, six or more, seven or more, eight or more, nine or more, ten or more or plural powder (or solid component) reservoirs.

Pharmaceutically active agents generally include physiologically or pharmacologically active substances that produce a systemic or localized effect or effects in animals, cells, non-humans and humans. When an active agent is present, any such agent can be used. Exemplary classes of active agents include, by way of example and without limitation, pesticides, herbicides, insecticides, antioxidants, plant growth instigators, sterilization agents, catalysts, chemical reagents, food products, nutrients, cosmetics, vitamins, sterility inhibitors, fertility instigators, microorganisms, flavoring agents, sweeteners, cleansing agents and other such compounds for pharmaceutical, veterinary, horticultural, household, food, culinary, agricultural, cosmetic, industrial, cleaning, confectionery and flavoring applications.

Whenever mentioned and unless otherwise specified, the term "active agent" includes all forms of the active agent including neutral, ionic, salt, basic, acidic, natural, synthetic, diastereomeric, isomeric, enantiomerically pure, racemic, hydrate, chelate, derivative, analog, optically active, optically enriched, free base, free acid, regioisomeric, amorphous, anhydrous and/or crystalline forms.

A three-dimensionally printed dosage form can comprise one, two or more different active agents. Particular combinations of active agents can be provided. Some combinations of active agents include: 1) a first drug from a first therapeutic class and a different second drug from the same therapeutic class; 2) a first drug from a first therapeutic class and a different second drug from a different therapeutic class; 3) a first drug having a first type of biological activity and a different second drug having about the same biological activity; 4) a first drug having a first type of biological activity and a different second drug having a different second type of biological activity. Exemplary combinations of active agents are described herein.

The active agent can be independently selected at each occurrence from active agents such as an antibiotic agent, antihistamine agent, decongestant, anti-inflammatory agent, antiparasitic agent, antiviral agent, local anesthetic, antifungal agent, amoebicidal agent, trichomonocidal agent, analgesic agent, anti-arthritic agent, anti-asthmatic agent, anticoagulant agent, anticonvulsant agent, antidepressant agent, antidiabetic agent, antineoplastic agent, anti-psychotic agent, neuroleptic agent, antihypertensive agent, hypnotic agent, sedative agent, anxiolytic energizer agent, antiparkinson agent, muscle relaxant agent, antimalarial agent, hormonal agent, contraceptive agent, sympathomimetic agent, hypoglycemic agent, antilipemic agent, ophthalmic agent, electrolytic agent, diagnostic agent, prokinetic agent, gastric acid secretion inhibitor agent, anti-ulcerant agent, antiflatulent agent, anti-incontinence agent, cardiovascular agent or a combination thereof. A description of these and other classes of useful drugs and a listing of species within each class can be found in Martindale, The Extra Pharmacopoeia, 31ST Ed. (The Pharmaceutical Press, London 1996), the disclosure of which is incorporated herein by reference in its entirety.

The above-mentioned lists should not be considered exhaustive and are merely exemplary of the many embodiments considered within the scope of the invention. Many other active agents can be included in the powder of the invention.

The liquid applied to the powder can be a solution or suspension. The liquid can comprise an aqueous carrier, nonaqueous carrier, organic carrier or a combination thereof. The aqueous carrier can be water or an aqueous buffer. The nonaqueous carrier can be an organic solvent, low molecular weight polymer, oil, silicone, other suitable material, alcohol, ethanol, methanol, propanol, isopropanol, poly(ethylene glycol), glycol, other such materials or a combination thereof. The terms fluid, printing fluid, binding fluid, and liquid may be used interchangeably to refer to a liquid delivered as part of 3DP.

In some embodiments, the equipment assembly comprises one or more, two or more, three or more, four or more or plural liquid reservoirs. The liquid can be colored or non-colored. The liquid can comprise pigment, paint, dye, tint, ink or a combination thereof.

The liquid can comprise one or more solutes dissolved therein. The powder and/or liquid can comprise one or more binders.

The exemplary embodiments herein should not be considered exhaustive, but merely illustrative of only a few of the many embodiments contemplated by the present invention.

As used herein, the term "about" is taken to mean a value that is within ±10%, ±5% or ±1% of the indicated value.

As used herein, "lead accuracy" of a ball screw shall mean the difference between a specified distance and the actual travel distance of the lead screw nut, as is recognized in the relevant art. This is expressed as an error over a specified travel distance, and helps determine the accuracy rating of the ball screw. "Lead accuracy V300p" shall mean the fluctuation against a travel length of 300 mm.

The entire disclosures of all documents cited herein are hereby incorporated by reference in their entirety.

Example 1

The following materials and procedure are used to prepare three-dimensionally printed dosage forms that dissolve rapidly in saliva.

A powder comprising at least one pharmaceutical carrier is loaded into the powder reservoir. A fluid comprising a liquid and at least one active ingredient is loaded into the fluid reservoir. The equipment assembly is operated, whereby plural stacked incremental layers of printed powder are sequentially formed in build modules by repeatedly passing the build modules through one or more build stations. Typically four to fifty incremental printed powder layers are formed and adhere to each other thereby forming a printed bed having one or more articles surrounded by or embedded in loose powder. The printed beds are dried in a dryer. The printed articles are separated from the loose powder with a harvester. The printed articles are then optionally dedusted with a deduster. The printed articles are then optionally packaged.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. A three-dimensional printing equipment assembly comprising:
a conveyor system that conducts a plurality of build modules, wherein each build module of the plural build modules comprises a body comprising an upper surface and a plurality of receptacles, and a plurality of height adjustable platforms, each height adjustable platform disposed and vertically displaceable within a receptacle of the plurality of receptacles for forming a cavity within the receptacle;
at least one powder layering system that forms one or more layers of powder into the cavity of each receptacle of the plurality of receptacles of each build module of the plural build modules;
at least one binding fluid application system that deposits a binding fluid onto the one or more layers of powder formed in the cavity of the one or more receptacles, to form an incremental printed layer within the cavity of the one or more receptacles; and
at least one punch system comprising at least one upper punch adapted to be lowered to and vertically displaced within the one or more receptacles, the at least one punch system adapted to translate, compress, mark and/or shape the layers of powder or incremental printed layers within the cavity of the one or more receptacles.

2. The equipment assembly of claim 1 further comprising:
(a) a drying system and (b) a discharge system or article transfer system.

3. The equipment assembly of claim 1, wherein: a) the receptacle receives a powder when in the powder layering system to form a powder layer in the receptacle; b) the binding fluid application system is adapted to deposit binding fluid to the layers of powder to form respective incremental printed layers in the receptacle; and c) the punch system is adapted to punch either the powder layer or the incremental printed layer, wherein the punching may result in translating, compressing, marking and/or shaping of the powder layer or incremental printed layer.

4. The equipment assembly of claim 1, wherein during operation of the assembly the receptacle moves: a) from the powder layering system to the binding fluid application system and then to the punch system; b) from the powder layering system to the punch system and then to the binding fluid application system; or c) from the powder layering system to the binding fluid application system then back to the powder layering system and then to the punch system.

5. A three-dimensional printing equipment assembly comprising:
a) a three-dimensional printing build system comprising:
a conveyor system that conducts plural build modules and comprises positioning-controller and plural build module engagements;
plural build modules engaged with the conveyor system, wherein the build modules are adapted to receive and temporarily retain powder from a powder layering system, and wherein a build module comprises: 1) a body comprising an upper surface and a plurality of receptacles, each receptacle comprising one or more sidewalls; and 2) a plurality of incrementally height adjustable platforms (lower punches), each incrementally height adjustable platform disposed within one of the plurality of receptacles to define a cavity therein;
at least one build station comprising: 1) at least one powder layering system that forms incremental powder layers within the cavities of the plurality of receptacles and comprises at least one powder fill head, at least one powder spreader and at least one powder reservoir; and 2) at least one printing system that applies a liquid according to at least one predetermined pattern to the incremental powder layers within the cavities of the plurality of receptacles, and comprises at least one liquid feed system and at least one print head that deposits liquid according to the at least one predetermined pattern; and
at least one punch system comprising at least one upper punch;
wherein the conveyor system repeatedly transports the plural build modules from the at least one powder layering system to the at least one printing system, whereby the three-dimensional printing build system: 1) forms at least one incremental printed layer per build lap in a build module; 2) forms a single three-dimensionally printed article per build cycle in a build module; or 3) forms plural three-dimensionally printed articles per build cycle in a build module; or 4) forms a three-dimensionally printed bed comprising one or more three-dimensionally printed articles and, optionally, unbound or only partially bound powder that has not been printed upon per build cycle in a build module.

6. The three-dimensional printing equipment assembly of claim 5 further comprising at least one liquid removal system that removes liquid from: 1) one or more incremental printed layers of an in-process incompletely formed three-dimensionally printed article; 2) one or more three-dimensionally printed articles after printing thereof; or 3) one or more three-dimensionally printed beds.

7. The equipment assembly of claim 1, wherein the conveyor system comprises a conveyor that is selected from the group consisting of a staged conveyor, turret assembly, belt conveyor, wheel conveyor, roller conveyor, chain conveyor, wire mesh conveyor, plate conveyor, slat conveyor, magnetic conveyor, bucket conveyor, or cart-on-track conveyor.

8. The equipment assembly of claim 7, wherein the turret assembly comprises a removable upper disc comprising plural receptacles and a lower disc comprising plural incrementally height adjustable platforms vertically aligned with respective receptacles of the upper disc.

9. The equipment assembly of claim 7 further comprising a turret disc replacement system.

10. The equipment assembly of claim 1 further comprising: a) at least one layer drying system for in-process drying of an incremental printed layer after formation thereof; and/or b) at least one article drying system for drying of 3DP articles after completion of formation thereof.

11. The equipment assembly of claim 1, wherein: a) the equipment assembly further comprises a conveyor system adapted to conduct plural build modules; b) the equipment assembly further comprises at least one article drying system that receives one or more 3DP articles and removes liquid there from; c) the build system further comprises at least one layer drying system that removes liquid from one or more incremental layers prior to completion of a build cycle; d) the equipment assembly further comprises an article transfer system that transfers 3DP articles, one or more at a time, away from the three-dimensional printing build system; e) the equipment assembly further comprises a dedusting system that removes loose particles from 3DP articles; f) the equipment assembly further comprises one or more control systems; or g) the equipment assembly further comprises one or more inspection systems.

12. The equipment assembly of claim 1, wherein: a) the conveyor system is adapted to repeatedly transport the build modules between the at least one powder layering system, the at least one binding fluid application system and the at least one punch system to form at least one article within a build module; b) the conveyor system is adapted to repeatedly transport the build modules between the at least one powder layering system, the at least one binding fluid application system, the at least one layer drying system and the at least one punch system to form at least one article within a build module; c) the conveyor system is adapted to repeatedly transport the build modules between the at least one powder layering system and the at least one binding fluid application system to form at least one article within a build module; or d) a combination thereof.

13. The equipment assembly of claim 1 further comprising at least one liquid removal system that removes liquid from: 1) one or more incremental printed layers of an in-process incompletely formed three-dimensionally printed article; 2) one or more three-dimensionally printed articles after printing thereof; or 3) one or more three-dimensionally printed beds.

14. The equipment assembly of claim 5, wherein the conveyor system comprises a conveyor that is selected from the group consisting of a staged conveyor, turret assembly, belt conveyor, wheel conveyor, roller conveyor, chain conveyor, wire mesh conveyor, plate conveyor, slat conveyor, magnetic conveyor, bucket conveyor, or cart-on-track conveyor.

15. The equipment assembly of claim 2, wherein during operation of the assembly the receptacle moves from the powder layering system to the binding fluid application system to the drying system and then to the punch system.

16. The equipment assembly of claim 2, wherein the conveyor system is adapted to repeatedly transport the at least one build module between the at least one powder layering system, the at least one binding fluid deposition system, the at least one layer drying system and the at least one punch system to form at least one article within the at least one build module.

* * * * *